(12) United States Patent
Tomarev et al.

(10) Patent No.: US 11,058,729 B2
(45) Date of Patent: Jul. 13, 2021

(54) EXOSOMES AND MIRNA TO TREAT GLAUCOMA

(71) Applicant: THE UNITED STATES OF AMERICA, as represented by the Secretary, Department of Health and Human Services, Bethesda, MD (US)

(72) Inventors: Stanislav Ivanovich Tomarev, Kensington, MD (US); Benjamin Frank John Martin Mead, Silver Spring, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 59 days.

(21) Appl. No.: 16/257,026

(22) Filed: Jan. 24, 2019

(65) Prior Publication Data
US 2019/0224242 A1   Jul. 25, 2019

Related U.S. Application Data

(60) Provisional application No. 62/622,032, filed on Jan. 25, 2018.

(51) Int. Cl.
| | | |
|---|---|---|
| *A61K 48/00* | (2006.01) | |
| *A61K 35/28* | (2015.01) | |
| *A61P 27/10* | (2006.01) | |
| *C12N 5/0775* | (2010.01) | |
| *A61K 9/00* | (2006.01) | |
| *C12N 15/113* | (2010.01) | |
| *A61K 45/06* | (2006.01) | |

(52) U.S. Cl.
CPC ............ *A61K 35/28* (2013.01); *A61K 9/0019* (2013.01); *A61K 9/0048* (2013.01); *A61P 27/10* (2018.01); *C12N 5/0663* (2013.01); *C12N 15/113* (2013.01); *A61K 45/06* (2013.01); *C12N 2310/14* (2013.01); *C12N 2310/141* (2013.01)

(58) Field of Classification Search
CPC ............................. A61K 2300/00; A61K 35/28
See application file for complete search history.

(56) References Cited

U.S. PATENT DOCUMENTS

| | | | | |
|---|---|---|---|---|
| 8,808,682 | B2 * | 8/2014 | Ra ......................... | A61P 31/00 424/93.1 |
| 2017/0183686 | A1 | 6/2017 | Khvorova et al. | |
| 2017/0296588 | A1 * | 10/2017 | Ichim ...................... | A61K 35/28 |
| 2017/0369559 | A9 * | 12/2017 | Graham .................. | C07K 16/18 |
| 2019/0022144 | A1 * | 1/2019 | Song ........................ | A61P 1/00 |

FOREIGN PATENT DOCUMENTS

WO   WO 2016/172598 A1   10/2016

OTHER PUBLICATIONS

Yu et al. (Int. J. Mol. Sci., 2014, 15, 4142-4157).*
Klingeborn et al. (Progress in Retinal and Eye Research, 59, 2017, 158-177).*
Mead and Tomarev "Exosome-derived from bone marrow mesenchymal stem cells promote retinal ganglion cell survival in two models of glaucoma," *Society for Neuroscience,* Washington DC (Poster Presentation) (Nov. 2017).
Mead and Tomarev, "BMSC-derived exosomes promote retinal ganglion cell survival in multiple rodent models of glaucoma," *ARVO,* Hawaii (Abstract) (May 2018).
Mead and Tomarev, "Bone marrow-derived mesenchymal stem cells-derived exosomes promote survival of retinal ganglion cells through miRNA-dependent Mechanisms," *Stem Cells Translational Medicine* 6: 1273-1285 (2017).
Mead and Tomarev, "Exosome-derived from bone marrow mesenchymal stem cells promote retinal ganglion cell survival in two models of glaucoma," *International Society for Eye Research.* Atlanta, (Poster Presentation) (Sep. 2017).
Mead and Tomarev, "Mesenchymal stem cell-derived exosomes for the treatment of traumatic and degenerative eye disease," *ARVO,* Baltimore (Abstract) (May 2017).
Mead and Tomarev, "Retinal ganglion cell neuroprotection by growth factors and exosomes: lessons from mesenchymal stem cells," *Neural Regen Res.* 13(2): 228-229 (Feb. 2018).
Mead et al., "Mesenchymal stem cell-derived small extracellular vesicles promote neuroprotection in a genetic DBA/2J mouse model of glaucoma," *IVOS* 59(13): 5473-5480 (2018).
"NEI scientists find that stem cell exosomes promote survival of retinal ganglion cells in rats," EXOMErna downloaded from the internet at: http://www.exosome-rna.com/nei-scientists-find-that-stem-cell-exosomes-promote-survival-of-retinal-ganglion-cells-in-rats/ printed to PDF 2 pages (press release Jan. 31, 2017).
Tomarev et al., "Mesenchymal stem cell-derived exosomes promote retinal ganglion cell survival after optic nerve crush and in rodent models of glaucoma," *XXIII Biennial Meeting of the International Society for Eye Research.* Belfast, UK (Abstract) (Sep. 2018).
Yu et al., "Exosomes derived from MSCs ameliorate retinal laser injury partially by inhibition of MCP-1," *Scientific Reports* 6: 34562 (12 pages) (Sep. 30, 2016).
Du et al., "Effects of intravitreal anti-VEGF therapy on glaucoma-like progression in susceptible eyes," *Journal of Glaucoma* 28(12): 1035-1040 (Dec. 2019)(Abstract).
Johnson et al., "Neuroprotective effects of intravitreal mesenchymal stem cell transplantation in experimental glaucoma," *Investigative Ophthalmology & Visual Science* 51(4): 2051-2059 (Apr. 2010).
Khatib and Martin, "Neuroprotection in glaucoma: Towards clinical trials and precision medicine," *Current Eye Research* 45(3): 327-338 (e-Pub Sep. 16, 2019)(Abstract).

* cited by examiner

*Primary Examiner* — Amy H Bowman
(74) *Attorney, Agent, or Firm* — Klarquist Sparkman, LLP

(57) ABSTRACT

Methods are disclosed herein for treating glaucoma in a subject. In some embodiments, the methods increase retinal ganglion cell survival. The disclosed method use exosomes and/or miRNA.

13 Claims, 32 Drawing Sheets
(22 of 32 Drawing Sheet(s) Filed in Color)
Specification includes a Sequence Listing.

FIG. 1A intravitreal sEV treatment (single/weekly/monthly)

Microbead model: Day 0 — Day 56

Laser model: Day 0 — Day 21

Microbead injection/laser photocoagulation — Animals sacrificed

| Group | No. of animals (eyes) | Injury | Treatment |
|---|---|---|---|
| 1 | 5 (10) | Uninjured | Untreated |
| 2 | 5 (10) | Microbeads | Untreated |
| 2 | 5 (10) | Microbeads | Single (day 0) BMSC-derived sEV |
| 2 | 5 (10) | Microbeads | Monthly BMSC-derived sEV |
| 2 | 5 (10) | Microbeads | Weekly BMSC-derived sEV |
| 2 | 5 (10) | Microbeads | Monthly fibroblast-derived sEV |
| 2 | 5 (10) | Microbeads | Weekly fibroblast-derived sEV |
| 3 | 5 (10) | Laser | Untreated |
| 3 | 5 (10) | Laser | Single (day 0) BMSC-derived sEV |
| 3 | 5 (10) | Laser | Weekly BMSC-derived sEV |
| 3 | 5 (10) | Laser | Weekly siAgo2 BMSC-derived sEV |
| 3 | 5 (10) | Laser | Weekly siScr BMSC-derived sEV |
| 3 | 5 (10) | Laser | Single (day 0) fibroblast-derived sEV |
| 3 | 5 (10) | Laser | Weekly fibroblast-derived sEV |

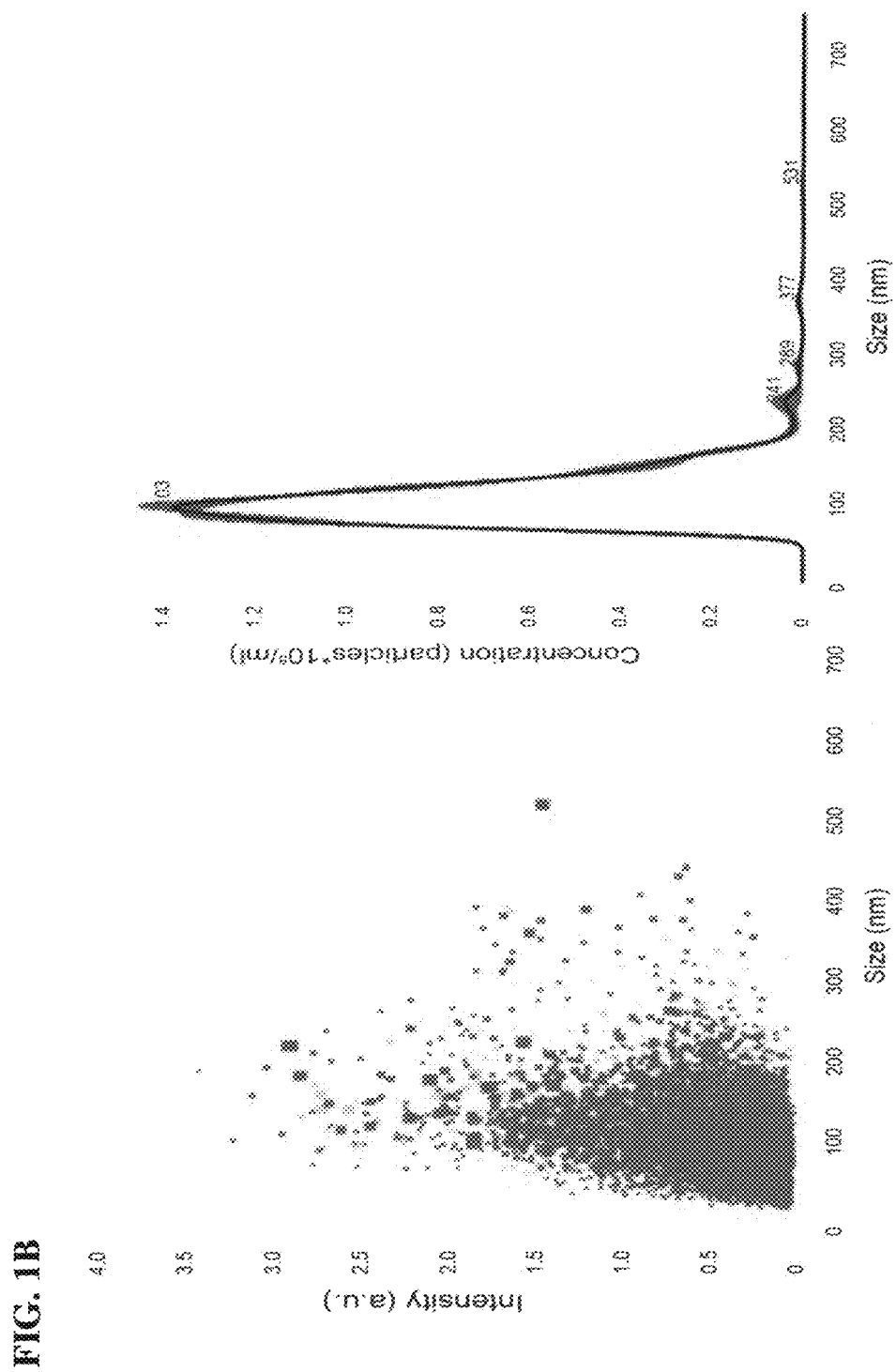

FIG. 2B

Legend (Laser + sEV):
- Intact
- Laser
- Single BMSC
- Weekly BMSC
- Weekly siScr
- Weekly siAgo2
- Single fibroblast
- Weekly fibroblast Y-axis: Mean intraocular pressure (mmHg)
X-axis: Day

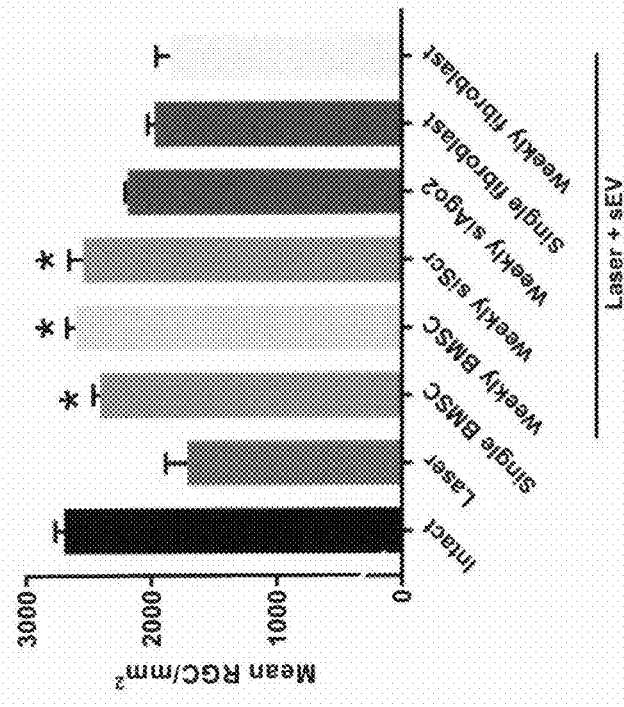
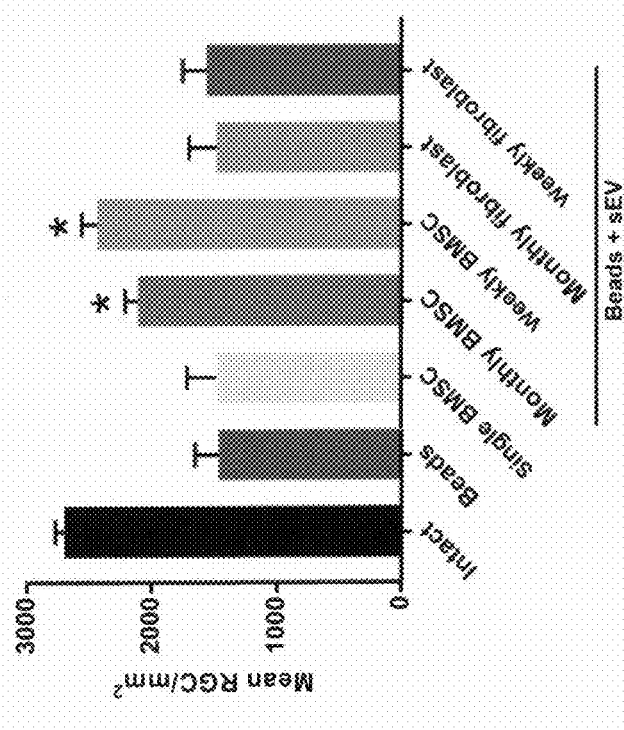

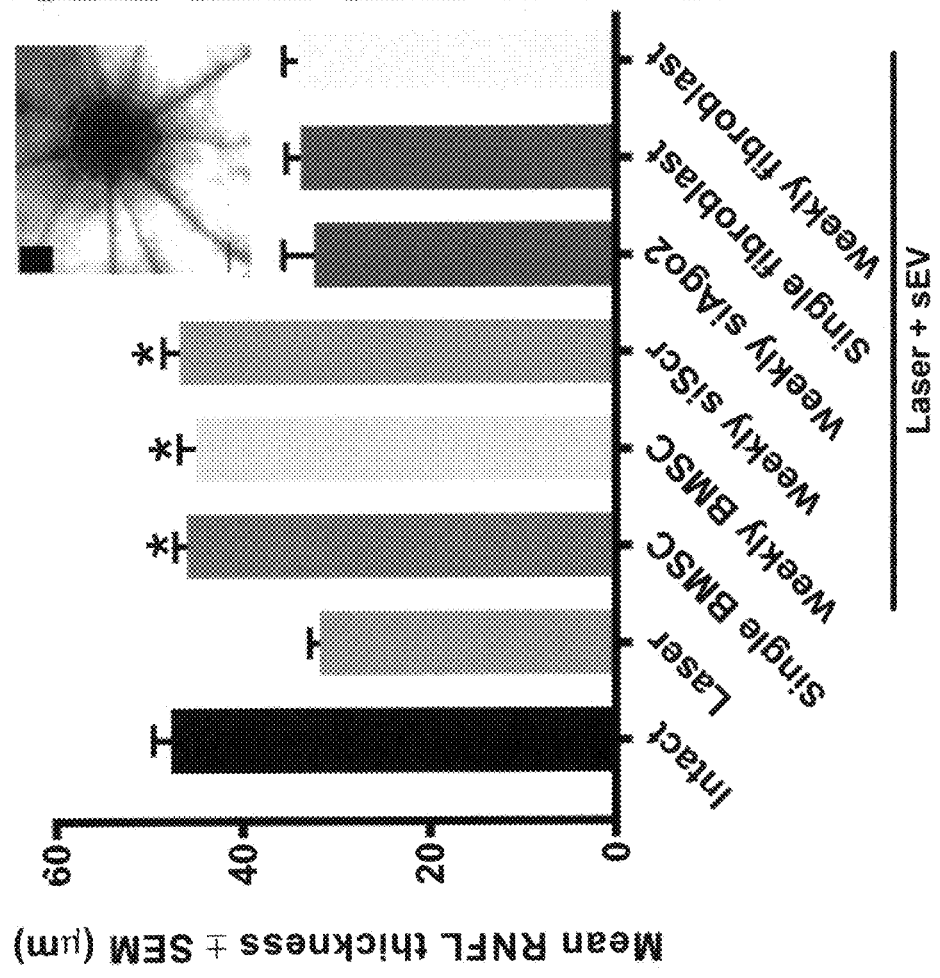
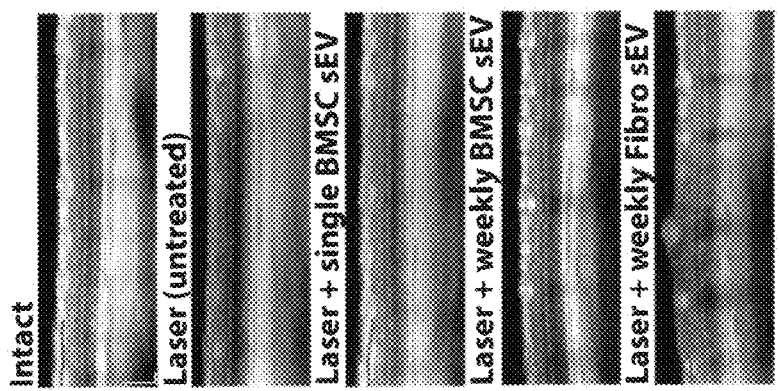
FIG. 4A
FIG. 4B
FIG. 4C

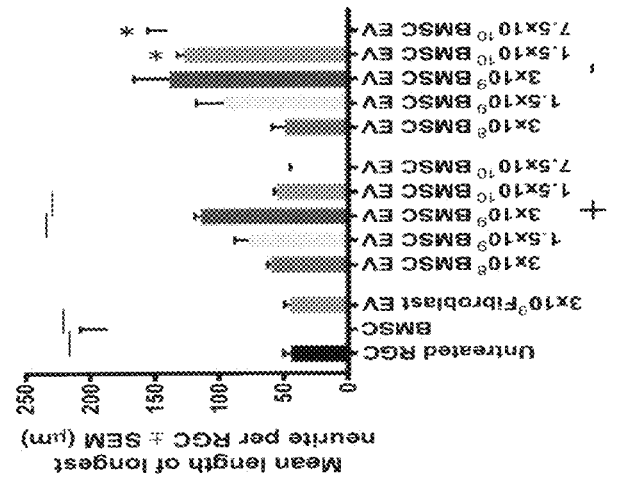
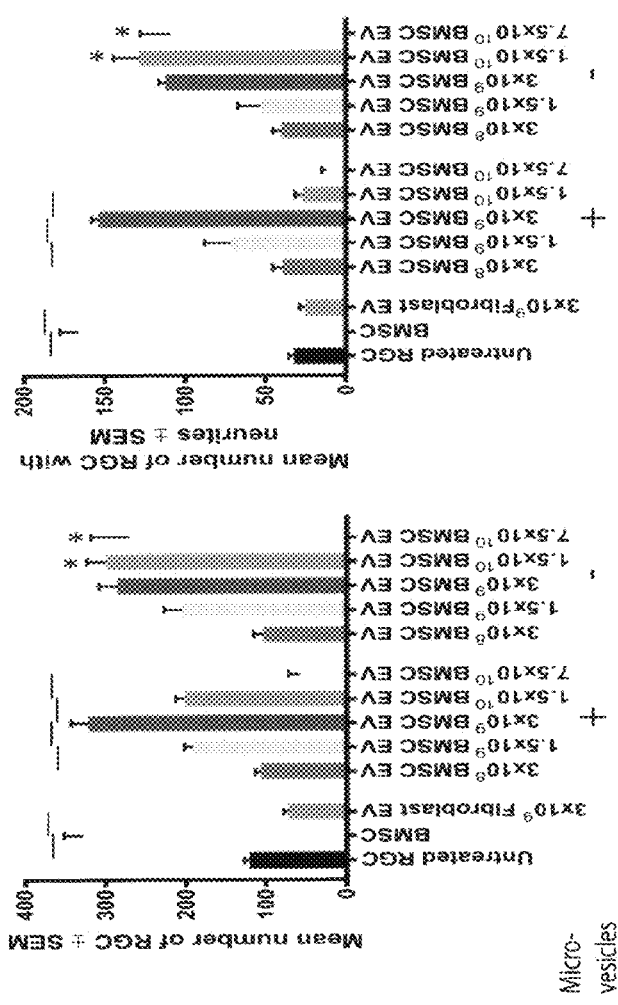
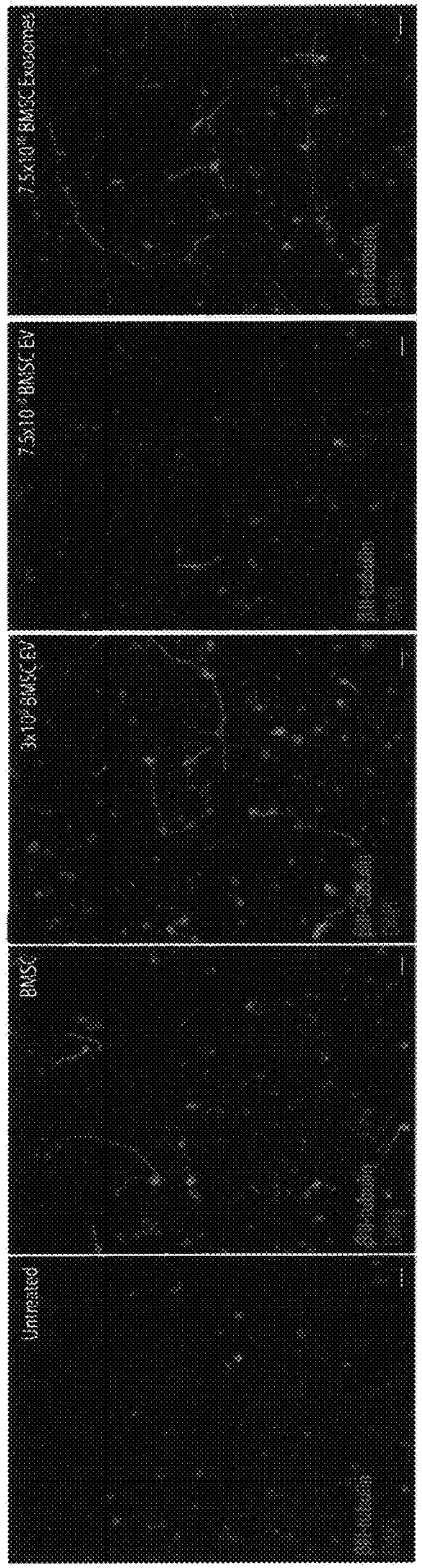

FIG. 11A
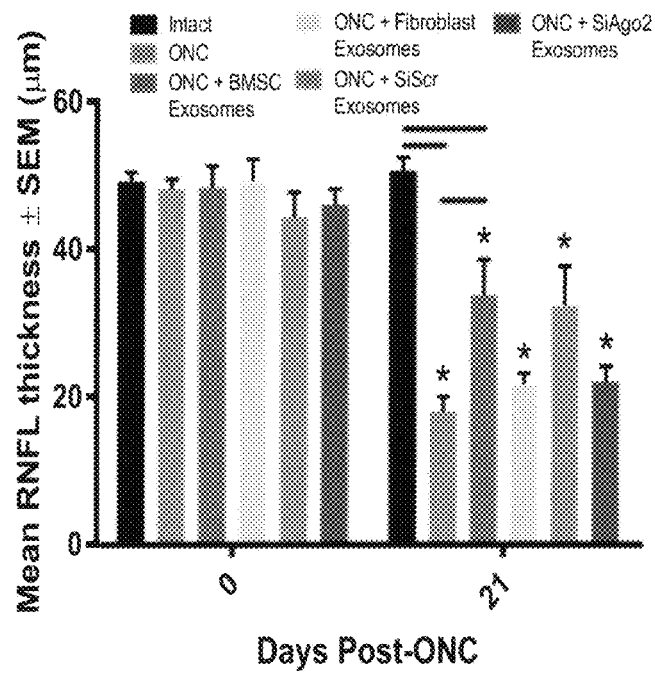
FIG. 11B
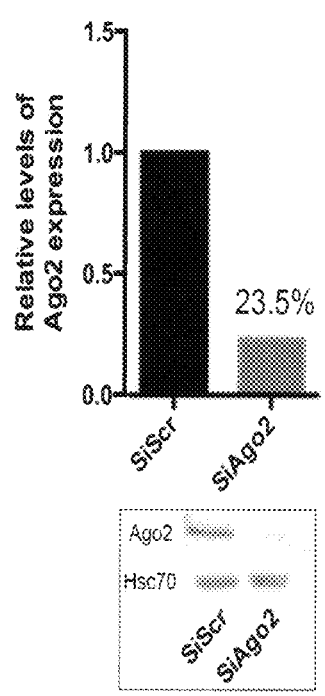
FIG. 11C
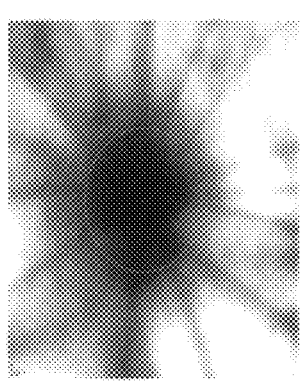
FIG. 11D
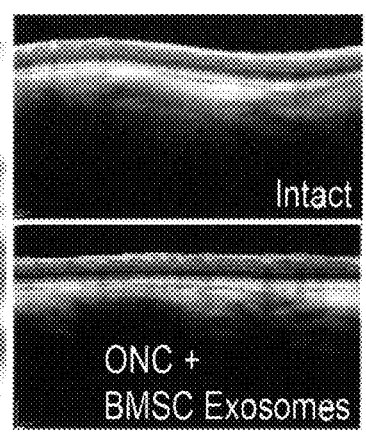
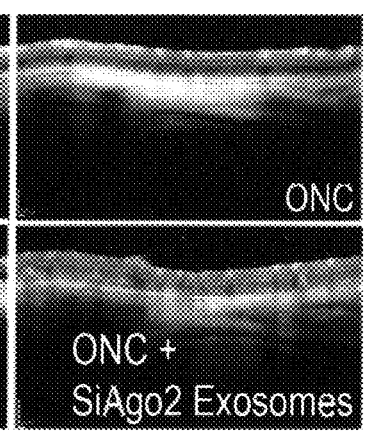

FIG. 12A
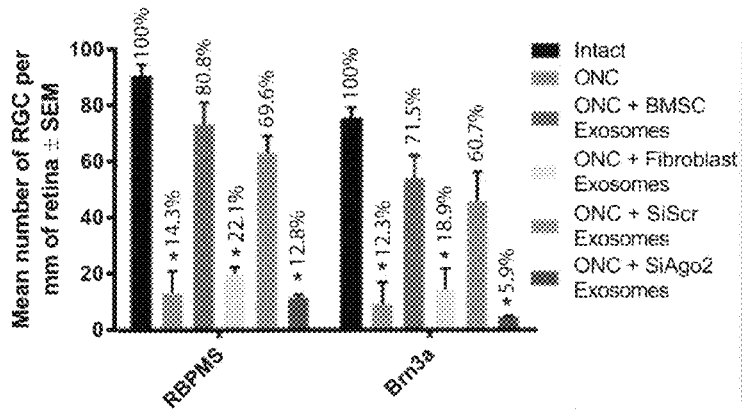
FIG. 12B
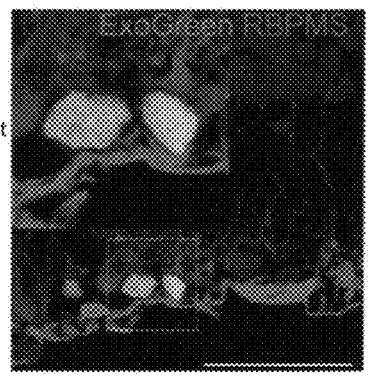
Intact
ONC
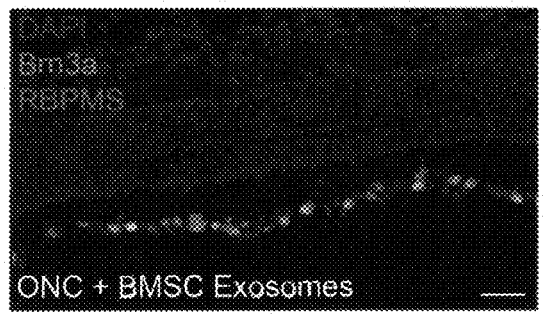
ONC + BMSC Exosomes
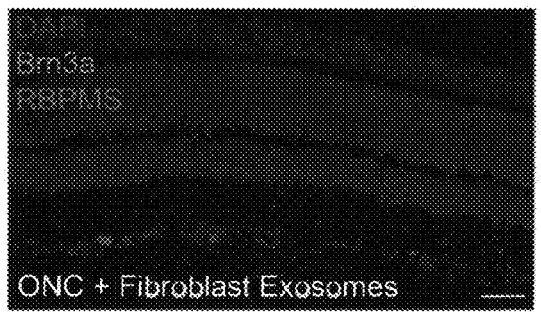
ONC + Fibroblast Exosomes
ONC + SiScr Exosomes
ONC + SiAgo2 Exosomes
FIG. 12C FIG. 14A
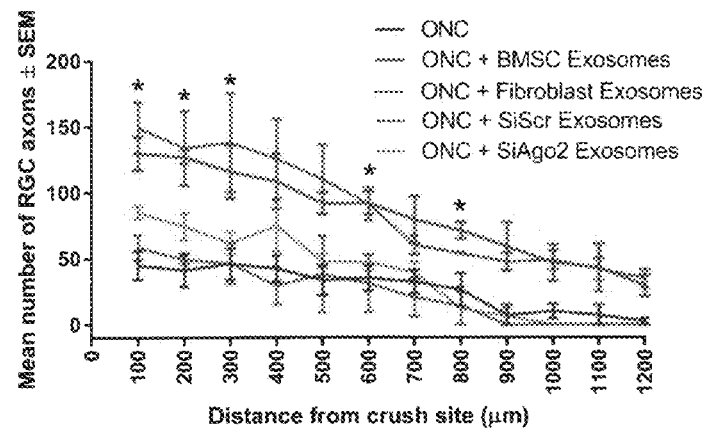
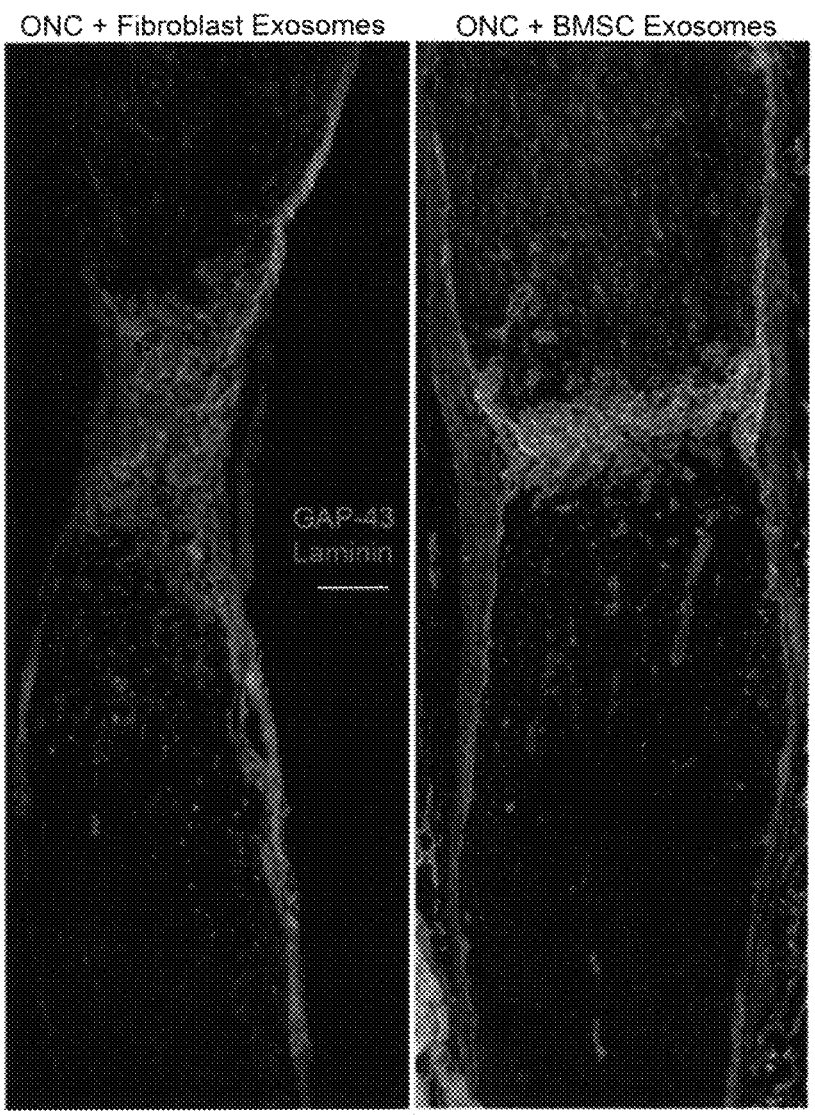
FIG. 14B

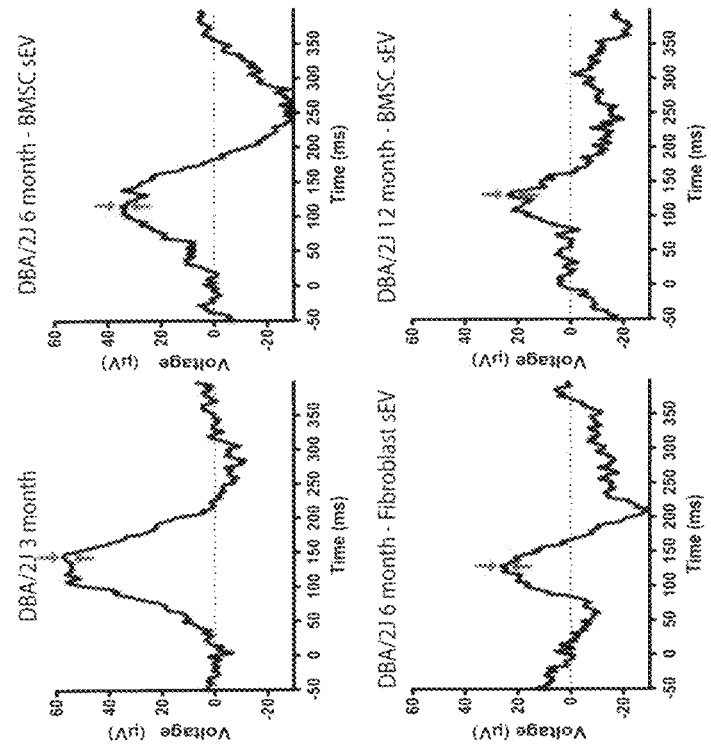
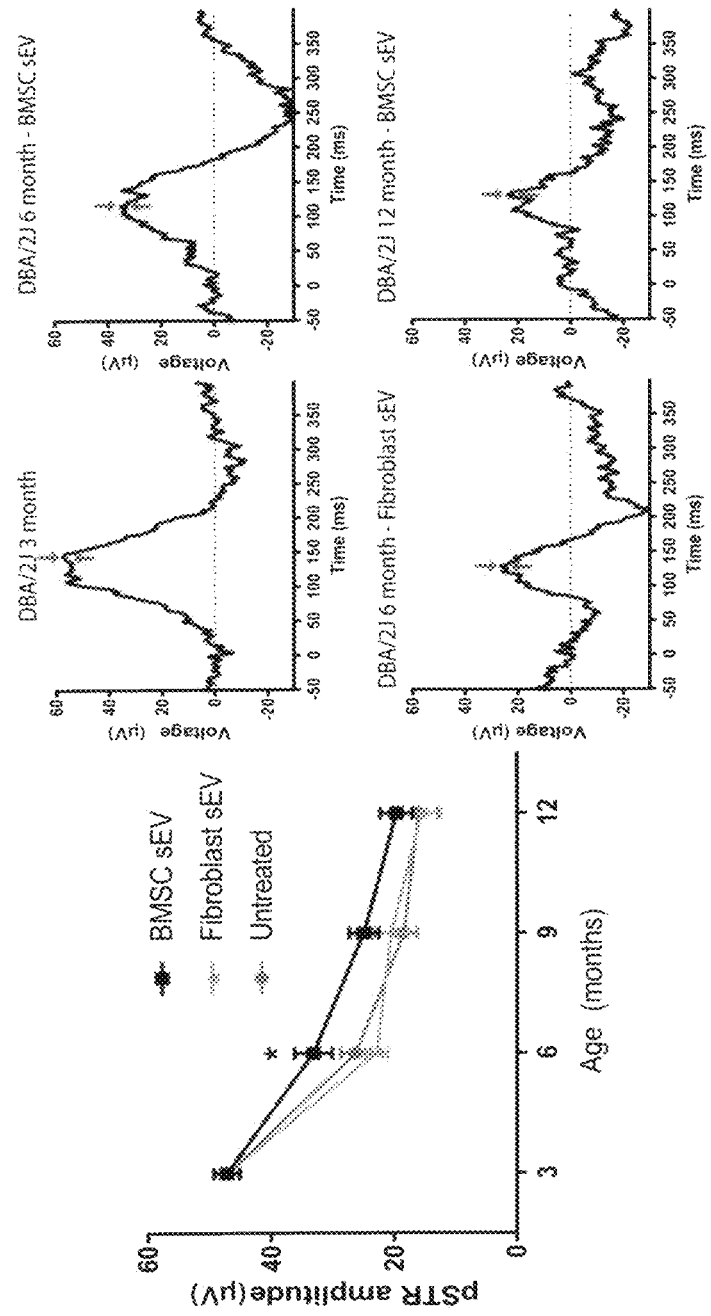
FIG. 17A
FIG. 17B

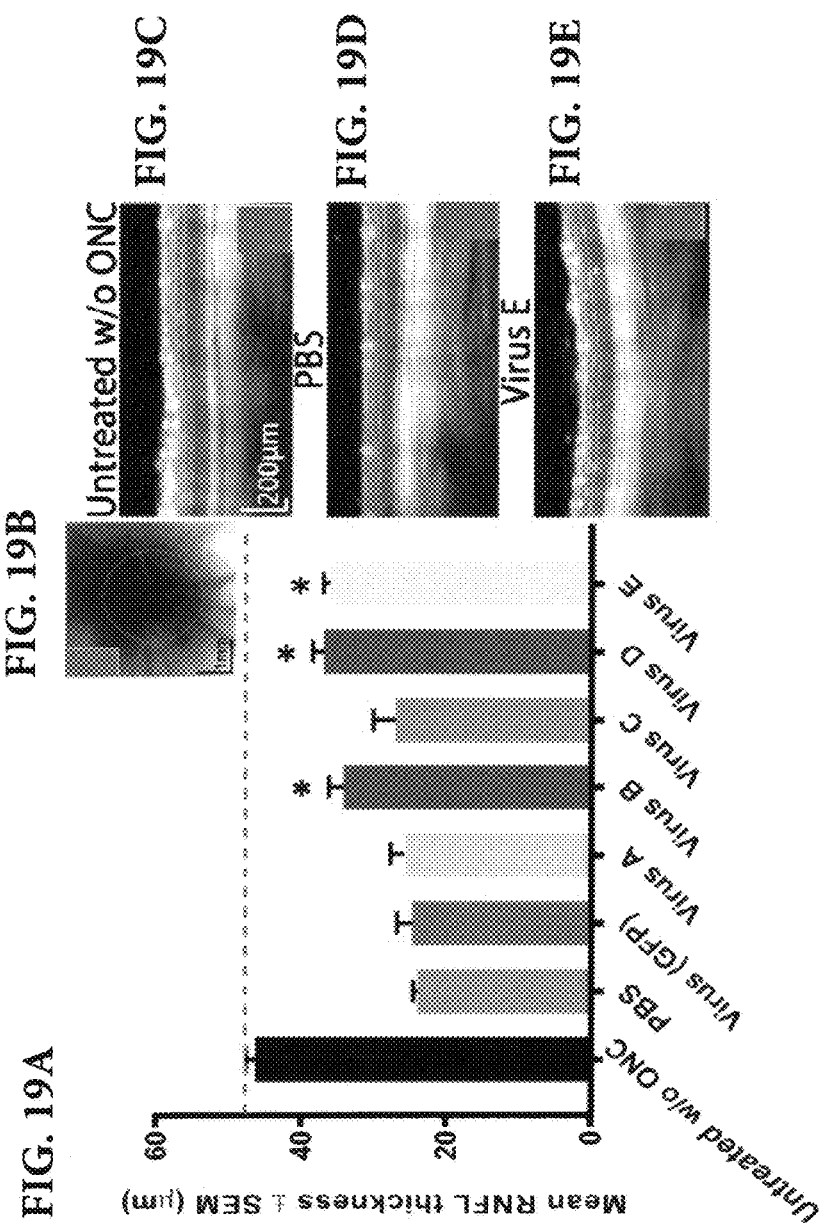

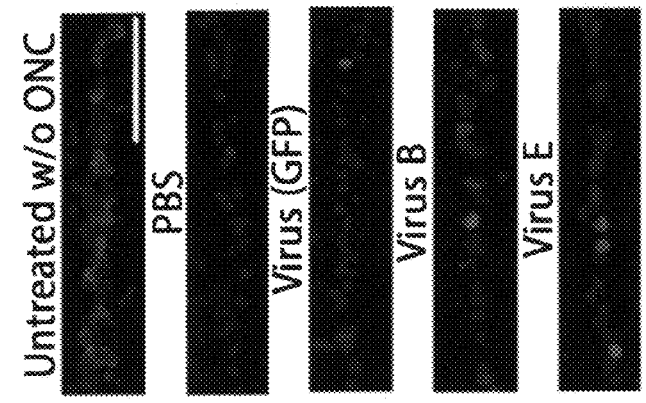
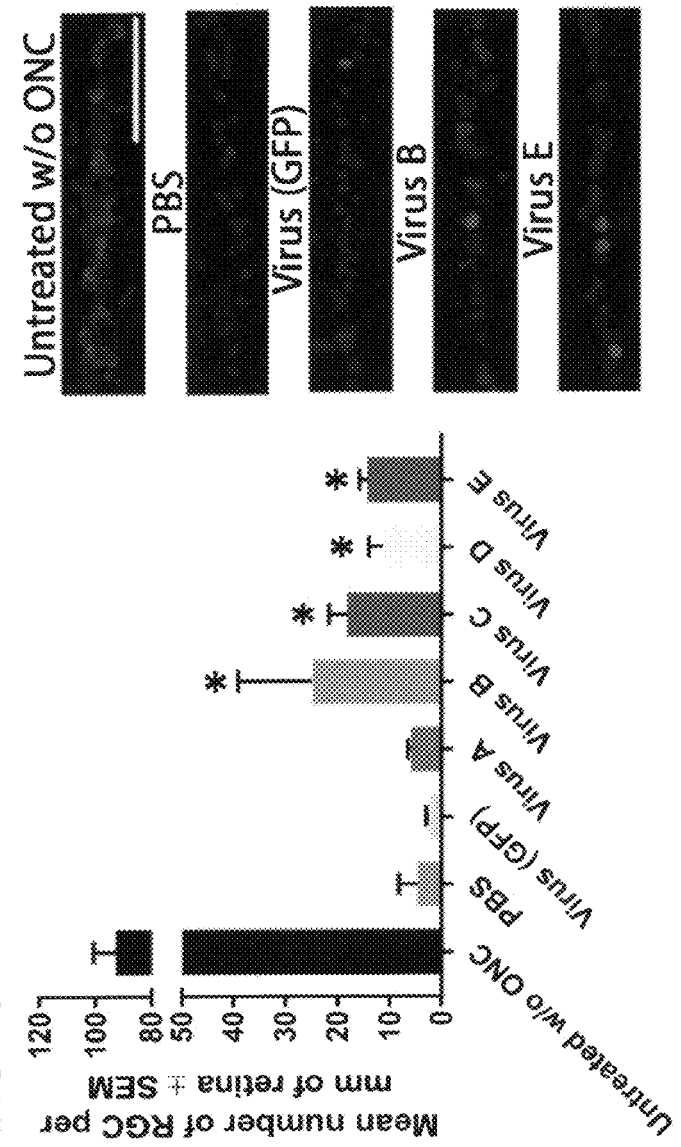
FIG. 20A
FIG. 20B

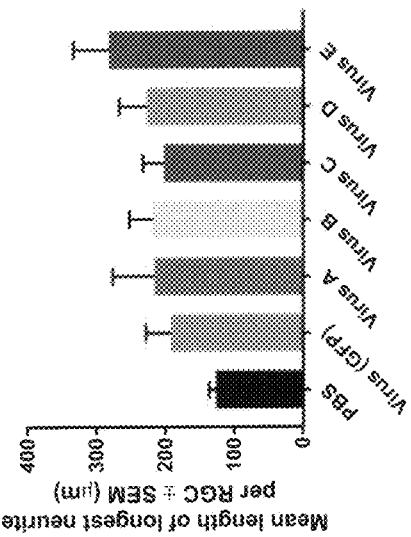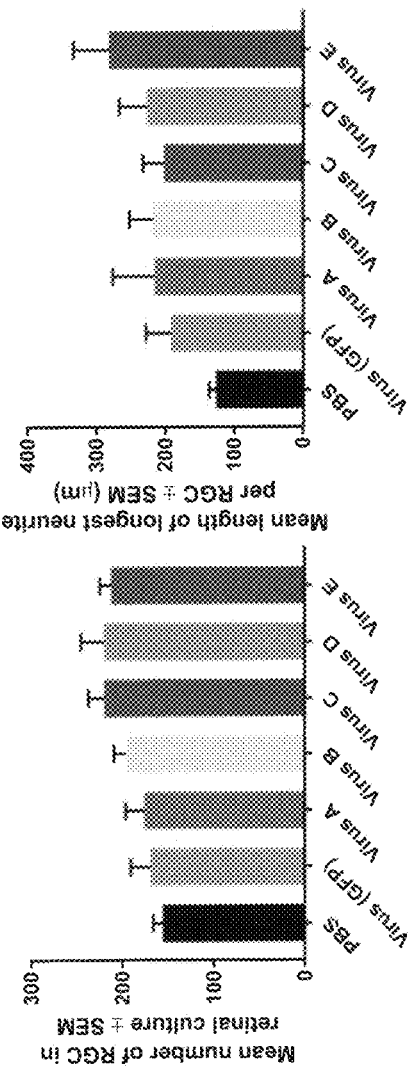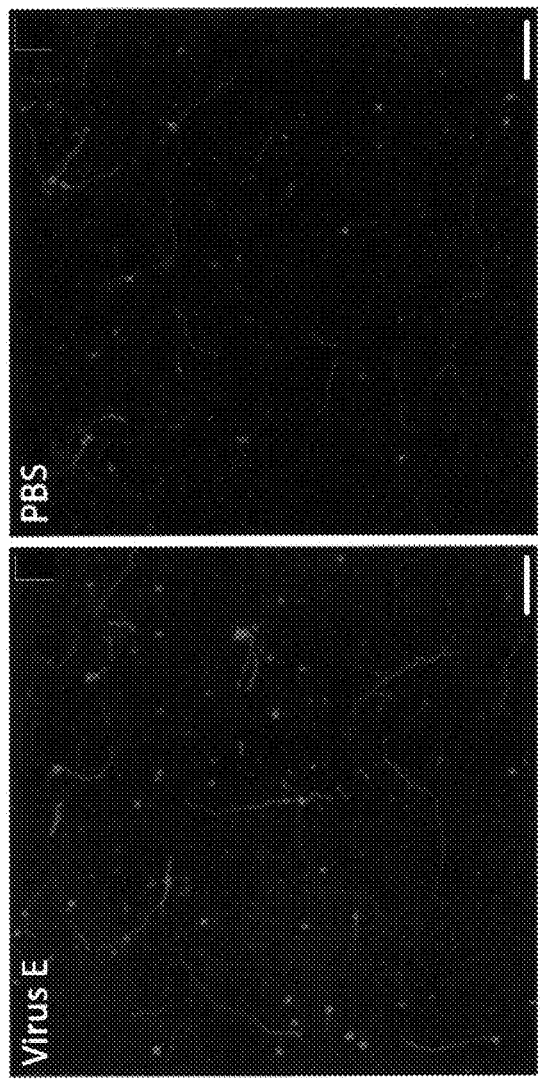

| Symbol/Description | Stem-loop | Accession N° |
|---|---|---|
| HGNC:MIR26A1 | (stem-loop structure) | MI0000083 |
| HGNC:MIR17 | (stem-loop structure) | MI0000071 |
| HGNC:MIR30C2 | (stem-loop structure) | MI0000254 |
| HGNC:MIR92A1 | (stem-loop structure) | MI0000093 |
| miR-292 stem-loop | (stem-loop structure) | MI0000966 |
| HGNC:MIR182 | (stem-loop structure) | MI0000272 | though current therapies can successfully reduce intraocular pressure (IOP), the critical risk factor associated with glaucoma, no neuroprotective strategies currently exist. Thus, a need remains for agents that can be used to treat glaucoma, and other diseases related to decreases in retinal ganglion cell survival.

SEQUENCE LISTING

```
<160> NUMBER OF SEQ ID NOS: 71

<210> SEQ ID NO 1
<211> LENGTH: 22
<212> TYPE: RNA
<213> ORGANISM: Homo sapiens

<400> SEQUENCE: 1
uaauacugcc ugguaaugau ga                                       22

<210> SEQ ID NO 2
<211> LENGTH: 23
<212> TYPE: RNA
<213> ORGANISM: Homo sapiens

<400> SEQUENCE: 2
uguaguguuu ccuacuuuau gga                                      23

<210> SEQ ID NO 3
<211> LENGTH: 22
<212> TYPE: RNA
<213> ORGANISM: Homo sapiens

<400> SEQUENCE: 3
uauguaacau gguccacuaa cu                                       22

<210> SEQ ID NO 4
<211> LENGTH: 23
<212> TYPE: RNA
<213> ORGANISM: Homo sapiens

<400> SEQUENCE: 4
acuccauuug uuuugaugau gga                                      23

<210> SEQ ID NO 5
<211> LENGTH: 84
<212> TYPE: RNA
<213> ORGANISM: Homo sapiens

<400> SEQUENCE: 5
gcuggcgucg gugcugggga gcggcccccg ggugggccuc ugcucuggcc ccuccugggg    60
cccgcacucu cgcucugggc ccgc                                         84
```

```
<210> SEQ ID NO 6
<211> LENGTH: 22
<212> TYPE: RNA
<213> ORGANISM: Homo sapiens

<400> SEQUENCE: 6
gggggucccc ggugcucgga uc                                              22

<210> SEQ ID NO 7
<211> LENGTH: 84
<212> TYPE: RNA
<213> ORGANISM: Homo sapiens

<400> SEQUENCE: 7
gcuggcgucg gugcugggga gcggcccccg ggugggccuc ugcucuggcc ccuccugggg     60
cccgcacucu cgcucugggc ccgc                                           84

<210> SEQ ID NO 8
<211> LENGTH: 84
<212> TYPE: RNA
<213> ORGANISM: Homo sapiens

<400> SEQUENCE: 8
cuccccaugg cccugucucc caacccuugu accagugcug ggcucagacc cugguacagg     60 ccuggggac agggaccugg ggac                                            84

<210> SEQ ID NO 9
<211> LENGTH: 22
<212> TYPE: RNA
<213> ORGANISM: Homo sapiens

<400> SEQUENCE: 9
ucucccaacc cuuguaccag ug                                             22

<210> SEQ ID NO 10
<211> LENGTH: 23
<212> TYPE: RNA
<213> ORGANISM: Homo sapiens

<400> SEQUENCE: 10
gcaaagcaca cggccugcag aga                                            23

<210> SEQ ID NO 11
<211> LENGTH: 94
<212> TYPE: RNA
<213> ORGANISM: Homo sapiens

<400> SEQUENCE: 11
cuuuggcgau cacugccucu cugggccugu gucuuaggcu cugcaagauc aaccgagcaa     60
agcacacggc cugcagagag gcagcgcucu gccc                                94

<210> SEQ ID NO 12
<211> LENGTH: 22
<212> TYPE: RNA
<213> ORGANISM: Homo sapiens

<400> SEQUENCE: 12
cguguauuug acaagcugag uu                                             22
```

-continued

```
<210> SEQ ID NO 13
<211> LENGTH: 22
<212> TYPE: RNA
<213> ORGANISM: Homo sapiens

<400> SEQUENCE: 13
ucguaccgug aguaauaaug cg                                              22

<210> SEQ ID NO 14
<211> LENGTH: 110
<212> TYPE: RNA
<213> ORGANISM: Homo sapiens

<400> SEQUENCE: 14
ccuggccucc ugcagugcca cgcuccgugu auuugacaag cugaguugga cacuccaugu     60
gguagagugu caguuuguca aauacccaa gugcggcaca ugcuuaccag               110

<210> SEQ ID NO 15
<211> LENGTH: 22
<212> TYPE: RNA
<213> ORGANISM: Homo sapiens

<400> SEQUENCE: 15
ugucaguuug ucaaauaccc ca                                              22

<210> SEQ ID NO 16
<211> LENGTH: 85
<212> TYPE: RNA
<213> ORGANISM: Homo sapiens

<400> SEQUENCE: 16
cgcuggcgac gggacauuau acuuuuggu acgcgcugug acacuucaaa cucguaccgu      60
gaguaauaau gcgccgucca cggca                                           85

<210> SEQ ID NO 17
<211> LENGTH: 21
<212> TYPE: RNA
<213> ORGANISM: Homo sapiens

<400> SEQUENCE: 17
cauuauuacu uuugguacgc g                                               21

<210> SEQ ID NO 18
<211> LENGTH: 22
<212> TYPE: RNA
<213> ORGANISM: Homo sapiens

<400> SEQUENCE: 18
aagacgggag gaaagaaggg ag                                              22

<210> SEQ ID NO 19
<211> LENGTH: 80
<212> TYPE: RNA
<213> ORGANISM: Homo sapiens

<400> SEQUENCE: 19
gguacuugaa gagugguuau cccugcugug uucgcuuaau uuaugacgaa ucauacaggg     60
acauccaguu uuucaguauc                                                 80
```

```
<210> SEQ ID NO 20
<211> LENGTH: 23
<212> TYPE: RNA
<213> ORGANISM: Homo sapiens

<400> SEQUENCE: 20
ucucacacag aaaucgcacc cgu                                              23

<210> SEQ ID NO 21
<211> LENGTH: 86
<212> TYPE: RNA
<213> ORGANISM: Homo sapiens

<400> SEQUENCE: 21
gguggguggu uucuccguuu gccuguuucg cugaugugca uucaacucau ucucagcaaa      60
auaagcaaau ggaaaauucg uccauc                                          86

<210> SEQ ID NO 22
<211> LENGTH: 86
<212> TYPE: RNA
<213> ORGANISM: Homo sapiens

<400> SEQUENCE: 22
gguggguggu uucuccguuu gccuguuucg cugaugugca uucaacucau ucucagcaaa      60
auaagcaaau ggaaaauucg uccauc                                          86

<210> SEQ ID NO 23
<211> LENGTH: 23
<212> TYPE: RNA
<213> ORGANISM: Homo sapiens

<400> SEQUENCE: 23
aaugacacga ucacucccgu uga                                              23

<210> SEQ ID NO 24
<211> LENGTH: 22
<212> TYPE: RNA
<213> ORGANISM: Homo sapiens

<400> SEQUENCE: 24
uuuuucauua uugcuccuga cc                                               22

<210> SEQ ID NO 25
<211> LENGTH: 22
<212> TYPE: RNA
<213> ORGANISM: Homo sapiens

<400> SEQUENCE: 25
acucggcgug gcgucggucg ug                                               22

<210> SEQ ID NO 26
<211> LENGTH: 22
<212> TYPE: RNA
<213> ORGANISM: Homo sapiens

<400> SEQUENCE: 26
cuuucagucg gauguuuaca gc                                               22

<210> SEQ ID NO 27
<211> LENGTH: 21
<212> TYPE: RNA
<213> ORGANISM: Homo sapiens
```

```
<400> SEQUENCE: 27
uaguagaccg uauagcguac g                                          21

<210> SEQ ID NO 28
<211> LENGTH: 96
<212> TYPE: RNA
<213> ORGANISM: Homo sapiens

<400> SEQUENCE: 28
ugguacuugg agagauagua gaccguauag cguacgcuuu aucugugacg uauguaacac  60
gguccacuaa cccucaguau caaauccauc cccgag                           96

<210> SEQ ID NO 29
<211> LENGTH: 149
<212> TYPE: RNA
<213> ORGANISM: Homo sapiens

<400> SEQUENCE: 29
caucaagacc cagcugaguc acugucacug ccuaccaauc ucgaccggac cucgaccggc  60
ucgucugugu ugccaaucga cucggcgugg cgucggucgu gguagauagg cggucaugca 120
uacgaauuuu cagcucuugu ucggugac                                   149

<210> SEQ ID NO 30
<211> LENGTH: 23
<212> TYPE: RNA
<213> ORGANISM: Homo sapiens

<400> SEQUENCE: 30
caaagugcuu acagugcagg uag                                         23

<210> SEQ ID NO 31
<211> LENGTH: 22
<212> TYPE: RNA
<213> ORGANISM: Homo sapiens

<400> SEQUENCE: 31
ccgcacugug gguacuugcu gc                                          22

<210> SEQ ID NO 32
<211> LENGTH: 84
<212> TYPE: RNA
<213> ORGANISM: Homo sapiens

<400> SEQUENCE: 32
gucagaauaa ugucaaagug cuuacagugc agguagugau augugcaucu acugcaguga  60
aggcacuugu agcauuaugg ugac                                        84

<210> SEQ ID NO 33
<211> LENGTH: 87
<212> TYPE: RNA
<213> ORGANISM: Homo sapiens

<400> SEQUENCE: 33
gacagugcag ucacccauaa aguagaaagc acuacuaaca gcacuggagg guguagguu   60 uccuacuuua uggaugagug uacgug                                      87

<210> SEQ ID NO 34
<211> LENGTH: 81
<212> TYPE: RNA
<213> ORGANISM: Homo sapiens
```

```
<400> SEQUENCE: 34
ccuuggccau guaaaagugc uuacagugca gguagcuuuu ugagaucuac ugcaauguaa        60
gcacuucuua cauuaccaug g                                                 81

<210> SEQ ID NO 35
<211> LENGTH: 23
<212> TYPE: RNA
<213> ORGANISM: Homo sapiens

<400> SEQUENCE: 35
aaaagugcuu acagugcagg uag                                               23

<210> SEQ ID NO 36
<211> LENGTH: 80
<212> TYPE: RNA
<213> ORGANISM: Homo sapiens

<400> SEQUENCE: 36
ccuguugcca caaacccgua gauccgaacu uguggauua guccgcacaa gcuuguaucu        60
auagguaugu gucuguuagg                                                   80

<210> SEQ ID NO 37
<211> LENGTH: 21
<212> TYPE: RNA
<213> ORGANISM: Homo sapiens

<400> SEQUENCE: 37
cauaaaguag aaagcacuac u                                                 21

<210> SEQ ID NO 38
<211> LENGTH: 22
<212> TYPE: RNA
<213> ORGANISM: Homo sapiens

<400> SEQUENCE: 38
aacccguaga uccgaacuug ug                                                22

<210> SEQ ID NO 39
<211> LENGTH: 22
<212> TYPE: RNA
<213> ORGANISM: Homo sapiens

<400> SEQUENCE: 39
ggauaucauc auauacugua ag                                                22

<210> SEQ ID NO 40
<211> LENGTH: 82
<212> TYPE: RNA
<213> ORGANISM: Homo sapiens

<400> SEQUENCE: 40
ccugccgggg cuaaagugcu gacagugcag auaguggucc ucccgugcu accgcacugu        60 ggguacuugc ugcuccagca gg                                                82

<210> SEQ ID NO 41
<211> LENGTH: 75
<212> TYPE: RNA
<213> ORGANISM: Homo sapiens
```

```
<400> SEQUENCE: 41
agacagagaa gccaggucac gucucugcag uuacacagcu cacgagugcc ugcuggggug    60
gaaccugguc ugucu                                                    75

<210> SEQ ID NO 42
<211> LENGTH: 75
<212> TYPE: RNA
<213> ORGANISM: Homo sapiens

<400> SEQUENCE: 42
agacagagaa gccaggucac gucucugcag uuacacagcu cacgagugcc ugcuggggug    60
gaaccugguc ugucu                                                    75

<210> SEQ ID NO 43
<211> LENGTH: 84
<212> TYPE: RNA
<213> ORGANISM: Homo sapiens

<400> SEQUENCE: 43
uugguacuug gagagugguu aucccugucc uguucguuuu gcucaugucg aaucguacag    60
ggucauccac uuuuucagua ucaa                                          84

<210> SEQ ID NO 44
<211> LENGTH: 22
<212> TYPE: RNA
<213> ORGANISM: Homo sapiens

<400> SEQUENCE: 44
uccuguacug agcugcccg ag                                             22

<210> SEQ ID NO 45
<211> LENGTH: 22
<212> TYPE: RNA
<213> ORGANISM: Homo sapiens

<400> SEQUENCE: 45
ucguaccgug aguaauaaug cg                                            22

<210> SEQ ID NO 46
<211> LENGTH: 110
<212> TYPE: RNA
<213> ORGANISM: Homo sapiens

<400> SEQUENCE: 46
ccuggccucc ugcagugcca cgcuccgugu auuugacaag cugaguugga cacuccaugu    60
gguagagugu caguuuguca aauaccccaa gugcggcaca ugcuuaccag               110

<210> SEQ ID NO 47
<211> LENGTH: 22
<212> TYPE: RNA
<213> ORGANISM: Homo sapiens

<400> SEQUENCE: 47
ugucaguuug ucaaauaccc ca                                            22

<210> SEQ ID NO 48
<211> LENGTH: 85
<212> TYPE: RNA
<213> ORGANISM: Homo sapiens
```

<400> SEQUENCE: 48
cgcuggcgac gggacauuau uacuuuuggu acgcgcugug acacuucaaa cucguaccgu      60
gaguaauaau gcgccgucca cggca                                           85

<210> SEQ ID NO 49
<211> LENGTH: 21
<212> TYPE: RNA
<213> ORGANISM: Homo sapiens

<400> SEQUENCE: 49
cauuauuacu uuggurgc g                                                 21

<210> SEQ ID NO 50
<211> LENGTH: 86
<212> TYPE: RNA
<213> ORGANISM: Homo sapiens

<400> SEQUENCE: 50 gguggugu uucuccguuu gccuguuucg cugaugugca uucaacucau ucucagcaaa        60
auaagcaaau ggaaaauucg uccauc                                          86

<210> SEQ ID NO 51
<211> LENGTH: 86
<212> TYPE: RNA
<213> ORGANISM: Homo sapiens

<400> SEQUENCE: 51 gguggugu uucuccguuu gccuguuucg cugaugugca uucaacucau ucucagcaaa        60
auaagcaaau ggaaaauucg uccauc                                          86

<210> SEQ ID NO 52
<211> LENGTH: 21
<212> TYPE: RNA
<213> ORGANISM: Homo sapiens

<400> SEQUENCE: 52
uaguagaccg uauagcguac g                                               21

<210> SEQ ID NO 53
<211> LENGTH: 96
<212> TYPE: RNA
<213> ORGANISM: Homo sapiens

<400> SEQUENCE: 53
ugguacuugg agagauagua gaccguauag cguacgcuuu aucgugacg uauguaacac       60 gguccacuaa cccucaguau caaauccauc cccgag                               96

<210> SEQ ID NO 54
<211> LENGTH: 22
<212> TYPE: RNA
<213> ORGANISM: Homo sapiens

<400> SEQUENCE: 54
ccgcacugug gguacuugcu gc                                              22

<210> SEQ ID NO 55
<211> LENGTH: 84
<212> TYPE: RNA
<213> ORGANISM: Homo sapiens -continued

<400> SEQUENCE: 55
gucagaauaa ugucaaagug cuuacagugc agguagugau augugcaucu acugcaguga    60
aggcacuugu agcauuaugg ugac    84

<210> SEQ ID NO 56
<211> LENGTH: 87
<212> TYPE: RNA
<213> ORGANISM: Homo sapiens

<400> SEQUENCE: 56
gacagugcag ucacccauaa aguagaaagc acuacuaaca gcacuggagg guguaguguu    60
uccuacuuua uggaugagug uacugug    87

<210> SEQ ID NO 57
<211> LENGTH: 80
<212> TYPE: RNA
<213> ORGANISM: Homo sapiens

<400> SEQUENCE: 57
ccuguugcca caaacccgua gauccgaacu ugguauua guccgcacaa gcuuguaucu    60
auagguaugu gucuguuagg    80

<210> SEQ ID NO 58
<211> LENGTH: 21
<212> TYPE: RNA
<213> ORGANISM: Homo sapiens

<400> SEQUENCE: 58
cauaaaguag aaagcacuac u    21

<210> SEQ ID NO 59
<211> LENGTH: 22
<212> TYPE: RNA
<213> ORGANISM: Homo sapiens

<400> SEQUENCE: 59
aacccguaga uccgaacuug ug    22

<210> SEQ ID NO 60
<211> LENGTH: 22
<212> TYPE: RNA
<213> ORGANISM: Homo sapiens

<400> SEQUENCE: 60
uccuguacug agcugccccg ag    22

<210> SEQ ID NO 61
<211> LENGTH: 82
<212> TYPE: RNA
<213> ORGANISM: Homo sapiens

<400> SEQUENCE: 61
ccugccgggg cuaaagugcu gacagugcag auaguggucc ucuccgugcu accgcacugu    60
ggguacuugc ugcuccagca gg    82

<210> SEQ ID NO 62
<211> LENGTH: 84
<212> TYPE: RNA
<213> ORGANISM: Homo sapiens -continued

```
<400> SEQUENCE: 62
gucagaauaa ugucaaagug cuuacagugc agguagugau augugcaucu acugcaguga    60
aggcacuugu agcauuaugg ugac                                          84

<210> SEQ ID NO 63
<211> LENGTH: 90
<212> TYPE: RNA
<213> ORGANISM: Homo sapiens

<400> SEQUENCE: 63
aggccucgcu guucucuaug gcuuuuauu ccaugugau ucuacugcuc acucauauag      60
ggauuggagc cguggcgcac ggcggggaca                                    90

<210> SEQ ID NO 64
<211> LENGTH: 97
<212> TYPE: RNA
<213> ORGANISM: Homo sapiens

<400> SEQUENCE: 64
cacucugcug uggccuaugg cuuuucauuc cuaugugauu gcugucccaa acucauguag    60
ggcuaaaagc caugggcuac agugaggggc gagcucc                            97

<210> SEQ ID NO 65
<211> LENGTH: 77
<212> TYPE: RNA
<213> ORGANISM: Homo sapiens

<400> SEQUENCE: 65
guggccucgu ucaaguaauc caggauaggc ugugcagguc ccaaugggcc uauucuuggu    60
uacuugcacg gggacgc                                                  77

<210> SEQ ID NO 66
<211> LENGTH: 72
<212> TYPE: RNA
<213> ORGANISM: Homo sapiens

<400> SEQUENCE: 66
agauacugua aacauccuac acucucagcu guggaaagua agaaagcugg gagaaggcug    60
uuuacucuuu cu                                                       72

<210> SEQ ID NO 67
<211> LENGTH: 78
<212> TYPE: RNA
<213> ORGANISM: Homo sapiens

<400> SEQUENCE: 67
cuuucuacac agguugggau cgguugcaau gcuguguuuc uguauggau ugcacuuguc     60 ccggccuguu gaguuugg                                                 78

<210> SEQ ID NO 68
<211> LENGTH: 82
<212> TYPE: RNA
<213> ORGANISM: Rattus norvegicus

<400> SEQUENCE: 68
caaccuguga uacucaaacu gggggcucuu uuggguuuuc uuuggaagaa aagugccgcc    60
agguuuugag uguuaccgau ug                                            82
```

```
<210> SEQ ID NO 69
<211> LENGTH: 110
<212> TYPE: RNA
<213> ORGANISM: Homo sapiens

<400> SEQUENCE: 69
gagcugcuug ccuccccccg uuuuuggcaa ugguagaacu cacacuggug agguaacagg        60
auccgguggu ucuagacuug ccaacuaugg ggcgaggacu cagccggcac                   110

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
atgcggtttt ggcagtacat                                                    20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
gtcaatgggg tggagacttg                                                    20
```

EXOSOMES AND MIRNA TO TREAT GLAUCOMA

CROSS REFERENCE TO RELATED APPLICATIONS

This claims the benefit of U.S. Provisional Application No. 62/622,032, filed Jan. 25, 2018, which is incorporated herein by reference.

STATEMENT OF GOVERNMENT SUPPORT

This invention was made with Government support under project number Z01#: EY000318-20 by the National Institutes of Health, National Eye Institute. The Government has certain rights in the invention.

FIELD OF THE DISCLOSURE

This relates to the field of glaucoma, specifically methods for treating glaucoma using exosomes or a vector encoding a miRNA.

BACKGROUND

Glaucoma is one of the world's leading causes of irreversible blindness and is characterized by the slow progressive degeneration of retinal ganglion cells (RGC) and their axons (Tham et al., Ophthalmology 2014; 121:2081-2090). RGC operate as the final stage in the phototransductive visual pathway of the retina, tasked with the projection of electrochemical information to the brain along their axons which make up the optic nerve. RGC are irreplaceable, making their dysfunction and subsequent loss a severe detriment to vision and thus, quality of life. While current therapies can successfully reduce intraocular pressure (IOP), the critical risk factor associated with glaucoma, no neuroprotective strategies currently exist. Thus, a need remains for agents that can be used to treat glaucoma, and other diseases related to decreases in retinal ganglion cell survival.

SUMMARY OF THE DISCLOSURE

Methods are disclosed herein for treating glaucoma in a subject. In some embodiments, the methods increase retinal ganglion cell survival.

In some embodiments, the methods include selecting a subject with glaucoma, and locally administering to an eye of the subject a therapeutically effective amount of exosomes from mesenchymal stem cells.

In additional embodiments, the methods include selecting a subject with glaucoma, and locally administering to an eye of the subject a therapeutically effective amount of a vector comprising a nucleic acid molecule encoding a first miRNA. In some embodiments, the first miRNA is hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, hsa-miR-486-5p, hsa-miR-26a-1, hsa-miR-30c-2, hsa-miR-92a-1, rno-miR-292, or hsa-miR-182. In yet other embodiments, more than one nucleic acid encoding an miRNA is administered to the subject.

The foregoing and other features and advantages of the invention will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1B. Experimental design of study and exosome isolation. (A) Timeline and groupings of study, detailing the number of animals (eyes) per group, the two glaucoma models used and the exosome treatment schedule. (B) Nanosight analysis of extracellular vesicles isolated from BMSC, demonstrating their size and relative quantity.

FIGS. 2A-2B. IOP measurements in the two glaucoma models. (A) Mean IOP (mmHg) of healthy animals (green) and animals receiving ic injection of microbeads and ivit exosome treatments. (B) Mean IOP of healthy animals (green) and animals receiving laser photocoagulation of the trabecular meshwork/limbal vessels and ivit exosome treatments. Asterisks represent significant difference between intact and experimental groups (p<0.05).

FIGS. 3A-3E. Surviving RBPMS$^+$ RGC count. (A, B) Mean number of surviving RBPMS$^+$ RGC 56 days after ic microbead injection (A) or 21 days after laser photocoagulation (B). Counts were conducted in a 0.33 mm$^2$ region of retinal wholemounts, calculated as a composite average of 12 images taken at 1, 2 and 3 mm distances from the optic nerve head, 4 images per retinal petal (C; scale bar: 1 mm). Asterisks indicate significant difference from injured/untreated at p<0.05. (D) Representative images of RBPMS$^+$ RGC from immunohistochemically stained retinal wholemounts (scale bar: 250 µm). (E) Mean number of surviving RBPMS$^+$ RGC 3 days after purification and culture.

FIGS. 4A-4C. RNFL thickness measurements of rats. (A) Mean RNFL thickness (µm) of rats measured by OCT in animals 21 days after laser photocoagulation. Asterisks indicate significant difference from injured/untreated at p<0.05. (B) RNFL measurements were taken from around the optic nerve head (green circle; scale bar: 1 mm). (C) Representative OCT images of retina from which the RNFL (partially marked in red) measurements were taken (scale bar: 200 µm).

FIGS. 10A-10H. Effects of exosome treatment on RGC neuroprotection and neuritogenesis. The number of RGC (A), number of RGC bearing neurites (B) and the length of the longest neurite (C) in heterogeneous retinal cultures after treatment with different quantities of EV, before (exosomes+microvesicles) and after (exosomes) filtration. Black lines indicate significant difference between groups whereas asterisks indicate significant difference between filtered and unfiltered exosomes ($p<0.05$). Representative images of heterogeneous retinal cultures either untreated (D) or treated with BMSC (E), $3\times10^9$ BMSC exosomes with microvesicles (F), $7.5\times10^{10}$ BMSC exosomes with microvesicles (G) or $7.5\times10^{10}$ BMSC exosomes (H). All images are representative of the entire culture, nine separate culture wells/treatment, with every 3 wells using a different animal (scale bars: 50 μm). Sections were stained for βIII-tubulin (green) and DAPI (blue).

FIGS. 11A-11D. RNFL thickness of rats after ONC and exosome treatment. (A) Graph depicting the mean RNFL thickness (μm) of rats before and 21 days after ONC. Black lines indicate significant difference between groups whereas asterisks indicate significant difference from the same group pre-ONC ($p<0.05$). (B) Western blot demonstrating successful knockdown of Ago2 in BMSC treated with siAgo2 in comparison to BMSC treated with control siScr. (C) RNFL measurements were done from a section of retina surrounding the optic nerve head (green line). (D) Representative images of retina from Group 1, 2, 3 and 6, as measured by OCT (scale bars: 200 μm).

FIGS. 12A-12C. Brn3a⁺ and RBPMS⁺ RGC counts in exosome treated retina after ONC. (A) Graph depicting the mean number of Brn3a⁺ and RBPMS⁺ RGC in a 1 mm region of retina either side of the optic nerve head. Percentage of surviving RGC in comparison to intact controls is given above each group. Asterisks indicate a significant difference from intact, ONC+BMSC Exosomes and ONC+SiScr Exosomes groups ($p<0.05$). (B) Image of retina immunohistochemically stained for RBPMS (red) from animals injected with ExoGreen labelled exosomes (green). (C) Representative images of retina from Group 1-6, immunohistochemically stained for Brn3a (green) and RBPMS (red). All images show tissue counterstained with the nuclear marker DAPI (blue; scale bars: 50 μm).

FIGS. 14A-14B. GAP-43⁺ RGC axon counts in the optic nerve after ONC. (A) Graph depicting the mean number of GAP-43⁺ RGC axons in the optic nerve at 100-1200 μm from the laminin⁺ crush site. Asterisks indicate significant difference between ONC/ONC+fibroblast exosomes and ONC+BMSC exosomes/SiScr exosomes ($p<0.05$). (B) Representative images of optic nerves immunohistochemically stained for GAP-43 (green) and laminin (red) from groups 3 and 4 (scale bars: 100 μm).

FIGS. 17A-17B. ERG measurements of pSTR in DBA/2J mice. (A) Mean (±SEM) amplitude (μV) of pSTR measured by ERG at 3- (untreated healthy baseline), 6-, 9- and 12-month-old DBA/2J mice with or without ivit injection of BMSC- or fibroblast-derived sEV. Asterisk indicates significant difference between BMSC-derived sEV treated mice and fibroblast-derived sEV treated/untreated mice ($p<0.05$). (B) Representative traces of pSTR, arrows indicate the peak amplitude that was measured.

FIGS. 19A-19E. RNFL thickness after ONC. Graph depicting the average RNFL thickness (μm) of animals before (dashed grey line), and 21 days after ONC (A). Asterisks indicate significant differences ($p<0.05$) from PBS and virus (GFP) control treated animals. To encapsulate the entirety of the RNFL as it courses towards the optic nerve head, measurements were recorded at this region (B; scale bar 1 mm) and representative images from the 5 animals per group are shown (C, D and E; scale bars 200 μm).

FIGS. 20A-20B. RBPMS⁺ RGC counts after ONC. Graph depicting the number of RBPMS⁺ RGC (per mm or retina) 21 days after ONC (A). Asterisks indicate significant differences ($p<0.05$) from PBS and virus (GFP) control treated animals. Representative images of the ganglion cell layer of retina stained for RBPMS (green) and DAPI (blue) from the 5 animals per groups are shown (B; scale bar 100 μm)

FIG. 24A-24D. Effects of virally delivered miRNA on RGC neuroprotection/neuritogenesis in culture. The number of surviving βIII-tubulin$^+$ RGC (A) and the average length of their longest neurite (B) in heterogeneous adult rat retinal cultures treated with different viruses are shown. No significant differences between virus treated and virus (GFP) treated groups was seen. Representative images of retinal cultures treated with virus E (C) or PBS (D) are shown. Images are representative of the 3 separate cultures/3 repeats per culture. Sections were stained with βIII-tubulin (red; scale bar: 100 µm).

SEQUENCE LISTING

Figure 2A:
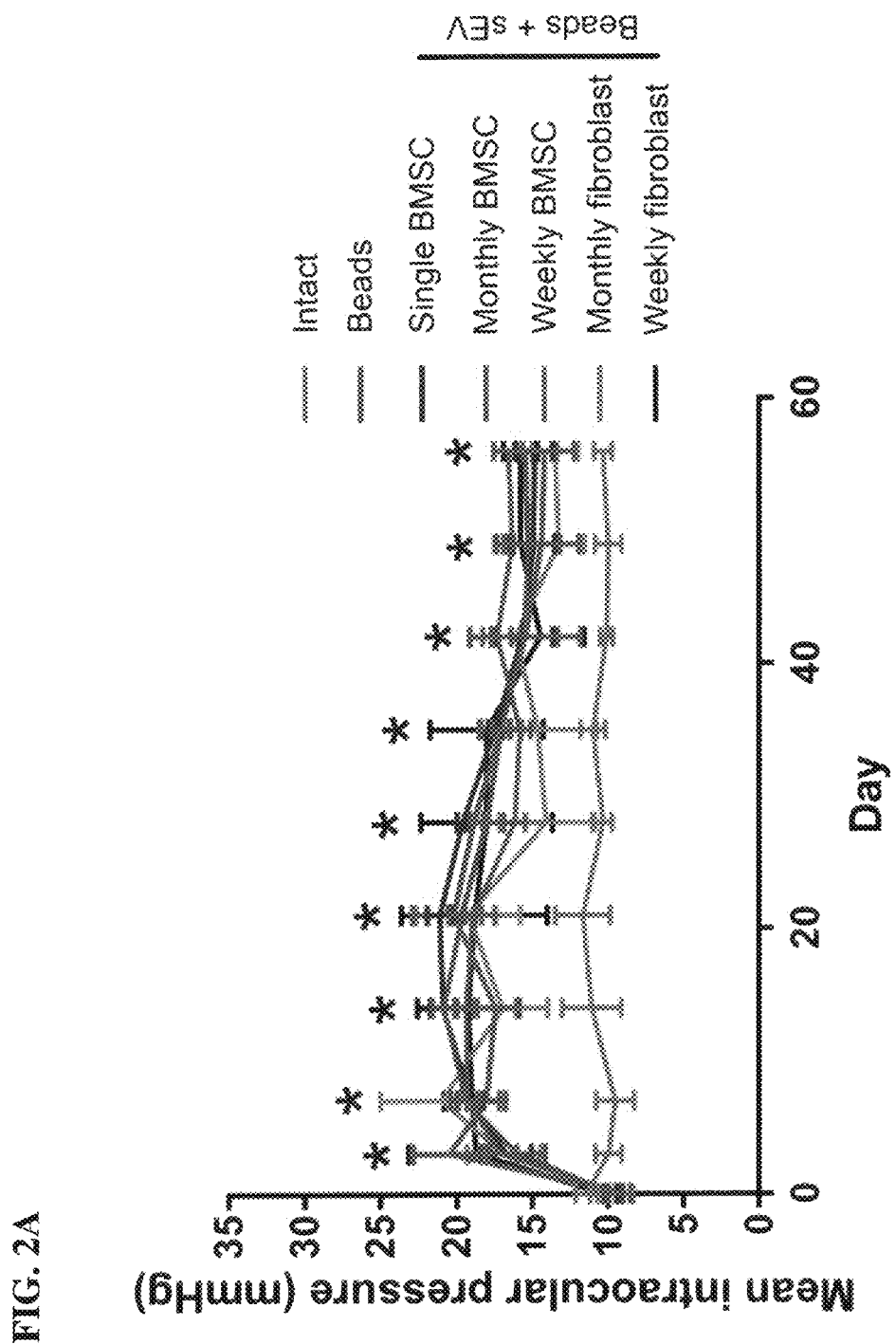

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-100047-02_ Sequence_Listing, Jan. 22, 2019, 13.5 KB], which is incorporated by reference herein. In the accompanying sequence listing:

SEQ ID NO: 1-69 are miRNA sequences.
SEQ ID NOS: 70 AND 71 are primer sequences.

DETAILED DESCRIPTION OF SEVERAL EMBODIMENTS

Mesenchymal stem cells (MSC) are a multipotent stromal cell residing in mesenchymal tissues such as bone marrow (BMSC) (Friedstein et al., *Cell Tissue Kin* 1970; 3:393-403), adipose (ADSC) (Zuk et al., *Tissue Eng* 2001; 7:211-228), umbilical blood (UCB-MSC) (Erices et al., *Brit J Haematol* 2000; 109:235-242) and dental pulp (Gronthos et al., *Proc Natl Acad Sci USA* 2000; 97:13625-13630). Their neuroprotective efficacy in retinal injury models has been demonstrated (see, for example, Mead et al., *Invest Ophthalmol Vis Sci* 2013; 54:7544-7556; Mead et al., *Cytotherapy* 2016; 18:487-496) and are currently undergoing clinical trials for retinal degenerative diseases such as glaucoma (Mead et al., *Stem Cell Res* 2015; 14:243-257). The mechanism of action is exclusively paracrine, through the secretion of neuroprotective factors as opposed to RGC replacement. MSC secrete a large abundance of factors, of which several neuroprotective candidates have been identified including BDNF and PDGF (Mead et al., *Plos One* 2014; 9:e109305; Jonson et al., *Brain* 2014; 137:503-519).

Exosomes are small 30-120 nm extracellular vesicles described decades ago as being secreted from most cell types both by outward budding of the plasma membrane as well as intracellular formation within multivesicular endosomes before secretion into the extracellular space[15]. The formation of the vesicle as well as the loading of cargo is reliant on a complex of 30 proteins referred to as Endosomal Sorting Complex Required For Transport (ESCRT). Exosomes contain mRNA, miRNA and protein and can be easily isolated from various bodily fluids as well as conditioned medium in vitro (Columbo et al., *Annu Rev Cell Dev Bi* 2014; 30:255-289; Thery et al., *Curr Protoc Cell Biol* 2006; Chapter 3: Unit 3 22). Originally thought to be a mechanism solely for the removal of waste, exosomes have now been demonstrated to deliver their cargo to nearby cells that translate the mRNA into proteins, as well as have gene expression downregulated by the exosome-derived miRNA (Valadi et al., *Nat Cell Biol* 2007; 9:654-U672). Therefore, irrespective of the receptors a recipient cell expresses, gene expression can be regulated by exosome-mediated cell-to-cell communication.

miRNA are small RNA molecules that are processed and incorporated into the RNA-induced silencing complex (RISC) composed of Dicer, TRBP and Argonaute2 (Ago2), its catalytic center (Gergory et al., *Cell* 2005; 123:631-640). Binding of the miRNA to the 3' untranslated region of mRNA allows repression of translation and a single miRNA can repress the translation of several hundred mRNA. Ago2 is integral to miRNA function as well as to the packaging of miRNA into exosomes (Lv et al., *Plos One* 2014; 9:e103599). Interestingly, the function of exosomal miRNA is dependent on Ago2 derived from the origin cell/exosome, Ago2 expressed in the recipient cell is not involved in the exosomal-derived miRNA function. Therefore, knockdown of Ago2 in host cells allows the isolation and testing of miRNA-depleted exosomes (Zhang et al., *Mol Neurobiol* 2016; 54:2659-2673; Mead et al., *STEM CELLS Transl Med* 2017; 6:1273-1285).

It is disclosed herein that exosomes and specific miRNAs can be used to increase retinal ganglion survival in a subject, such as, but not limited to, as subject with glaucoma.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 16, 2015. All references, patent applications and publications, and GENBANK® Accession numbers cited herein are incorporated by reference. In order to facilitate review of the various embodiments of the disclosure, the following explanations of specific terms are provided:

Adeno-associated Virus (AAV): AAV is a small virus that infects humans and some other primate species. AAV is not currently known to cause disease and consequently the virus causes a very mild immune response. AAV can infect both dividing and non-dividing cells and may incorporate its genome into that of the host cell. The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Animal: Living multi-cellular vertebrate organisms, a category that includes, for example, mammals and birds. The term mammal includes both human and non-human mammals. Similarly, the term "subject" includes both human and veterinary subjects.

Exosomes: Small (30-120 nm) endosome-derived membrane vesicles. Exosomes are enriched in miRNAs as well as mRNA and protein. Exosomes are produced by all cells including mesenchymal stem cells (MSC), such as bone marrow MSC, and their cargo varies depending on their cellular source. Exosomes can express CD11 and CD63, and thus can be CD11c$^+$ and CD63$^+$.

Glaucoma: An eye disorder characterized by retinal ganglion cell death, excavation of the optic nerve head and gradual loss of the visual field. An abnormally high intraocular pressure is commonly known to be detrimental to the eye and is one of the main risk factors in glaucoma. In glaucoma patients, high intraocular pressure can result in degenerative changes in the retina. "Ocular hypertension" refers to clinical situation in individuals with an abnormally high intraocular pressure without any manifestation of defects in the visual field or optic nerve head. Individuals with ocular hypertension carry the risk of conversion to glaucoma with the risk being correlated to higher intraocular pressure measurements.

Glaucoma can be divided into open-angle form and the closed-angle forms and further classified into acute and chronic forms. There also is a normal-tension glaucoma. The glaucoma can be a primary or a secondary glaucoma. More than 80% of all glaucoma cases are chronic open angle glaucoma (COAG), also called primary open angle glaucoma. Any of these forms of glaucoma can be treated using the methods disclosed herein.

"Primary angle closure glaucoma" is caused by contact between the iris, trabecular meshwork, and peripheral cornea which in turn obstructs outflow of the aqueous humor from the eye. This contact between iris and trabecular meshwork (TM) may gradually damage the function of the meshwork until it fails to keep pace with aqueous production, and the pressure rises. In over half of all cases, prolonged contact between iris and TM causes the formation of synechiae (effectively "scars"). These cause permanent obstruction of aqueous outflow. In some cases, pressure may rapidly build up in the eye, causing pain and redness (symptomatic, or so-called "acute" angle closure). In this situation, the vision may become blurred, and halos may be seen around bright lights. Accompanying symptoms may include a headache and vomiting. Diagnosis can made from physical signs and symptoms: pupils mid-dilated and unresponsive to light, cornea edematous (cloudy), reduced vision, redness, and pain. However, the majority of cases are asymptomatic. Prior to the very severe loss of vision, these cases can only be identified by examination, generally by an eye care professional.

"Primary open-angle glaucoma" occurs when optic nerve damage results in a progressive loss of the visual field. Not all people with primary open-angle glaucoma have eye pressure that is elevated beyond normal. The increased pressure is caused by the blockage of the aqueous humor outflow pathway. Because the microscopic passageways are blocked, the pressure builds up in the eye and causes imperceptible very gradual vision loss. Peripheral vision is affected first, but eventually the entire vision will be lost if not treated. Diagnosis can be made by looking for cupping of the optic nerve and measuring visual field. Prostaglandin agonists work by opening uveoscleral passageways.

Other forms of glaucoma are developmental glaucoma and secondary glaucoma, which can occur after uveitis, iridocyclitis, intraocular hemorrhage, trauma, or an intraocular tumor. Any form of glaucoma can be treated using the methods disclosed herein.

The death of retinal ganglion cells occurs in glaucoma. Methods are disclosed herein for increasing the survival of retinal ganglion cells.

Intraocular administration: Administering agents directly into the eye, for example by delivery into the vitreous or anterior chamber. Indirect intraocular delivery (for example by diffusion through the cornea) is not direct administration into the eye.

Intraocular Pressure: The pressure of the fluid that fills the eye globe, the aqueous humor, which is determined by the interplay between the rate of aqueous humor production inside the eye and the resistance to aqueous outflow as it exits the eye through the anterior chamber angle towards Schlemm's canal. In the human eye, the rate of aqueous formation is 2.54/minute while that in the rabbit eye is approximately 3 to 4 µL/minute. Normal IOP measurements in the human eye, according to widely acceptable consensus, range between 10 and 20 mm of mercury, with an average of 15.5 mm.

Intravitreal administration: Administering agents into the vitreous cavity. The vitreous cavity is the space that occupies most of the volume of the core of the eye with the lens and its suspension system (the zonules) as its anterior border and the retina and its coating as the peripheral border. Intravitreal administration can be accomplished by injection, pumping, or by implants.

Isolated: An "isolated" biological component (such as a nucleic acid molecule, miRNA, protein, or exosome) has been substantially separated or purified away from other biological components in the cell, blood or tissue of the organism, or the organism itself, in which the component naturally occurs, such as other chromosomal and extrachromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins. In some embodiments, isolated exosomes are separated from microvesicles.

Mesenchymal Stem Cells (MSC): A multipotent stem cell capable of giving rise to differentiated cells in multiple mesenchymal lineages, specifically to osteoblasts, adipocytes, myoblasts, and chondrocytes. Generally, MSCs also have one or more of the following properties: an ability to undergo asynchronous, or asymmetric replication (where the two daughter cells after division can have different phenotypes); extensive self-renewal capacity; and clonal regeneration of the tissue in which they exist, for example, the non-hematopoietic cells of bone marrow. A cell can be classified as an MSC if it shows plastic adherent properties under normal culture conditions and has a fibroblast-like morphology, and can undergo osteogenic, adipogenic and chondrogenic differentiation ex-vivo. Bone marrow MSC are present in the bone marrow in vivo.

MSCs can be cryopreserved. Due to their cellular origin and phenotype, these cells do not provoke an adverse immune response, allowing for the development of products derived from unrelated donors. MSC, such as BMSC, are known to secrete exosomes.

microRNA (miRNA): Single-stranded, small non-coding RNA molecules that regulate gene expression. miRNAs are generally about 16-27 or 19-22 nucleotides in length. miRNAs typically modulate gene expression by promoting cleavage of target mRNAs or by blocking translation of the cellular transcript.

miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression.

miRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR**, which are sometimes identified by their "3p" or "5p" annotation, see below.

One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

A nomenclature scheme has been well established for microRNAs (Griffiths-Jones et al., *Nucleic Acids Res.* 34:D140-D144, 2006; Ambros et al., *RNA* 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "150," resulting in a complete name of "hsa-miR-150." Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-181a and miR-181b). In some cases, mature miRNAs from both the 5' and 3' arms of the hairpin precursor are identified, which are designated "3p" or "5p" (such as miR-768-3p and miR-768-5p).

In the context of the present disclosure, administering a "miR" to a subject or contacting a cell with a "miR" encompasses administration or contacting with a pri-miRNA, pre-miRNA or mature miRNA, or a nucleic acid molecule encoding a pri-miRNA, pre-miRNA or mature miRNA.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating an agent, such as an exosome, a miRNA, or nucleic acid encoding a miRNA, in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term "purified" does not require absolute purity; rather, it is intended as a relative term. Thus, for example, a purified nucleic acid molecule preparation is one in which the nucleic referred to is more pure than the nucleic in its natural environment within a cell. For example, a preparation of a nucleic acid is purified such that the nucleic acid represents at least 50% of the total protein content of the preparation. Similarly, a purified exosome preparation is one in which the exosome is more pure than in an environment including cells, wherein there are microvesicles and exosomes. A purified population of nucleic acids or exosomes is greater than about 90%, 91%, 92%, 93%, 94%, 95%, 96%, 97%, 98%, 99% or 100% pure, or free other nucleic acids or cellular components, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a FGF polypeptide will possess a relatively high degree of sequence identity when aligned using standard methods.

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul, et al., *Nature Genet.*, 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, sequence identity counted over the full length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Therapeutically effective amount: A quantity of a specified composition, pharmaceutical or therapeutic agent (such as a miR, nucleic acid molecule encoding a miR, or exosome) sufficient to achieve a desired effect in a subject being treated with the agent. The effective amount of the agent will be dependent on several factors, including, but not limited to the subject being treated, the disease or condition being treated, and the manner of administration of the therapeutic composition. In some embodiments of the present disclosure, the therapeutically effective amount (or effective amount) of a miR is the amount required to treat glaucoma and/or increase retinal ganglion cell survival.

Transgene: An exogenous gene.

Transduce, transform or transfect: To introduce a nucleic acid molecule into a cell, such as a miR or a vector encoding a miR. These terms encompass all techniques by which a nucleic acid molecule can be introduced into a cell, including but not limited to, transduction with viral vectors, transfection with plasmid vectors, liposomal-mediated transfection and introduction of naked DNA by electroporation and particle gun acceleration. A transfected or transformed cell is a cell into which has been introduced a nucleic acid molecule by molecular biology techniques. In some examples, the nucleic acid molecule becomes stably replicated by the cell, for example by incorporation of the nucleic acid molecule into the cellular genome, or by episomal replication. In other examples, the nucleic acid molecule is transiently expressed in the cell.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Virus: Microscopic infectious organism that reproduces inside living cells. A virus consists essentially of a core of a single nucleic acid surrounded by a protein coat and has the ability to replicate only inside a living cell. "Viral replication" is the production of additional virus by the occurrence of at least one viral life cycle. Viral vectors are known in the art, and include, for example, adenovirus, AAV, lentivirus and herpes virus.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. "About" indicates within 5%, unless otherwise specified. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Treating Glaucoma

Methods are disclosed herein for treating a subject with glaucoma. The subject can have open angle glaucoma, closed angle glaucoma, or normotensive glaucoma. The glaucoma can be a primary glaucoma or a secondary glaucoma. Any of these subjects can be selected for treatment. The subject can be a veterinary subject or a human. The subject can be a mammal. The subject can be avian or a domestic pet, such as a cat, dog or rabbit. The subject can be a non-human, primate, or livestock, including wine, ruminants, horses, and poultry.

Intraocular pressure (IOP), the fluid pressure within the eye, can be measured in units of millimeters of mercury (mmHg) or kilopascals (kPa). Normal intraocular pressure is typically considered to be between 10 mmHg and 20 mmHg. The average value of intraocular pressure is 15.5 mmHg with fluctuations of about 2.75-3.50 mmHg. Elevated intraocular pressure (above 21 mmHg or 2.8 kPa) is the most important and only modifiable risk factor for glaucoma. In some embodiments a subject is selected that has elevated intraocular pressure. In other embodiments a subject is selected who has less than elevated intraocular pressure, but who has evidence of glaucomatous damage. For example, the subject may have cupping of the optic disc and an increased or increasing cup-to-disk ratio (for example greater than 0.3, 0.5 or 0.7). In other embodiments the subject may have a slightly elevated IOP in the presence of glaucomatous optic nerve damage (such as a progression in the cup-to-disc ratio).

Testing for glaucoma can include measurements of the intraocular pressure, such as using tonometry, anterior chamber angle examination or gonioscopy, and examination of the optic nerve to identify damage, change in the cup-to-disc ratio, rim appearance and detection of vascular changes. Visual field testing can be performed. The retinal nerve fiber layer can be assessed with imaging techniques such as optical coherence tomography, scanning laser polarimetry, and/or scanning laser ophthalmoscopy (Heidelberg retinal tomogram). Additional tests include tonometry, ophthalmoscopy, perimetry, gonioscopy, pachymetry, and nerve fiber analysis. These methods can be performed in order to select a subject for treatment according to the methods disclosed herein.

In some embodiments, the disclosed methods include selecting a subject with glaucoma, and administering to the subject a therapeutically effective amount of exosomes from mesenchymal stem cells, such as bone marrow stem cells. In more embodiments, the disclosed methods include selecting a subject with glaucoma, and administering to the subject a therapeutically effective amount of at least one miRNA, or a nucleic acid encoding the at least one miRNA, as described in detail below.

In some embodiments, the disclosed methods include selecting a subject with glaucoma, and administering to the subject a therapeutically effective amount of exosomes and/or a miRNA and/or a nucleic acid encoding at least one miRNA locally to the eye. Administration can be to the vitreous of the eye. In some embodiments, administration of the vitreous of the eye is accomplished using intravitreal injection, pumps or implants. In other embodiments, administration can be systemic. Additional exemplary routes of administration include, but are not limited to, intravenous, intraperitoneal, or subcutaneous administration.

A therapeutically effective amount of any of the disclosed therapeutic agents can be suspended in a pharmaceutically acceptable carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. Other agents can be added to the compositions, such as preservatives and anti-bacterial agents. These compositions can be administered locally to the eye, such as by intravitreously or subretinally. In other embodiments, administration can be systemic. Additional exemplary routes of administration include, but are not limited to, intravenous, intraperitoneal, or subcutaneous administration.

In some embodiments, a therapeutically effective amount of an agent disclosed herein is administered by intraocular, for example intravitreal, injection. A general method for intravitreal injection may be illustrated by the following brief outline. This example is merely meant to illustrate certain features of the method, and is in no way meant to be limiting. Procedures for intravitreal injection are known in the art (see, for example Peyman, et al. (2009) Retina 29(7):875-912 and Fagan and Al-Qureshi, (2013) Clin. Experiment. Ophthalmol. 41(5):500-7). Other methods of intraocular administration are known in the art, and include subretinal administration.

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as povidone-iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site. During injection, the needle can be inserted perpendicular to the sclera and pointed to the center of the eye. The needle can be inserted such that the tip ends in the vitreous, rather than the subretinal space. Any suitable volume known in the art for injection may be used. After injection, the eye can be treated with a sterilizing agent such as an antibiotic. The eye can also be rinsed to remove excess sterilizing agent.

Intravitreal injection of a therapeutic agents (for example, exosomes, one or more miRNAs, a nucleic acid encoding a miRNA, or a vector) can be performed once, or can be performed repeatedly, such as 1, 2, 3, 4, 5, 6, 7, 8, 9, or 10 times. Administration can be performed biweekly, weekly, every other week, monthly, or every 2, 3, 4, 5, or 6 months.

Pharmaceutical compositions that include exosomes, a miRNA, and/or a nucleic acid encoding a miRNA, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In some embodiments, the disclosed methods increase the survival of retinal ganglion cells when administered to the eye of a subject with glaucoma.

The subject can be administered additional therapeutic agents. These include, but are not limited to, an agent that lowers intraocular pressure. The agent can be a) a prostaglandin analog, b) a beta-adrenergic blocker, c) an alpha-adrenergic agonist, or d) a cholinergic agonist. Exemplary agents include latanoprost, bimatorpost, travoprost, timolol, betaxolol, brimonidine, pilocarpine, dorzolamide, brinzolamide, and acetazolamide. In some specific non-limiting examples, the agent is a) latanoprost, b) timolol, c) brimonidine, or d) pilocarpine. The subject can be administered a Rho-kinase inhibitor, such as, but not limited to, ripasudil or netarsudil.

Additional agents that can be administered to the subject include antibacterial and antifungal antibiotics, as well as non-steroidal anti-inflammatory agents to reduce risk of infection and inflammation. Additional agents can be administered by any route. The additional agents can be formulated separately, or in the same composition as one or more miRNAs and/or exosomes.

Agents of use include minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefininox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol).

Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, saperconazole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be used such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, fluclorinide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lornoxicam, piroxicam, tenoxicam), .epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Implants are also of use in the methods disclosed herein. The implants can be inserted into the eye by a variety of methods, including placement by forceps or by trocar following making an incision in the sclera (for example, a 2-3 mm incision) or other suitable sites. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of the therapeutic agent surrounding the device, and thus influence the release rates (for example, a device placed closer to the edge of the vitreous may result in a slower release rate, see U.S. Pat. Nos. 5,869,079 and 6,699,493). In one embodiment, an implant is formulated with a bioerodible polymer matrix.

Generally, when implants are used, the therapeutic agent is homogeneously distributed through the polymeric matrix, such that it is distributed evenly enough that no detrimental fluctuations in rate of release occur because of uneven distribution of the immunosuppressive agent in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493).

Following administration, the subject can be evaluated for response using any methods known in the art. These include, but are not limited to, ophthalomosccopy, perimetry, gonioscopy, pachymetry, or nerve fiber analysis. In some embodiments, retinal ganglion cell number and/or viability can be assessed. One of skill in the art can readily determine that the disclosed methods are effective. For example it can be determined by whether the cup-to-disc ratio has stabilized. Scanning laser polarimetry or optical coherence tomography could be used, for example to perform retinal nerve fiber layer analysis. A visual field test could be used to monitor progression of glaucoma. For any of the disclosed methods, therapeutic efficacy in treating a vision deficiency can as an alteration in the individual's vision.

Exosomes

Exosomes are small vesicles that originate in eukaryotic cells, primarily from the endosomal pathway. Exosomes are bound by a plasma membrane and are released from cells into the extracellular environment; exosomes are approximately 30-120 nM in diameter. Naturally occurring exosomes are hypothesized to transport molecules from one cell to another. Exosomes are taken up by recipient cells by endocytosis or by fusion of the exosomal membrane with the plasma membrane of the recipient cell.

In some embodiments, the exosomes are from mesenchymal stem cells. The mesenchymal stem cells can be, without limitation, derived from adipose tissue, umbilical cord blood, or bone marrow. In other embodiments, the exosomes can be derived from other mesenchymal stem cells, such as, but not limited to, dental pulp stem cells, see for example, PCT Publication No. 02/07679, U.S. Pat. No. 7,052,907, and Gronthos et al., *Proc Natl Acad Sci USA* 2000; 97:13625-13630, all incorporated by reference herein. In one specific non-limiting example, the stem cells are bone marrow stem cells (BMSC) derived exosomes.

In other embodiments, the exosomes are from neuronal precursor cells. These cells include, but are not limited to, neuronal precursor cells derived from induced pluripotent stem cells or ES cells. See Thomson et al., Science 282: 1145-1147, 1998 and Sluch et al., Stem Cells Transl Med. 6, 1972-1986, 2017, both incorporated herein by reference. In some non-limiting examples, the neuronal precursor can be neural crest cells.

Exosomes, such as mesenchymal stem cell-derived exosomes, for example, BMSC-derived exosomes, offer significant therapeutic benefit to the protection of RGCs, an effect mediated by their miRNA rather than protein content. Exosomes offer a cell-free alternative to BMSC therapy, and can be easily isolated, purified and stored. Exosomes lack the risk of complications associated with transplanting live cells into the vitreous (immune rejection, unwanted proliferation/differentiation).

In further embodiments, the mesenchymal stem cells can be treated with a priming agent that increases the release of exosomes from the mesenchymal stem cells. Priming agents include, but are not limited to, tumor necrosis factor (TNF)-α (see, for example, Wang et al., J Neuroinflammation. 2017; 14: 87, 2017, incorporated by reference herein). In other embodiments, the agent is a cytokine. In some embodiments, the agent increases glutaminase activity.

Exosomes can be isolated and/or purified from the conditioned media of cells, such as mesenchymal stem cells, such as bone marrow stem cells or dental pulp stem cells, grown in culture, or from biological fluids obtained from a subject. Stem cells, such as mesenchymal stem cells, bone marrow-derived mesenchymal stem cells, and dental pulp stem cells, produce exosomes. Exosomes used in the methods and compositions described herein can be derived from any of these cell types, or combinations thereof. In some embodiments, the mesenchymal stem cells are autologous to the subject treated by the disclosed methods. In other embodiments, the mesenchymal stem cells are allogenic. In some embodiments, the stem cells are the matched to the major histocompatibility complex (MHC) of the subject to be treated. The mesenchymal stem cells, such as bone marrow-derived mesenchymal stem cells, can be human. In some embodiments, the bone marrow-derived mesenchymal stem cells are $CD29^+/CD44^+/CD73^+/CD90^+/CD45^-$ bone marrow-derived mesenchymal stem cells. In further embodiments, the exosomes are $CD11c^+$ and $CD63^+$ exosomes.

Exosomes can be isolated from cells grown in culture or from biological fluids by any suitable method known in the art. For example, exosomes can be isolated using techniques including differential centrifugation, precipitation, gel-filtration, column binding, affinity purification, or combinations of these methods. By way of non-limiting example, exosomes can be purified by isolation from cells and other cellular components by differential centrifugation, whereby cell culture supernatants are centrifuged at low speeds (e.g., 20,000 g or less) to remove cells and cellular debris, followed by centrifugation at high speeds (e.g., 100,000 g or more) to pellet exosomes. This procedure can be used in conjunction with filtration (e.g., using filters of approximately 0.8 μm and/or 0.2 μm) to eliminate cell debris and other contaminants. In another example, exosomes can be purified using a density gradient, e.g., a sucrose density gradient, to isolate exosomes having an average density of approximately 1.13-2.21 g/mL. In an exemplary embodiment, exosomes can be purified by centrifugation at approximately 300 g to remove cells, followed by centrifugation at approximately 2000 g to remove dead cells, followed by centrifugation at approximately 10,000 g to remove cellular debris. The supernatant can be filtered using a filter of, for example, approximately 0.2 μm. The filtrate can then be centrifuged at 100,000 g to pellet exosomes. If desired, the pellet can be washed, and centrifuged again at 100,000 g to further purify the exosomes. Exemplary protocols for isolating exosomes are provided below.

Other methods of exosomal isolation are known in the art, see for example, Raposo et al. (1996), J. Exp. Med. 183: 1161-1172. An exemplary method for purifying exosomes from conditioned medium by ultrafiltration is disclosed in by Lamparski et al. (2002), J. Immunol. Methods 270:211-226. Additional exemplary methods of exosome purification are described by Thery et al., Current Protocols in Cell Biology (2006) 3.22.1-3.22.29. Methods for isolating exosomes also are disclosed in U.S. Pat. No. 9,671,321 and PCT Publication No. WO 2016/172598A1. These are all incorporated by reference herein.

Recent advances in nanoscale flow cytometry also permit the sorting and recovery of exosomes as in Scientific Reports 7:1878 (2017), which is incorporated by reference.

Kits are commercially available to facilitate purification of exosomes from a variety of source material. These include, for example, the EXO-SPIN™ kit (Cell Guidance Systems), the Total Exosome Isolation Kit from Life Technologies, the EXOQUICK™ kit from System Biosciences, and the EXO-FLOW™ kit from System Biosciences.

A therapeutically effective amount of exosomes are administered to subjects according to the disclosed methods. The dose may be determined according to various parameters, especially according to the severity of the condition, age, and weight of the patient to be treated; the route of administration; and the required regimen. A physician will be able to determine the required route of administration and dosage for any particular patient.

Optimum dosages may vary depending on the relative potency of individual constructs, and can generally be estimated based on $EC_{50}$s found to be effective in vitro and in in vivo animal models. In some embodiments, the exosomes are administered locally to the eye, such as intravitreously. The dose of exosomes administered, depending on the embodiment, ranges from about $1.0 \times 10^8$ to about $1.0 \times 10^{13}$ exosomes, such as $1.0 \times 10^8$ to about $1.0 \times 10^9$, about $1.0 \times 10^9$ to about $1.0 \times 10^{10}$, about $1.0 \times 10^{10}$ to about $1.0 \times 10^{11}$, about $1.0 \times 10^{11}$ to about $1.0 \times 10^{12}$, about $1.0 \times 10^{12}$ to about $1.0 \times 10^{13}$, and overlapping ranges thereof. In some embodiments, the exosomes are administered locally to the eye, such as via intravitreal administration. In a specific non-limiting example, the administration can be subretinal. In a further embodiment, administration can be systemic such as, but not limited to, intravenous administration. In additional embodiments, exosomes are administered in an amount about 10-fold to an amount of about 1,000,000-fold greater than the number of cells in the target tissue, including about 50-fold, about 100-fold, about 500-fold, about 1000-fold, about 10,000-fold, about 100,000-fold, about 500,000-fold, about 750,000-fold, and amounts in between these amounts.

In certain embodiments, the dosage is from 0.01 mg/kg to 100 mg per kg of body weight. For example, a dose can range from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. In some non-limiting examples, this dosage is administered systemically.

Different dosages may be administered depending on the route of administration. Administration can be local to the eye, such as via intravitreal administration. In another embodiment, the administration can be subretinal. In further embodiments, administration can be systemic. In a non-limiting example, administration is intravenous.

In an exemplary embodiment, for administration to the eye, such as intravitreal or subretinal administration, the dose of a single injection is in the range of about 1 to 20 μg. In another exemplary embodiment, the dose of single or multiple injections is in the range of 1 to 10 μg. Thus, a "therapeutically effective amount" will fall in a relatively broad range that can be determined through clinical trials.

In several embodiments, the exosomes are delivered in a single, bolus dose. In some embodiments, however, multiple doses of exosomes may be delivered. In certain embodiments, the patient is treated repeatedly, for example biweekly, weekly, bimonthly, monthly, every 2, 3, 4, 5 or 6 months or yearly. Treatment methods are disclosed above. Persons of ordinary skill in the art can easily estimate repetition rates for dosing based on measured residence times and concentrations of the construct in bodily fluids or tissues.

The exosomes can be used alone, or in combination with other agents. In some embodiments, the exosomes are utilized with a nucleic acid encoding a miRNA, as disclosed herein.

Vectors Encoding a miRNA miRNAs are single-stranded, small non-coding RNA molecules that regulate gene expression. Mature miRNAs are generally about 17-25 (such as 19-22) nucleotides in length. miRNAs typically modulate gene expression by promoting cleavage of target mRNAs or by blocking translation of the cellular transcript. miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression. miRNA sequences are publicly available. As disclosed herein. a miRNA nucleic acid includes precursor miRNAs, as well processed or mature miRNA nucleic acids. For example, a miRNA nucleic acid may be a pri-miRNA, a pre-miRNA, or a mature miRNA nucleic acid. One or more miRNAs can be utilized in the methods disclosed herein.

Exemplary mature miRNAs that can be used in the methods described herein are hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, and hsa-miR-486-5p. The miRNA can be one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p. The miRNA can also be hsa-miR-106b. In other embodiments the miRNA is hsa-miR-17, hsa-miR-135a, hsa-miR-135b. The miRNA can be hsa-miR-26a-1, hsa-miR-17, hsa-miR-30c-2, hsa-miR-92a-1, rno-miR-292, or hsa-miR-182.

Combinations of 2, 3, 4, 5, 6, 7, 8, 9 or 10 of these miRNAs are also of use. In some embodiments, 2, 3, 4 or 5 miRNAs are utilized. In some embodiments, nucleic acid molecules encoding one or more miRNAs are administered to the subject, such as combinations of 2, 3, 4, 5, 6, 7, 8, 9, or 10 of these miRNAs. These nucleic acid molecules can be administered in the same vector, or in different vectors. In some embodiments, 1, 2, 3, 4, 5, or all of hsa-miR-26a-1, hsa-miR-17, hsa-miR-30c-2, hsa-miR-92a-1, rno-miR-292, or hsa-miR-182 are used in the method.

Thus, in some embodiments, a nucleic acid molecule encoding a first miRNA is utilized wherein the first miRNA is hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p. The first miRNA can be one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p. In some embodiments, the first miRNA is hsa-miR-106b. In other embodiments the first miRNA is hsa-miR-17, hsa-miR-135a, hsa-miR-135b. In further embodiments, the first miRNA is hsa-miR-26a-1, hsa-miR-30c-2, hsa-miR-92a-1, rno-miR-292, or hsa-miR-182.

A nucleic acid encoding a first miRNA can be utilized with, or without, nucleic acids encoding additional miRNAs. In some non-limiting examples, the subject is administered nucleic acids encoding two, three, four or five different miRNAs. However, the subject can be administered a nucleic acid encoding the first miRNA, and no additional miRNAs (and/or nucleic acids encoding these miRNAs).

In further embodiments, a second miRNA is utilized, or a nucleic acid encoding the second miRNA. In some embodiments, the second miRNA is hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p, hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p. The second miRNA can be one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p. In some embodiments, the second miRNA is hsa-miR-106b. In other embodiments the second miRNA is hsa-miR-17, hsa-miR-135a, or hsa-miR-135b. In further embodiments, the second miRNA is hsa-miR-26a-1, hsa-miR-30c-2, hsa-miR-92a-1, rno-miR-292, or hsa-miR-182. Generally, the first miRNA and the second miRNA are different.

Similarly, a third miRNA, or a nucleic acid encoding the third miRNA, can be utilized, wherein the third miRNA is hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p. The third miRNA can be one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p. In some embodiments, the third miRNA is hsa-miR-106b. In other embodiments, the third miRNA is hsa-miR-17, hsa-miR-135a, or hsa-miR-135b. In further embodiments, the third miRNA is hsa-miR-26a-1, hsa-miR-30c-2, hsa-miR-92a-1, rno-miR-292, or hsa-miR-182. Generally the third miRNA is different from the first miRNA and the second miRNA. Additional miRNA(s), and/or nucleic acids encoding the additional miRNA(s) can also be administered to the subject.

In some embodiments, a first miRNA and a second miRNA, or a nucleic acid molecule encoding a first miRNA and a nucleic acid molecule encoding a second miRNA are utilized, wherein both of the first and second miRNA are one of hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p. Generally the first miRNA and the second miRNA are different. Optionally, a third miRNA, or a nucleic acid molecule encoding the third miRNA can be utilized, wherein the third miRNA can be one of hsa-miR- 126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p, and wherein the first, second and third miRNA are different. In further embodiments, all of the first miRNA, the second miRNA, and the third miRNA are utilized, wherein each of the first miRNA, second miRNA and third miRNA are one of hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-130'7-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p. Generally, the first miRNA, second miRNA, and third miRNA are different each from the other.

In some embodiments, a first and a second miRNA, or a nucleic acid molecule encoding the first miRNA and the second miRNA are utilized wherein each of the first miRNA and the second miRNA are one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p, and wherein the first and second miRNA are different. In more embodiments a first, a second miRNA, and a third miRNA, or a nucleic acid molecules encoding the first miRNA, the second miRNA and the third miRNA are utilized wherein each of the first miRNA, the second miRNA, and the third miRNA are one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p, and wherein the first miRNA, the second miRNA, and the third miRNA are different. In further embodiments, the first miRNA, the second miRNA and the third miRNA are one of hsa-miR-26a-1, hsa-miR-30c-2, hsa-miR-92a-1, rno-miR-292, or hsa-miR-182.

In further embodiments, a first and a second miRNA are utilized, or a nucleic acid encoding a first miRNA and a second miRNA are utilized, wherein the first miRNA is one of hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, hsa-miR-486-5p, hsa-miR-26a-1, hsa-miR-30c-2, hsa-miR-92a-1, rno-miR-292, or hsa-miR-182. Generally the first and the second miRNA are different. In further embodiments, a third miRNA, or a nucleic acid encoding a third miRNA, is utilized, wherein the third miRNA is a) one of hsa-miR-200b-3p, hsa-miR-142-3p, hsa-miR-379-3p, hsa-miR-136-5p, hsa-miR-1343, hsa-miR-615-5p, hsa-miR-1343, hsa-miR-150, hsa-miR-150-5p, hsa-miR-330-3p, hsa-miR-330, hsa-miR-223-5p, hsa-miR-126-3p, hsa-miR-223, hsa-miR-223-3p, hsa-miR-126, hsa-miR-126-5p, hsa-miR-483-5p, hsa-miR-487a, hsa-miR-342-3p, hsa-miR-1468, hsa-miR-1468, hsa-miR-425-5p, hsa-miR-335-3p, hsa-miR-1307-3p' hsa-miR-30e-3p, hsa-miR-411-5p, hsa-miR-411, hsa-miR-1307, hsa-miR-17-5p, hsa-miR-106b-3p, hsa-miR-17, hsa-miR-142, hsa-miR-106a, hsa-miR-106a-5p, hsa-miR-100, hsa-miR-142-5p, hsa-miR-100-5p, hsa-miR-144-5p, hsa-miR-106b, hsa-miR-370, hsa-miR-370, hsa-miR-487b, or hsa-miR-486-5p; b) one of hsa-miR-126-3p, hsa-miR-223, hsa-miR-223-3p, hsa-miR-126, hsa-miR-126-5p, hsa-miR-1468, hsa-miR-1468, hsa-miR-411-5p, hsa-miR-411, hsa-miR-106b-3p, hsa-miR-17, hsa-miR-142, hsa-miR-100, hsa-miR-142-5p, hsa-miR-100-5p, or hsa-miR-486-5p; or c) hsa-miR-106b. Generally the first miRNA, second miRNA and third miRNA are different.

In any of these methods, additional nucleic acids encoding miRNA can be utilized. Thus, the subject can be administered four, five or six different nucleic acids encoding the miRNA.

One of ordinary skill in the art can identify miRNA precursors, as well as processed or mature miRNAs, for example, utilizing publicly available databases. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

In some examples, the miRNA nucleic acids of use in the methods disclosed herein have a sequence at least 85% identical to the nucleic acid sequence of one of the mature miRNAs listed in Table 1 (SEQ ID NOs: 1-69). For example, the miRNA nucleic acid includes or consists of a nucleic acid sequence at least 85%, 86%, 87%, 88%, 89%, 90%, 91%, 92%, 93%, 94%, 95%, 96%, 97%, 98% or 99% identical to the nucleic acid sequence of one of the miRNAs listed in Table 1. Exemplary sequences can be obtained using computer programs that are readily available on the internet and the nucleic acid sequences set forth herein.

TABLE 1

| Human miRNA | Sequence | SEQ ID NO: |
| --- | --- | --- |
| hsa-miR-200b-3p | UAAUACUGCCUGGUAAUGAUGA | SEQ ID NO: 1 |
| hsa-miR-142-3p | UGUAGUGUUUCCUACUUUAUGGA | SEQ ID NO: 2 |

TABLE 1-continued

| Human miRNA | Sequence | SEQ ID NO: |
|---|---|---|
| hsa-miR-379-3p | UAUGUAACAUGGUCCACUAACU | SEQ ID NO: 3 |
| hsa-miR-136-5p | ACUCCAUUUGUUUUGAUGAUGGA | SEQ ID NO: 4 |
| hsa-miR-1343 | GCUGGCGUCGGUGCUGGGGAGCGGCCCCCGGGUG GGCCUCUGCUCUGGCCCCUCCUGGGGCCCGCACU CUCGCUCUGGGCCCGC | SEQ ID NO: 5 |
| hsa-miR-615-5p | GGGGGUCCCCGGUGCUCGGAUC | SEQ ID NO: 6 |
| hsa-miR-1343 | GCUGGCGUCGGUGCUGGGGAGCGGCCCCCGGGUG GGCCUCUGCUCUGGCCCCUCCUGGGGCCCGCACU CUCGCUCUGGGCCCGC | SEQ ID NO: 7 |
| hsa-miR-150 | CUCCCCAUGGCCCUGUCUCCCAACCCUUGUACCA GUGCUGGGCUCAGACCCUGGUACAGGCCUGGGGG ACAGGGACCUGGGGAC | SEQ ID NO: 8 |
| hsa-miR-150-5p | UCUCCCAACCCUUGUACCAGUG | SEQ ID NO: 9 |
| hsa-miR-330-3p | GCAAAGCACACGGCCUGCAGAGA | SEQ ID NO: 10 |
| hsa-miR-330 | CUUUGGCGAUCACUGCCUCUCUGGGCCUGUGUCU UAGGCUCUGCAAGAUCAACCGAGCAAAGCACACG GCCUGCAGAGAGGCAGCGCUCUGCCC | SEQ ID NO: 11 |
| hsa-miR-223-5p | CGUGUAUUUGACAAGCUGAGUU | SEQ ID NO: 12 |
| hsa-miR-126-3p | UCGUACCGUGAGUAAUAAUGCG | SEQ ID NO: 13 |
| hsa-miR-223 | CCUGGCCUCCUGCAGUGCCACGCUCCGUGUAUUU GACAAGCUGAGUUGGACACUCCAUGUGGUAGAGU GUCAGUUUGUCAAAUACCCCAAGUGCGGCACAUG CUUACCAG | SEQ ID NO: 14 |
| hsa-miR-223-3p | UGUCAGUUUGUCAAAUACCCCA | SEQ ID NO: 15 |
| hsa-miR-126 | CGCUGGCGACGGGACAUUAUUACUUUUGGUACGC GCUGUGACACUUCAAACUCGUACCGUGAGUAAUA AUGCGCCGUCCACGGCA | SEQ ID NO: 16 |
| hsa-miR-126-5p | CAUUAUUACUUUUGGUACGCG | SEQ ID NO: 17 |
| hsa-miR-483-5p | AAGACGGGAGGAAAGAAGGGAG | SEQ ID NO: 18 |
| hsa-miR-487a | GGUACUUGAAGAGUGGUUAUCCCUGCUGUGUUCG CUUAAUUUAUGACGAAUCAUACAGGGACAUCCAG UUUUUCAGUAUC | SEQ ID NO: 19 |
| hsa-miR-342-3p | UCUCACACAGAAAUCGCACCCGU | SEQ ID NO: 20 |
| hsa-miR-1468 | GGUGGGUGGUUUCUCCGUUUGCCUGUUUCGCUGA UGUGCAUUCAACUCAUUCUCAGCAAAAUAAGCAA AUGGAAAAUUCGUCCAUC | SEQ ID NO: 21 |
| hsa-miR-1468 | GGUGGGUGGUUUCUCCGUUUGCCUGUUUCGCUGA UGUGCAUUCAACUCAUUCUCAGCAAAAUAAGCAA AUGGAAAAUUCGUCCAUC | SEQ ID NO: 22 |
| hsa-miR-425-5p | AAUGACACGAUCACUCCCGUUGA | SEQ ID NO: 23 |
| hsa-miR-335-3p | UUUUUCAUUAUUGCUCCUGACC | SEQ ID NO: 24 |
| hsa-miR-1307-3p | ACUCGGCGUGGCGUCGGUCGUG | SEQ ID NO: 25 |
| hsa-miR-30e-3p | CUUUCAGUCGGAUGUUUACAGC | SEQ ID NO: 26 |
| hsa-miR-411-5p | UAGUAGACCGUAUAGCGUACG | SEQ ID NO: 27 |
| hsa-miR-411 | UGGUACUUGGAGAGAUAGUAGACCGUAUAGCGUA CGCUUUAUCUGUGACGUAUGUAACACGGUCCACU AACCCUCAGUAUCAAAUCCAUCCCCGAG | SEQ ID NO: 28 |
| hsa-miR-1307 | CAUCAAGACCCAGCUGAGUCACUGUCACUGCCUA CCAAUCUCGACCGGACCUCGACCGGCUCGUCUGU GUUGCCAAUCGACUCGGCUGGGCGUCGGUCUGG UAGAUAGGCGGUCAUGCAUACGAAUUUUCAGCUC UUGUUCUGGUGAC | SEQ ID NO: 29 |

TABLE 1-continued

| Human miRNA | Sequence | SEQ ID NO: |
|---|---|---|
| hsa-miR-17-5p | CAAAGUGCUUACAGUGCAGGUAG | SEQ ID NO: 30 |
| hsa-miR-1066-3p | CCGCACUGUGGGUACUUGCUGC | SEQ ID NO: 31 |
| hsa-miR-17 | GUCAGAAUAAUGUCAAAGUGCUUACAGUGCAGGU AGUGAUAUGUGCAUCUACUGCAGUGAAGGCACUU GUAGCAUUAUGGUGAC | SEQ ID NO: 32 |
| hsa-miR-142 | GACAGUGCAGUCACCCAUAAAGUAGAAAGCACUA CUAACAGCACUGGAGGGUGUAGUGUUUCCUACUU UAUGGAUGAGUGUACUGUG | SEQ ID NO: 33 |
| hsa-miR-106a | CCUUGGCCAUGUAAAAGUGCUUACAGUGCAGGUA GCUUUUUGAGAUCUACUGCAAUGUAAGCACUUCU UACAUUACCAUGG | SEQ ID NO: 34 |
| hsa-miR-106a-5p | AAAAGUGCUUACAGUGCAGGUAG | SEQ ID NO: 35 |
| hsa-miR-100 | CCUGUUGCCACAAACCCGUAGAUCCGAACUUGUG GUAUUAGUCCGCACAAGCUUGUAUCUAUAGGUAU GUGUCUGUUAGG | SEQ ID NO: 36 |
| hsa-miR-142-5p | CAUAAAGUAGAAAGCACUACU | SEQ ID NO: 37 |
| hsa-miR-100-5p | AACCCGUAGAUCCGAACUUGUG | SEQ ID NO: 38 |
| hsa-miR-144-5p | GGAUAUCAUCAUAUACUGUAAG | SEQ ID NO: 39 |
| hsa-miR-106b | CCUGCCGGGGCUAAAGUGCUGACAGUGCAGAUAG UGGUCCUCUCCGUGCUACCGCACUGUGGGUACUU GCUGCUCCAGCAGG | SEQ ID NO: 40 |
| hsa-miR-370 | AGACAGAGAAGCCAGGUCACGUCUCUGCAGUUAC ACAGCUCACGAGUGCCUGCUGGGGUGGAACCUGG UCUGUCU | SEQ ID NO: 41 |
| hsa-miR-370 | AGACAGAGAAGCCAGGUCACGUCUCUGCAGUUAC ACAGCUCACGAGUGCCUGCUGGGGUGGAACCUGG UCUGUCU | SEQ ID NO: 42 |
| hsa-miR-487b | UUGGUACUUGGAGAGUGGUUAUCCCUGUCCUGUU CGUUUUGCUCAUGUCGAAUCGUACAGGGUCAUCC ACUUUUUCAGUAUCAA | SEQ ID NO: 43 |
| hsa-miR-486-5p | UCCUGUACUGAGCUGCCCCGAG | SEQ ID NO: 44 |
| hsa-miR-126-3p | UCGUACCGUGAGUAAUAAUGCG | SEQ ID NO: 45 |
| hsa-miR-223 | CCUGGCCUCCUGCAGUGCCACGCUCCGUGUAUUU GACAAGCUGAGUUGGACACUCCAUGUGGUAGAGU GUCAGUUUGUCAAAUACCCCAAGUGCGGCACAUG CUUACCAG | SEQ ID NO: 46 |
| hsa-miR-223-3p | UGUCAGUUUGUCAAAUACCCCA | SEQ ID NO: 47 |
| hsa-miR-126 | CGCUGGCGACGGGACAUUAUUACUUUUGGUACGC GCUGUGACACUUCAAACUCGUACCGUGAGUAAUA AUGCGCCGUCCACGGCA | SEQ ID NO: 48 |
| hsa-miR-126-5p | CAUUAUUACUUUUGGUACGCG | SEQ ID NO: 49 |
| hsa-miR-1468 | GGUGGGUGGUUUCUCCGUUUGCCUGUUUCGCUGA UGUGCAUUCAACUCAUUCUCAGCAAAAUAAGCAA AUGGAAAAUUCGUCCAUC | SEQ ID NO: 50 |
| hsa-miR-1468 | GGUGGGUGGUUUCUCCGUUUGCCUGUUUCGCUGA UGUGCAUUCAACUCAUUCUCAGCAAAAUAAGCAA AUGGAAAAUUCGUCCAUC | SEQ ID NO: 51 |
| hsa-miR-411-5p | UAGUAGACCGUAUAGCGUACG | SEQ ID NO: 52 |
| hsa-miR-411 | UGGUACUUGGAGAGAUAGUAGACCGUAUAGCGUA CGCUUUAUCUGUGACGUAUGUAACACGGUCCACU AACCCUCAGUAUCAAAUCCAUCCCCGAG | SEQ ID NO: 53 |
| hsa-miR-1066-3p | CCGCACUGUGGGUACUUGCUGC | SEQ ID NO: 54 |

TABLE 1-continued

| Human miRNA | Sequence | SEQ ID NO: |
|---|---|---|
| hsa-miR-17 | GUCAGAAUAAUGUCAAAGUGCUUACAGUGCAGGU AGUGAUAUGUGCAUCUACUGCAGUGAAGGCACUU GUAGCAUUAUGGUGAC | SEQ ID NO: 55 |
| hsa-miR-142 | GACAGUGCAGUCACCCAUAAAGUAGAAAGCACUA CUAACAGCACUGGAGGGUGUAGUGUUUCCUACUU UAUGGAUGAGUGUACUGUG | SEQ ID NO: 56 |
| hsa-miR-100 | CCUGUUGCCACAAACCCGUAGAUCCGAACUUGUG GUAUUAGUCCGCACAAGCUUGUAUCUAUAGGUAU GUGUCUGUUAGG | SEQ ID NO: 57 |
| hsa-miR-142-5p | CAUAAAGUAGAAAGCACUACU | SEQ ID NO: 58 |
| hsa-miR-100-5p | AACCCGUAGAUCCGAACUUGUG | SEQ ID NO: 59 |
| hashsa-miR-486-5p | UCCUGUACUGAGCUGCCCCGAG | SEQ ID NO: 60 |
| hsa-miR-1066 | CCUGCCGGGGCUAAAGUGCUGACAGUGCAGAUAG UGGUCCUCUCCGUGCUACCGCACUGUGGGUACUU GCUGCUCCAGCAGG | SEQ ID NO: 61 |
| hsa-miR-17 | GUCAGAAUAAUGUCAAAGUGCUUACAGUGCAGGU AGUGAUAUGUGCAUCUACUGCAGUGAAGGCACUU GUAGCAUUAUGGUGAC | SEQ ID NO: 62 |
| hsa-miR-135a | AGGCCUCGCUGUUCUCUAUGGCUUUUUAUUCCUA UGUGAUUCUACUGCUCACUCAUAUAGGGAUUGGA GCCGUGGCGCACGGCGGGGACA | SEQ ID NO: 63 |
| hsa-miR-1356 | CACUCUGCUGUGGCCUAUGGCUUUUCAUUCCUAU GUGAUUGCUGUCCCAAACUCAUGUAGGGCUAAAA GCCAUGGGCUACAGUGAGGGGCGAGCUCC | SEQ ID NO: 64 |
| hsa-miR-26a-1 | GUGGCCUCGUUCAAGUAAUCCAGGAUAGGCUGUG CAGGUCCCAAUGGGCCUAUUCUUGGUUACUUGCA CGGGGACGC | SEQ ID NO: 65 |
| hsa-miR-30c-2 | AGAUACUGUAAACAUCCUACACUCUCAGCUGUGG AAAGUAAGAAAGCUGGGAGAAGGCUGUUUACUCU UUCU | SEQ ID NO: 66 |
| hsa-miR-92a-1 | CUUUCUACACAGGUUGGGAUCGGUUGCAAUGCUG UGUUUCUGUAUGGUAUUGCACUUGUCCCGGCCUG UUGAGUUUGG | SEQ ID NO: 67 |
| rno-miR-292 | CAACCUGUGAUACUCAAACUGGGGGCUCUUUUGG GUUUUCUUUGGAAGAAAAGUGCCGCCAGGUUUUG AGUGUUACCGAUUG | SEQ ID NO: 68 |
| hsa-miR-182 | GAGCUGCUUGCCUCCCCCCGUUUUUGGCAAUGGU AGAACUCACACUGGUGAGGUAACAGGAUCCGGUG GUUCUAGACUUGCCAACUAUGGGGCGAGGACUCA GCCGGCAC | SEQ ID NO: 69 |

In additional examples, a miRNA nucleic acid molecule includes a miRNA nucleic acid that is slightly longer or shorter than the nucleotide sequence of any one of the miRNAs listed in Table 1, as long as the miRNA nucleic acid retains a function of the particular miRNA, such as hybridization to a miRNA target sequence. For example, a miRNA nucleic acid can include a few nucleotide deletions or additions at the 5'- or 3'-end of the nucleotide sequence of a miRNA listed in Table 1, such as addition or deletion of 1, 2, 3, 4, or more nucleotides from the 5'- or 3'-end, or combinations thereof (such as a deletion from one end and an addition to the other end). In particular examples, a mature miRNA nucleic acid is about 17 to 25 nucleotides in length (for example, 17, 18, 19, 20, 21, 22, 23, 24, or 25 nucleotides in length).

miRNA mimics are also of use. The miRNAs or miRNA mimics (e.g. are small, double-stranded RNA molecules designed to mimic endogenous mature miRNA molecules) of use in the methods disclosed herein can be directly delivered to a subject.

A vector including a nucleic acid molecule encoding the miRNA can be utilized. In embodiments wherein more than one nucleic acid encoding a miRNA is utilized, the nucleic acids encoding the miRNAs all can be present in one vector. In other embodiments, more than one vector can be utilized, such as encoding 1, 2, 3, 4, or 5 miRNAs.

Generally a promoter is operably linked to a nucleic acid molecule encoding the one or more miRNA. The promoter can be an inducible or constitutive promoter. The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2kb, HSP70, proliferin, tumor necrosis factor, or a neuronal specific promoter. In some embodiments, the promoter is a constitutive promoter that results in high levels of transcription upon introduction into a host cell in the absence of additional factors. The cytomegalovirus (CMV) or neurofilament heavy chain gene promoters (Jacquier et al., Frontiers in Neurosci. 11: 521, 2017) can be used to provide expression of corresponding miRNAs in retinal ganglion cells. Optionally, the transcription control sequences include one or more enhancer elements, which are binding recognition sites for one or more transcription factors that increase transcription above that observed for the promoter alone.

Disclosed herein are methods and compositions that include utilize one or more vectors, such as a viral vector, such as a retroviral vector, for example an adenoviral vector, or an AAV that include a nucleic acid molecule encoding the miRNA operably linked to a promoter. Defective viruses, that entirely or almost entirely lack viral genes, can be used. Use of defective viral vectors allows for administration to specific cells without concern that the vector can infect other cells. The AAV vectors of use include replication competent, replication deficient, gutless forms thereof. Without being bound by theory, such vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone. In some non-limiting examples, a vector of use is an attenuated adenovirus vector, such as the vector described by Stratford-Perricaudet et al. (*J. Clin. Invest.*, 90:626-630 1992; La Salle et al., *Science* 259:988-990, 1993); or a defective AAV vector (Samulski et al., *J. Virol.*, 61:3096-3101, 1987; Samulski et al., *J. Virol.*, 63:3822-3828, 1989; Lebkowski et al., *Mol. Cell. Biol.*, 8:3988-3996, 1988).

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency. Further provided are recombinant vectors, such as recombinant adenovirus vectors and recombinant adeno-associated virus (rAAV) vectors comprising a nucleic acid molecule disclosed herein.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008). In some embodiments, these elements are included in the AAV vector.

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008). In some embodiments, these elements are included in the AAV vector.

In some embodiments, the AAV is rAAV2 and/or AAV8. However, the AAV serotype can be any other suitable AAV serotype, such as AAV1, AAV3, AAV4, AAV5, AAV6, AAV7, AAV8, AAV9, AAV10, AAV11 or AAV12, or a hybrid of two or more AAV serotypes (such as, but not limited to AAV2/1, AAV2/7, AAV2/8 or AAV2/9). Additional AAV of use are AAV5, AAV6 and AAV9. Adenovirus, AAV2 and AAV8 are capable of transducing cells. Thus, any of a rAAV2 or rAAV8 vector can be used in the methods disclosed herein. However, rAAV6 and rAAV9 vectors are also of use.

Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. AAV8 preferentially infects cells of the pancreas. Because of the advantageous features of AAV, the present disclosure contemplates the use of an rAAV for the methods disclosed herein.

AAV possesses several additional desirable features for a gene therapy vector, including the ability to bind and enter target cells, enter the nucleus, the ability to be expressed in the nucleus for a prolonged period of time, and low toxicity. AAV can be used to transfect cells, and suitable vector are known in the art, see for example, U.S. Published Patent Application No. 2014/0037585, incorporated herein by reference. Methods for producing rAAV suitable for gene therapy are well known in the art (see, for example, U.S. Published Patent Application Nos. 2012/0100606; 2012/0135515; 2011/0229971; and 2013/0072548; and Ghosh et al., *Gene Ther* 13(4):321-329, 2006), and can be utilized with the methods disclosed herein.

AAV8 vectors are disclosed, for example, in U.S. Pat. No. 8,692,332, which is incorporated by reference herein. An exemplary AAV8 nucleic acid sequence is shown in FIG. 1 and SEQ ID NO: 1 of U.S. Pat. No. 8,692,332, incorporated herein by reference. It is disclosed that AAV nucleic acid sequence can be greater than about 90%, 95%, 98% or 99% identical to this nucleic acid sequence. The location and sequence of the capsid, rep 68/78, rep 40/52, VP1, VP2 and VP3 are disclosed in this U.S. Pat. No. 8,692,332. The location and hypervariable regions of AAV8 are also provided.

The vectors of use in the methods disclosed herein can contain nucleic acid sequences encoding an intact AAV capsid which may be from a single AAV serotype (e.g., AAV2, AAV, 6, AAV8 or AAV9). As disclosed in U.S. Pat. No. 8,692,332, vectors of use can also can be recombinant, and thus can contain sequences encoding artificial capsids which contain one or more fragments of the AAV8 capsid fused to heterologous AAV or non-AAV capsid proteins (or fragments thereof). These artificial capsid proteins are selected from non-contiguous portions of the AAV2, AAV6, AAV8 or AAV9 capsid or from capsids of other AAV serotypes. For example, a rAAV vector may have a capsid protein comprising one or more of the AAV8 capsid regions selected from the VP2 and/or VP3, or from VP1, or fragments thereof selected from amino acids 1 to 184, amino acids 199 to 259; amino acids 274 to 446; amino acids 603 to 659; amino acids 670 to 706; amino acids 724 to 738 of the AAV8 capsid, see SEQ ID NO: 2 of U.S. Pat. No. 8,692,332. In another example, it may be desirable to alter the start codon of the VP3 protein to GTG. Alternatively, the rAAV may contain one or more of the AAV serotype 8 capsid protein hypervariable regions, for example aa 185-198; aa 260-273; aa447-477; aa495-602; aa660-669; and aa707-723 of the AAV8 capsid set forth in SEQ ID NO: 2 of U.S. Pat. No. 8,692,332, incorporated herein by reference.

In some embodiments, a recombinant adeno-associated virus (rAAV) is generated having an AAV serotype 8 capsid. To produce the vector, a host cell which can be cultured that contains a nucleic acid sequence encoding an AAV serotype 8 capsid protein, or fragment thereof, as defined herein; a functional rep gene; a minigene composed of, at a minimum, AAV inverted terminal repeats (ITRs) and a transgene, such as a transgene encoding a miRNA; and sufficient helper functions to permit packaging in the AAV8 capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. In some embodiments, a stable host cell will contain the required component(s) under the control of an inducible promoter. However, the required component(s) can be under the control of a constitutive promoter. Examples of suitable inducible and constitutive promoters are provided below. Similar methods can be used to generate a rAAV2, rAAV6 or rAAV9 vector and/or virion.

In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing a rAAV can be delivered to the packaging host cell in the form of any genetic element which transfer the sequences carried thereon. The selected genetic element may be delivered by any suitable method, including those described herein. The methods used to construct vectors are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745. In some embodiments, selected AAV components can be readily isolated using techniques available to those of skill in the art from an AAV serotype, including AAV8. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GENBANK®.

In the context of the present disclosure, a nucleic acid molecule encoding miRNA, or a biologically active portion thereof, can be administered to the subject either as naked RNA or DNA in combination with a delivery reagent, or can be encoded by a recombinant plasmid or viral vector, such as the AAV vectors disclosed above. AAV particles can also be used. AAV particles can be produced using methods know in the art. See, e.g., U.S. Pat. Nos. 6,566,118; 6,989, 264; and 6,995,006. In practicing the invention, host cells for producing AAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

Methods for producing AAV particles are known, and include (a) culturing a host cell under a condition that AAV particles are produced, wherein the host cell comprises (i) one or more AAV package genes, wherein each said AAV packaging gene encodes an AAV replication and/or encapsidation protein; (ii) a AAV pro-vector comprising a nucleic acid encoding a therapeutic polypeptide and/or nucleic acid as described herein flanked by at least one AAV ITR, and (iii) an AAV helper function; and (b) recovering the rAAV particles produced by the host cell. The AAV particles can be purified, so that they are devoid of at least some of the other components that may also be present where the AAV particles naturally occur or are initially prepared from. Thus, for example, isolated AAV particles can be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Thus, provided are pharmaceutical compositions comprising an AAV particle comprising a miRNA, as disclosed above, and a pharmaceutically acceptable carrier. The pharmaceutical compositions may be suitable for any mode of administration described herein; for example, by intravitreal administration. In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

In other embodiments, liposomes are used to deliver the miRNA, or nucleic acid encoding the miRNA, to the eye of a subject. Liposomes can also increase the blood half-life of nucleic acids. Suitable liposomes for use with the present disclosure can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a nucleic acid molecule to a subject. Cationic lipids and polymers that can be used to deliver therapeutic nucleic acid molecules have been described (see, for example, Zhang et al., *J Control Release*. 123(1):1-10, 2007; Vorhies et al., *Methods Mol Biol.* 480:11-29, 2009; and U.S. Patent Application Publication No. 2009/0306194). Polypeptide carriers can also be used to administer nucleic acid molecules, such as miRNAs, to a subject (see, for example, Rahbek et al., *J. Gene Med.* 10:81-93, 2008).

Nucleic acid molecules can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

A nucleic acid encoding a miRNA, for example, as present in one or more AAV vectors, can be delivered into cells, such as retinal ganglion cells, by methods known in the art. For example, the system can be delivered by intravitreal injection. For in vivo delivery, a vector, such as an adenovirus or an AAV vector can be formulated into a pharmaceutical composition and will generally be administered locally. Appropriate doses depend on the subject being treated (e.g., human or nonhuman primate or other mammal), age and general condition of the subject to be treated, the severity of the condition being treated, the mode of administration of the AAV vector/virion, among other factors. An appropriate effective amount can be readily determined by one of skill in the art. Thus, a "therapeutically effective amount" will fall in a relatively broad range that can be determined through clinical trials.

Methods for making a medicament or pharmaceutical composition containing the nucleic acids or vectors described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

As discussed above, a miRNA, or nucleic acid encoding a miRNA (including in vectors) can be provided as a single administration, a periodic bolus (for example, to the eye, such as intravitreally) or as continuous infusion from an internal reservoir (for example, from an implant disposed at an intraocular location (see, U.S. Pat. Nos. 5,443,505 and 5,766,242)) or from an external reservoir (for example, from an intravenous bag). Components can be administered by continuous release for a particular period from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS. SCI. 41:1186-1191). A variety of devices suitable for administering components locally to the inside of the eye are known in the art. See, for example, U.S. Pat. Nos. 6,251,090, 6,299,895, 6,416,777, 6,413,540, and PCT/US00/28187.

The miRNA, or nucleic acid molecule encoding an miRNA, such as in one or more AAV vectors, may be formulated to permit release over a specific period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for intraocular injection. Typically the microspheres are composed of a polymer of lactic acid and glycolic acid, which are structured to form hollow spheres. The spheres can be approximately 15-30 microns in diameter and can be loaded with components described herein.

In some embodiments, for in vivo injection, such as injection directly to the subject, a therapeutically effective dose will be on the order of from about $10^5$ to $10^{16}$ of the AAV virions, such as $10^8$ to $10^{14}$ AAV virions. The dose, of course, depends on the efficiency of transduction, promoter strength, the stability of the message and the protein encoded thereby, and clinical factors. Effective dosages can be readily established by one of ordinary skill in the art through routine trials establishing dose response curves.

In some embodiments, if the subject composition is an AAV, an effective amount to achieve a desired change will be about $1\times10^8$ vector genomes or more, in some cases about $1\times10^9$, about $1\times10^{10}$, about $1\times10^{11}$, about $1\times10^{12}$, or about $1\times10^{13}$ vector genomes or more, in certain instances, about $1\times10^{14}$ vector genomes or more, and usually no more than about $1\times10^{15}$ vector genomes. In some embodiments, the amount of vector that is delivered is about $1\times10^{14}$ vectors or less, for example about $1\times10^{13}$, about $1\times10^{12}$, about $1\times10^{11}$, about $1\times10^{10}$, or about $1\times10^9$ vectors or less, in certain instances about $1\times10^8$ vectors, and typically no less than $1\times10^8$ vectors. In some non-limiting examples, the amount of vector genomes that is delivered is about $1\times10^{10}$ to about $1\times10^{11}$ vectors. In additional non-limiting examples, the amount of vector that is delivered is about $1\times10^{10}$ to about $1\times10^{12}$ vector genomes.

In some embodiments, the amount of pharmaceutical composition to be administered may be measured using multiplicity of infection (MOI). In some embodiments, MOI refers to the ratio, or multiple of vector or viral genomes to the cells to which the nucleic may be delivered. In some embodiments, the MOI may be about $1\times10^6$. In some cases, the MOI can be about $1\times10^5$ to about $1\times10^7$. In some cases, the MOI may be about $1\times10^4$ to about $1\times10^8$. In some cases, recombinant viruses of the disclosure are at least about $1\times10^1$, about $1\times10^2$, about $1\times10^3$, about $1\times10^4$, about $1\times10^5$, about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, about $1\times10^{15}$, about $1\times10^{16}$, about $1\times10^{17}$, and about $1\times10^{18}$ MOI. In some cases, recombinant viruses of this disclosure are about $1\times10^8$ to $1\times10^{14}$ MOI.

In some the amount of pharmaceutical composition delivered comprises about $1\times10^8$ to about $1\times10^{15}$ particles of recombinant viruses, about $1\times10^9$ to about $1\times10^{14}$ particles of recombinant viruses, about $1\times10^{10}$ to about $1\times10^{13}$ particles of recombinant viruses, or about $1\times10^{11}$ to about $1\times10^{12}$ particles of recombinant viruses (see U.S. Published Patent Application No. 2015/0259395, incorporated herein by reference).

Dosage treatment may be a single dose schedule or a multiple dose schedule to ultimately deliver the amount specified above. Moreover, the subject may be administered as many doses as appropriate. Thus, the subject may be given, e.g., $10^5$ to $10^{16}$ AAV virions in a single dose, or two, four, five, six or more doses that collectively result in delivery of, e.g., $10^5$ to $10^{16}$ AAV virions. One of skill in the art can readily determine an appropriate number of doses to administer.

In some embodiments, the AAV is administered at a dose of about $1\times10^{11}$ to about $1\times10^{14}$ viral particles (vp)/kg. In some examples, the AAV is administered at a dose of about $1\times10^{12}$ to about $8\times10^{13}$ vp/kg. In other examples, the AAV is administered at a dose of about $1\times10^{13}$ to about $6\times10^{13}$ vp/kg. In specific non-limiting examples, the AAV is administered at a dose of at least about $1\times10^{11}$, at least about $5\times10^{11}$, at least about $1\times10^{12}$, at least about $5\times10^{12}$, at least about $1\times10^{13}$, at least about $5\times10^{13}$, or at least about $1\times10^{14}$ vp/kg. In other non-limiting examples, the rAAV is administered at a dose of no more than about $5\times10^{11}$, no more than about $1\times10^{12}$, no more than about $5\times10^{12}$, no more than about $1\times10^{13}$, no more than about $5\times10^{13}$, or no more than about $1\times10^{14}$ vp/kg. In one non-limiting example, the AAV is administered at a dose of about $1\times10^{12}$ vp/kg. The AAV can be administered in a single dose, or in multiple doses (such as 2, 3, 4, 5, 6, 7, 8, 9 or 10 doses) as needed for the desired therapeutic results.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for different applications. Effective amounts of dose and/or dose regimen can readily be determined empirically from preclinical assays, from safety and escalation and dose range trials, individual clinician-patient relationships, as well as in vitro and in vivo assays.

In some embodiments, the pharmaceutical compositions can contain the vector, such as the AAV vector, and/or virions, and a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

In some embodiments, the excipients confer a protective effect on the AAV virion such that loss of AAV virions, as well as transduceability resulting from formulation procedures, packaging, storage, transport, and the like, is minimized. These excipient compositions are therefore considered "virion-stabilizing" in the sense that they provide higher AAV virion titers and higher transduceability levels than their non-protected counterparts, as measured using standard assays, see, for example, Published U.S. Application No. 2012/0219528, incorporated herein by reference. These Compositions therefore demonstrate "enhanced transduceability levels" as compared to compositions lacking the particular excipients described herein, and are therefore more stable than their non-protected counterparts.

Exemplary excipients that can used to protect the AAV virion from activity degradative conditions include, but are not limited to, detergents, proteins, e.g., ovalbumin and bovine serum albumin, amino acids, e.g., glycine, polyhydric and dihydric alcohols, such as but not limited to polyethylene glycols (PEG) of varying molecular weights, such as PEG-200, PEG-400, PEG-600, PEG-1000, PEG-1450, PEG-3350, PEG-6000, PEG-8000 and any molecular weights in between these values, with molecular weights of 1500 to 6000 preferred, propylene glycols (PG), sugar alcohols, such as a carbohydrate, preferably, sorbitol. The detergent, when present, can be an anionic, a cationic, a zwitterionic or a nonionic detergent. An exemplary detergent is a nonionic detergent. One suitable type of nonionic detergent is a sorbitan ester, e.g., polyoxyethylenesorbitan monolaurate (TWEEN®-20) polyoxyethylenesorbitan monopalmitate (TWEEN®-40), polyoxyethylenesorbitan monostearate (TWEEN®-60), polyoxyethylenesorbitan tristearate (TWEEN®-65), polyoxyethylenesorbitan monooleate (TWEEN®-80), polyoxyethylenesorbitan trioleate (TWEEN®-85), such as TWEEN®-20 and/or TWEEN®-80. These excipients are commercially available from a number of vendors, such as Sigma, St. Louis, Mo.

The amount of the various excipients present in any of the disclosed compositions varies and is readily determined by one of skill in the art. For example, a protein excipient, such as BSA, if present, will can be present at a concentration of between 1.0 weight (wt.) % to about 20 wt. %, preferably 10 wt. %. If an amino acid such as glycine is used in the formulations, it can be present at a concentration of about 1 wt. % to about 5 wt. %. A carbohydrate, such as sorbitol, if present, can be present at a concentration of about 0.1 wt % to about 10 wt. %, such as between about 0.5 wt. % to about 15 wt. %, or about 1 wt. % to about 5 wt. %. If polyethylene glycol is present, it can generally be present on the order of about 2 wt. % to about 40 wt. %, such as about 10 wt. % top about 25 wt. %. If propylene glycol is used in the subject formulations, it will typically be present at a concentration of about 2 wt. % to about 60 wt. %, such as about 5 wt. % to about 30 wt. %. If a detergent such as a sorbitan ester (TWEEN®) is present, it can be present at a concentration of about 0.05 wt. % to about 5 wt. %, such as between about 0.1 wt. % and about 1 wt %, see U.S. Published Patent Application No. 2012/0219528, which is incorporated herein by reference. In one example, an aqueous virion-stabilizing formulation comprises a carbohydrate, such as sorbitol, at a concentration of between 0.1 wt. % to about 10 wt. %, such as between about 1 wt. % to about 5 wt. %, and a detergent, such as a sorbitan ester (TWEEN®) at a concentration of between about 0.05 wt. % and about 5 wt. %, such as between about 0.1 wt. % and about 1 wt. %. Virions are generally present in the composition in an amount sufficient to provide a therapeutic effect when given in one or more doses, as defined above.

In some embodiments, the subject method results in a therapeutic benefit, such increasing the number of retinal ganglia cells. The method can prevent the development of glaucoma, or halting the progression of glaucoma. In some embodiments, the method includes the step of detecting that a therapeutic benefit has been achieved, see above.

The disclosure is illustrated by the following non-limiting Examples.

EXAMPLES

Recent evidence has shown that mesenchymal stem cells (MSC) secrete exosomes, membrane enclosed vesicles (30-100 nm) containing proteins, mRNA and miRNA which can be delivered to nearby cells. Exosomes isolated from bone marrow-derived MSC (BMSC) were tested in a rat optic nerve crush (ONC) model. Treatment of primary retinal cultures with BMSC-exosomes demonstrated significant neuroprotective and neuritogenic effects. Twenty-one days after ONC and weekly intravitreal exosome injections, optical coherence tomography, electroretinography, and immunohistochemistry was performed. BMSC-derived exosomes promoted statistically significant survival of RGC and regeneration of their axons while partially preventing RGC axonal loss and RGC dysfunction. Exosomes successfully delivered their cargo into inner retinal layers and the effects were reliant on miRNA, demonstrated by the diminished therapeutic effects of exosomes derived from BMSC after knockdown of Argonaute-2, a key miRNA effector molecule. Thus, BMSC-derived exosomes as a cell-free therapy for traumatic and degenerative ocular disease.

The effect of BMSC exosomes were examined in a clinically relevant setting utilizing two rat models of glaucoma. The miRNA responsible for this effect were also identified. Results are presented below.

Example 1

Methods

Animals:
Adult female Sprague-Dawley rats weighing 150-200 g (Charles River, Wilmington, Mass.) were maintained in accordance with guidelines described in the ARVO Statement for the Use of Animals in Ophthalmic and Vision Research, using protocols approved by the National Eye Institute Committee on the Use and Care of Animals.

Animals were kept at 21° C. and 55% humidity under a 12 hours light and dark cycle, given food/water ad libitum and were under constant supervision from trained staff. Animals were euthanized by rising concentrations of $CO_2$ before extraction of retinae.

Materials:
All reagents were purchased from Sigma (Allentown, Pa.) unless otherwise specified.

BMSC Cultures:
Human $CD29^+/CD44^+/CD73^+/CD90^+/CD45^-$ BMSC (confirmed by supplier; Lonza, Walkersville, Md.) from 3 donors were pooled and cultured in DMEM containing 1% penicillin/streptomycin and 10% exosome-depleted foetal bovine serum (Thermo Fisher Scientific, Cincinnati, Ohio). Cell cultures were maintained at 37° C. in 5% $CO_2$ with medium changed every 3 days and cells passaged with 0.05% trypsin/EDTA when 80% confluent. Human dermal fibroblasts (Lonza) were grown in the above conditions and used as a control. For all experiments, BMSC and fibroblasts were used at passage 2-5.

Transfection and Confirmation of Knockdown:
For a subgroup of animals, BMSC were transfected using LIPOFECTAMINE™ 3000 (Thermo Fisher) per the manufacturer's protocol. Briefly, 70% confluent BMSC grown in Opti-MEM medium were incubated with LIPOFECTAMINE™ 3000 reagent and either siRNA against Ago2 (SiAgo2; Thermo Fisher Scientific, #4392420/assay id s25931) or a scrambled control siRNA (SiScr; #4390843) for 48 hours. Ago2 knockdown was confirmed by Western blotting like previously[21] (data not shown).

Exosome isolation and quantification. Exosomes were isolated from BMSC and fibroblasts using EXOQUICK™ TC (System Biosciences, Mountain View, Calif.) per the manufacturer's instructions. Briefly, conditioned medium was centrifuged at 3000×g for 15 minutes to remove cells and debris, incubated with EXOQUICK™ reagent overnight at 4° C. (1:10 ratio with medium), centrifuged at 1500×g for 15 minutes a final time before the exosome pellet is resuspended in sterile phosphate-buffered saline (PBS). The exosome preparation is passed through a 0.22 μm filter to remove any large extracellular vesicles (microvesicles and apoptotic bodies).

Exosome concentration and size distribution were characterized using a NANOSIGHT™ LM10 instrument (Malvern, Worcester, Mass.), equipped with a 405 nm LM12 module and EM-CCD camera (DL-658-OEM-630; Andor, Concord, Mass.)

Isolation, purification and culture of retinal ganglion cells: Eight well chamber slides (Thermo Fisher Scientific) were pre-coated with 100 µg/ml poly-D-lysine for 60 minutes and then with 20 µg/ml laminin for 30 minutes. After culling and ocular dissection, the retinae of female Sprague-Dawley were minced in 1.25 ml of papain (20 U/ml; Worthington Biochem, Lakewood, N.J.; as per manufacturer's instructions (#LK003150)) containing 50 µg/ml of DNase I (62.5 µl; Worthington Biochem) and incubated for 90 minutes at 37° C. The retinal cell suspension was centrifuged at 300×g for 5 minutes and the pellet resuspended in 1.575 ml of Earle's balanced salt solution (Worthington Biochem) containing 1.1 mg/ml of reconstituted albumin ovomucoid inhibitor (150 µl; Worthington Biochem) and 56 µg/ml of DNase I (75 µl). After adding to the top of 2.5 ml of albumin ovomucoid inhibitor (10 mg/ml) to form a discontinuous density gradient, the retinal cell suspension was centrifuged at 70×g for 6 minutes and the cell pellet resuspended in 1 ml of PBS.

Retinal ganglion cells (RGCs) were purified from the retinal suspension using CD90.1 magnetic beads according to the manufacturer's instructions (Miltenyi Biotec, Auburn, Calif.; #130-096-209). Briefly, retinal cells are incubated with CD90.1 enrichment and CD11b depletion antibodies conjugated to magnetic beads. Following depletion, the retinal suspension is passed through a magnetized column and the enriched RGC are collected and plated at a density 5000 RGC/well in supplemented Neurobasal-A (25 ml Neurobasal-A (Thermo Fisher Scientific), 1× concentration of B27 supplement (Life Technologies), 0.5 mM of L-glutamine (62.5 µl; Thermo Fisher Scientific) and 50 µg/ml of gentamycin (125 µl; Thermo Fisher Scientific)).

In Vivo Experimental Design:

The experimental design is shown schematically in FIG. 1A. Seventy rats were divided into 3 groups: Group 1 consisted of 5 uninjured/untreated animals; Group 2 consisted of 30 rats with ocular hypertension induced by intracameral (ic) injection of microbeads; Group 3 consisted of 35 rats with ocular hypertension induced by laser photocoagulation of the trabecular meshwork (TM) and limbal vessels. Induction of the model as well as treatment with intravitreal (ivit) exosomes (BMSC or fibroblasts) began on day 0 with some animals further receiving a weekly treatment. While it is not possible to treat Group 3 monthly, as the experimental length is 21 days, Group 2 which is a 56 day experiment also received monthly injections. Along with BMSC and fibroblast exosome treatments, Group 3 also received exosomes derived from MSC transfected with SiAgo2 or SiScr.

Induction of Ocular Hypertension with Intracameral (ic) Microbeads:

Ocular hypertension was induced in Group 2 by ic injection of microbeads as previously described[33]. Anesthesia was induced with 5% Isoflurane (Baxter Healthcare Corp, Deerfield, Ill.)/1.5 L per minute $O_2$ and maintained at 3.5% throughout the procedure. Using a 15° degree blade (Fine Science Tools, Reading, Pa.) a small 2 mm incision was made at the peripheral cornea and aqueous humour was allowed to exude. Using the same incision site, a 10 µl solution of microbeads was administered with a glass micropipette, produced in-house from a glass capillary rod (Harvard Apparatus, Kent, UK) using a Flaming-Brown micropipette puller (Sutter Instruments, Novato, Calif.). The microbead solution was loaded into the microneedle immediately before injection and consisted of 50 of 6 µm beads (polybead polystyrene, Polysciences, Inc Cat #07312) followed by 5 µl of 10 µm beads (polybead polystyrene, Polysciences, Inc Cat #17136), both at concentrations of $2\times10^8$/ml. Administration was made slowly and the needle was retracted with a 2 minutes delay to minimize leakage. Due to the variable translucency of the eye after microbead injection, reliable electroretinography (ERG) and optical coherence tomography (OCT) measurements were not possible.

Induction of Ocular Hypertension with Laser Photocoagulation:

Ocular hypertension was induced in Group 3 by laser photocoagulation of the TM and circumferential limbal vessels as previously described[34]. Anesthesia was induced with intraperitoneal injection of Ketamine (100 mg/kg; Putney Inc., Portland, Me.)/Xylazine (10 mg/kg; Lloyd Inc, Shenandoah, Iowa). Pupil constriction and subsequent opening of the iridocorneal angle was achieved with 4% pilocarpine hydrochloride ophthalmic solution (Sandoz, Princeton, N.J.). A OcuLight GLx 532 nm laser (Iridex, Mountain View, Calif.) was used to deliver laser burns at 0.3 W, at a spot size of 100 µm and duration of 0.5 s. Three locations were photocoagulated: approximately 270° of the circumferential limbal vessels, episcleral veins branching from these limbal vessels and finally, a trans-scleral/trans-corneal 360° burn of the TM/iridocorneal angle. Nasal vasculature was left uninjured to prevent ischemia.

Intraocular Pressure (IOP) Recording:

IOP were recorded for all rats using a TONOLAB™ rebound tonometer (Colonial Medical Supply, Franconia, N.H.). IOP was recorded under isoflurane-induced anesthesia during the same 3 hour window each day, sampled 18 times and averaged for each individual recording (Mead et al. Cytotherapy 18: 487-496, 2016).

Intravitreal Delivery of Exosomes:

Under isoflurane-induced anesthesia, exosomes were injected into the vitreous, just posterior to the limbus using glass micropipette. A 5 µl volume of sPBS loaded with $3\times10^9$ exosomes was injected slowly and the needle was retracted after a 2 minute delay to minimize backflow. The concentration was chosen based on our previous study[21] that demonstrated efficacy.

Electroretinography Measurements of the Positive Scotopic Threshold Response:

ERG was recorded using the ESPION™ Ganzfeld full field system (Diagnosys LLC, Lowell, Mass.) on day 0 before induction of ocular hypertension, and on day 56/21 (Group 2 and 3 respectively) before animals were sacrificed. Rats were dark adapted for 12 hours overnight and prepared for ERG recording under dim red light (>630 nm). Anesthesia was induced with intraperitoneal injection of Ketamine/Xylazine and eyes dilated with tropicamide. Scotopic flash ERG was recorded from −5.5 to +10 log units with respect to standard flash in half log-unit steps. ERG traces were analysed using in built Espion software and the amplitude (with respect to baseline) was used as a measure of rat visual function. Traces at a light intensity of $1\times10^{-5}$ mcd/s were chosen for analysis as they gave a clean, unambiguous pSTR 100 ms after stimulus.

Optical Coherence Tomography Measurements of the Retinal Nerve Fiber Layer:

OCT was performed on rats under anesthesia (intraperitoneal Ketamine/Xylazine) on day 0 before induction of ocular hypertension, and on day 56/21 (Group 2 and 3 respectively) before animals were sacrificed. A SPECTRALIS™ HRA3 confocal scanning laser ophthalmoscope (Heidelberg Engineering, Heidelberg, Germany) was used to take images of the retina around the optic nerve head and in-built software segmented the retinal nerve fiber layer (RNFL) and quantified the thickness. Segmentation was manually adjusted when necessary to prevent inclusion of blood vessels that populate the RNFL.

RGC Counts in Retinal Whole Mounts:

Rats were euthanized at 56/21 days (Group 2 and 3 respectively) by rising concentration of $CO_2$, and perfused intracardially with 4% paraformaldehyde (PFA) in PBS. Eyes were enucleated and retinae dissected and immersion post-fixed in 4% PFA for 1 h at 4° C. Wholemounted retinae were permeabilized in 0.5% TRITON X-100™ in PBS for 15 minutes at −70° C., washed in fresh TRITON X-100™ for a further 15 min before incubation with primary antibody diluted in wholemount antibody diluting buffer (wADB2% bovine serum albumin, 2% TRITON X-100™ in PBS) overnight at 4° C. and, the following day, were washed 3×10 minutes in PBS and incubated with secondary antibodies in wADB for 2 hours at room temperature. After 2 hours, retinae were washed for 3×10 minutes in PBS and mounted vitreous side up on SUPERFROST™ glass slides (Superfrost Plus, Fisher Scientific, Pittsburgh, Pa.), facilitated by 4 equidistant cuts into the peripheral retina. Slides were allowed to air dry before mounting in VECTORSHIELD MOUNTING MEDIUM™ (Vector Laboratories, Peterborough, UK) and applying cover slips. The antibodies used are detailed in Table 1.

TABLE 1

Antibodies used in immunohistochemistry (IHC), immunocytochemistry (ICC), and Western blot (WB)

| Antigen | Dilution | Supplier | Catalogue no. |
|---|---|---|---|
| RBPMS | 1:500 (IHC) | Thermo Fisher | #ABN-1376 |
| βIII-tubulin | 1:500 (ICC) | Sigma | #T-8660 |
| Ago2 | 1:1000 (WB) | Thermo Fisher | #MA5-14861 |
| HSC70 | 1:5000 (WB) | Santa Cruz | #sc-7298 |
| Mouse IgG HRP | 1:2000 (WB) | GE Healthcare | #NA-931 |
| Guinea Pig IgG 546 | 1:400 (IHC) | Thermo Fisher | #A-11074 |
| Mouse IgG 488 | 1:400 (ICC) | Thermo Fisher | #A-11001 |
| Mouse IgG HRP | 1:2000 (WB) | GE Healthcare | #NA-931 |
| Rabbit IgG HRP | 1:10,000 (WB) | Cell Signalling | #7074 |

Figure 3C:
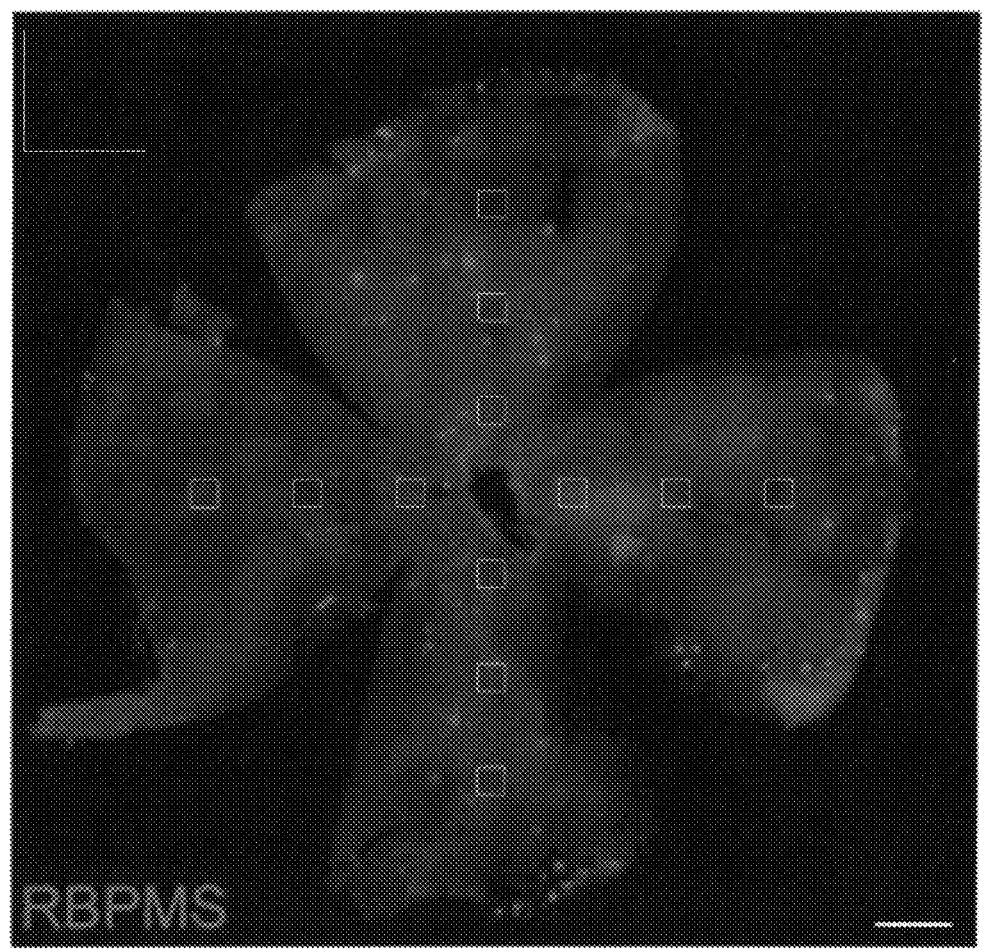
Figure 3D:
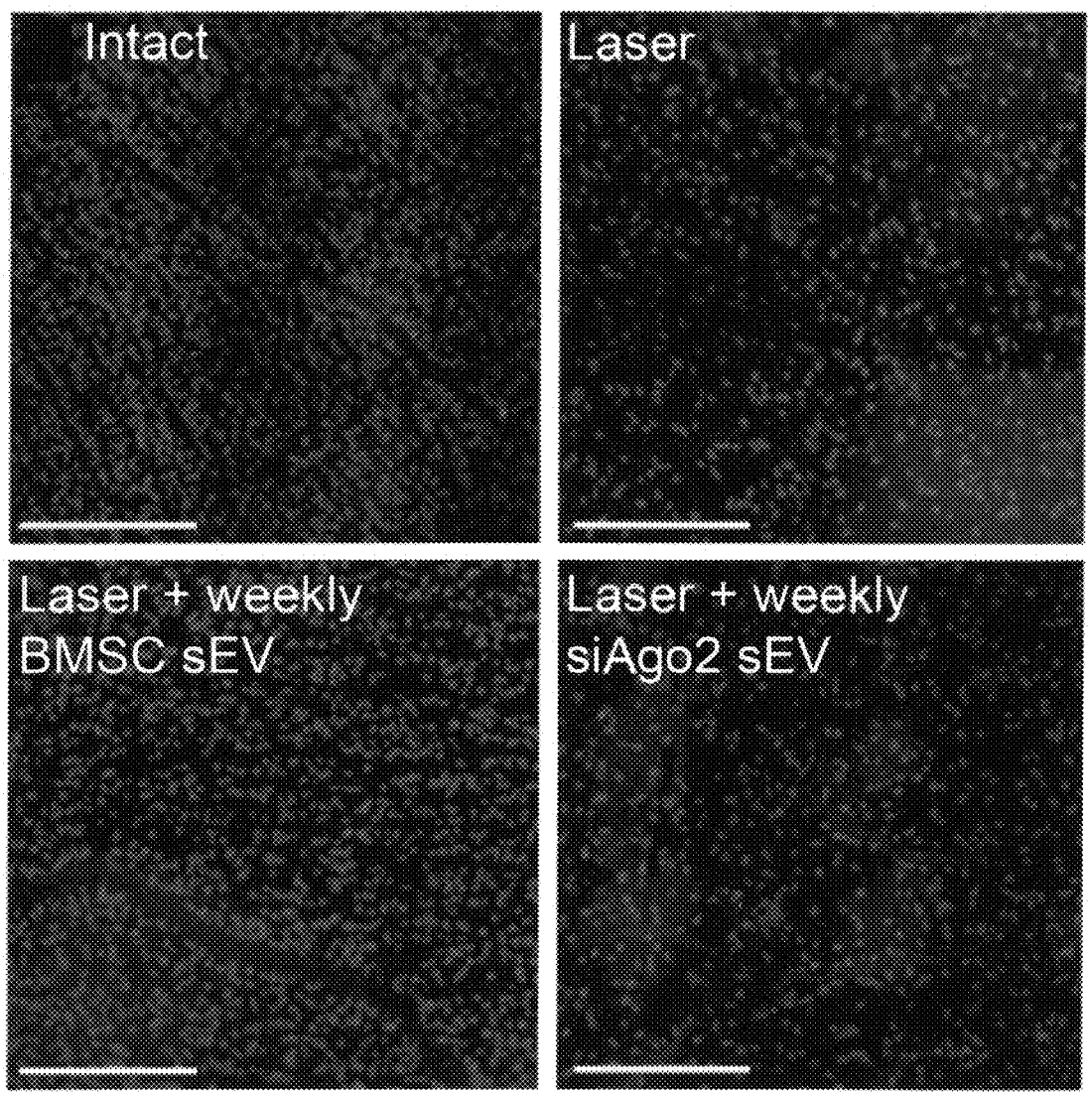
Figure 3E:
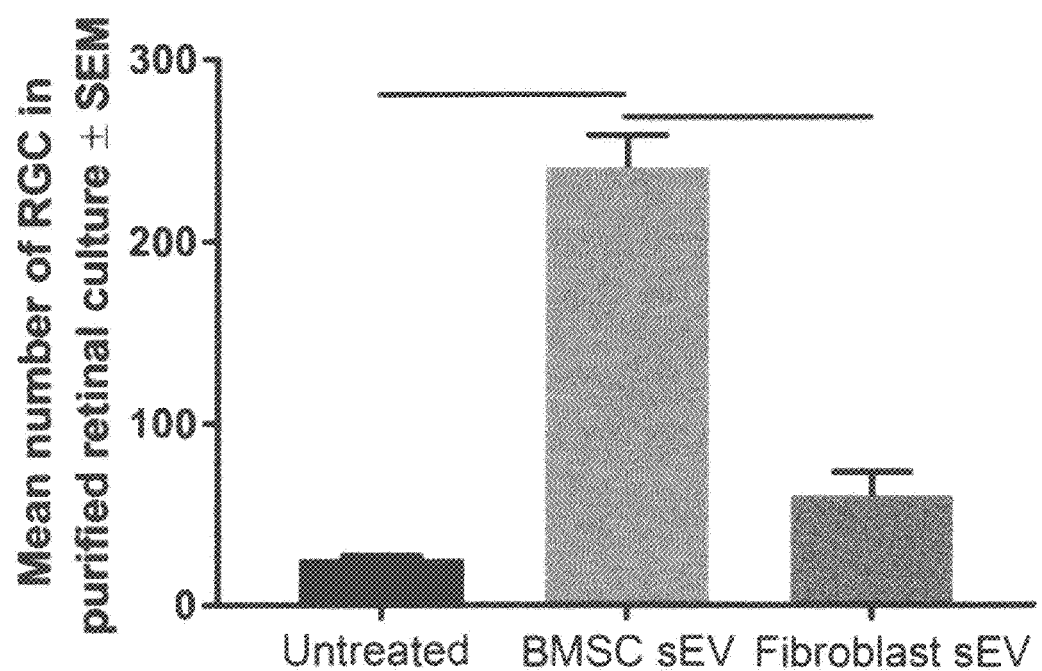

Retinal wholemounts were imaged using a Z1 Imager epifluorescent microscope and Axiocam HRc camera (Carl Zeiss Inc, Thornwood, N.Y.) and RNA binding protein with multiple splicing (RBPMS)+ cells were counted in three 0.33 mm² regions per retinal quadrant at 1, 2 and 3 mm from the optic nerve head (detailed in FIG. 3C). The mean number of RGC/image was derived from the 12 images and used to calculate RGC/mm² with each group consisting of an average of 10 retinae from 5 different animals.

RNA Sequencing:

RNAseq was performed by System Biosciences (#CSEQ400A-1) on exosomes isolated from BMSC and fibroblasts (as detailed above), 3 replicates per group. Exosomal RNA was quantified by bioanalyzer small RNA assay (Agilent, Santa Clara, Calif.) and libraries constructed and sequenced using ILLUMINA™ NextSeq instrument with 1×75 bp single-end reads at an approximate depth of 10-15 million reads per sample. A scaling factor for a given sample was computed as the median of the ratio of its read count for each gene over its geometric mean across all samples. Raw read counts were divided by the factor associated with their samples for normalization. Unlike protein-coding genes/mRNA-seq data analysis in which only uniquely mapped reads are considered, the miRNA pipeline needs to allow multiple mapping of the same read to account for the multiple copies. Thus, normalization was done on the number of read alignments mapped to annotated gene features across samples instead of the number of mapped reads.

The RNAseq data was displayed as a heat map of the $\log_2$ fold change between fibroblasts and BMSC. A miRNA was considered differentially abundant when the $\log_2$ fold change was >2 or <−2. Using INGENUITY PATHWAY ANALYSIS™ software, miRNA upregulated in BMSC as well as their predicted targets were mapped. Predicted targets were only considered if they were experimentally observed findings and the mRNA/miRNA sequences were present in both rat and human.

Statistics:

All statistical tests were performed using SPSS 17.0 (IBM SPSS, Inc., Chicago, Ill.) and data presented as mean±standard error of the mean with graphs constructed using GRAPHPAD PRISM™ 7.01 (Graphpad Prism, La Jolla, Calif.). The Shapiro-Wilkes test was used to ensure all data were normally distributed before parametric testing using a one-way analysis of variance (ANOVA) with a Tukey post-hoc test. Statistical differences were considered significant at p values <0.05.

Example 2

BMSC Secreted Exosomes

Exosomes isolated from human BMSC and fibroblasts were visualized clearly by NANOSIGHT™ and had a diameter of 100-120 nm, as expected for exosomes (FIG. 1B). Very few larger extracellular vesicles were detected and many of those that were detected were likely exosomal aggregates. No exosomes below 100 nm were detected due to limitations of the NANOSIGHT™ technology.

Example 3

Intracameral Microbeads and Laser Photocoagulation of the Trabecular Meshwork LED to Elevations in IOP Microbeads delivered ic (Group 2) led to a significant rise in IOP from 9.0±0.5 mmHg (Day 0) to 20.5±2.4 mmHg (Day 3), which remained high till the end of the experiment (14.2±2.0 mmHg; Day 56; FIG. 2A). In contrast, IOP in uninjected eyes (Group 1; 11.4±0.7 mmHg; Day 0) did not change significantly (10.3±0.6 mmHg; Day 56). The injection of exosomes into the vitreous did not significantly affect the IOP in ic microbead injected eyes.

Laser photocoagulation (Group 3) led to a significant rise in IOP from 9.0±0.4 mmHg (Day 0) to 25.0±5.8 mmHg (Day 7), which remained high till Day 17 (20.1±4.2 mmHg) but returned to baseline by the end of the experiment (11.1±1.4 mmHg; Day 21; FIG. 2B). In contrast, IOP in uninjected eyes (Group 1; 11.4±0.7 mmHg; Day 0) did not change significantly (11.7±1.8 mmHg; Day 21). The injection of exosomes into the vitreous did not significantly affect the IOP in laser photocoagulated eyes.

Example 4

Intravitreal BMSC Exosomes Promote Neuroprotection

The number of RBPMS+ RGC at day 56 in retinal wholemounts decreased significantly in the ic microbead glaucoma model (1468.7±186.3 RGC/mm$^2$) compared to intact eyes (2703.2±73.3 RGC/mm$^2$; FIG. 3A). Monthly and weekly ivit injection of BMSC exosomes provided significant neuroprotection of RGC (2113.8±99.0 RGC/mm$^2$, 2438.4±123.8 RGC/mm$^2$, respectively) but not single injection (1485.7±27.3 RGC/mm$^2$). Monthly and weekly ivit injection of fibroblast exosomes did not provide any neuroprotection to RGC (1485.0±216.7 RGC/mm$^2$, 1563.4±188.2 RGC/mm$^2$, respectively).

The number of RGC at day 21 in retinal wholemounts decreased significantly in the laser photocoagulation glaucoma model (1717.5±173.6 RGC/mm$^2$) compared to intact eyes (2703.2±73.3 RGC/mm$^2$; FIG. 3B). Single and weekly ivit injection of BMSC exosomes provided significant neuroprotection of RGC (2416.3±49.6 RGC/mm$^2$; 2609.3±66.3 RGC/mm$^2$, respectively). This protective effect was partially abolished after ivit injection of exosomes isolated from BMSC transfected with siAgo2 (2191.0±23.8 μm) but was still present if exosomes isolated from BMSC transfected with siScr were used (2550.2±109.7 μm). Successful knockdown of Ago2 with siAgo2 was confirmed using Western blot. Single and weekly ivit injection of fibroblast exosomes did not provide any neuroprotective effect to RGC (1975.6±6 RGC/mm$^2$; 1850.6±108.9 RGC/mm$^2$, respectively).

Example 5

BMSC Exosomes Promote Neuroprotection of RGC Partially Through Direct Mechanisms Untreated purified cultures of RGC showed significant death (25.7±1.7 RGC/well) relative to the 5000 RGC plated after 3 days in culture (FIG. 3C). While fibroblast exosomes provided little to no neuroprotective effect (60.7±13.0 RGC/well) BMSC exosomes elicited significant neuroprotection of (241±17.7 RGC/well).

Example 6

Intravitreal BMSC Exosomes Preserve RNFL Thickness/RGC Axonal Density

The thickness of the RNFL at day 21 decreased significantly in the laser photocoagulation glaucoma model (31.8±1.1 μm) compared to intact eyes (47.8±1.8 μm; FIG. 4). Single and weekly ivit injection of BMSC exosomes prevented degenerative thinning of the RNFL (46.0±1.3 μm; 45.0±1.8 μm, respectively). This protective effect was not present after ivit injection of exosomes isolated from BMSC transfected with siAgo2 (32.4±3.2 μm) but was still present if exosomes isolated from BMSC transfected with siScr were used (46.8±1.7 μm). Single and weekly ivit injection of fibroblast exosomes did not prevent degenerative thinning of the RNFL (33.8±1.5 μm; 34.0±1.5 μm, respectively). There was no significant difference between baseline recordings of all groups as well as compared to intact at day 21 (data not shown).

Example 7

Intravitreal BMSC Exosomes Preserve pSTR Amplitude/RGC Function

Figure 5A:
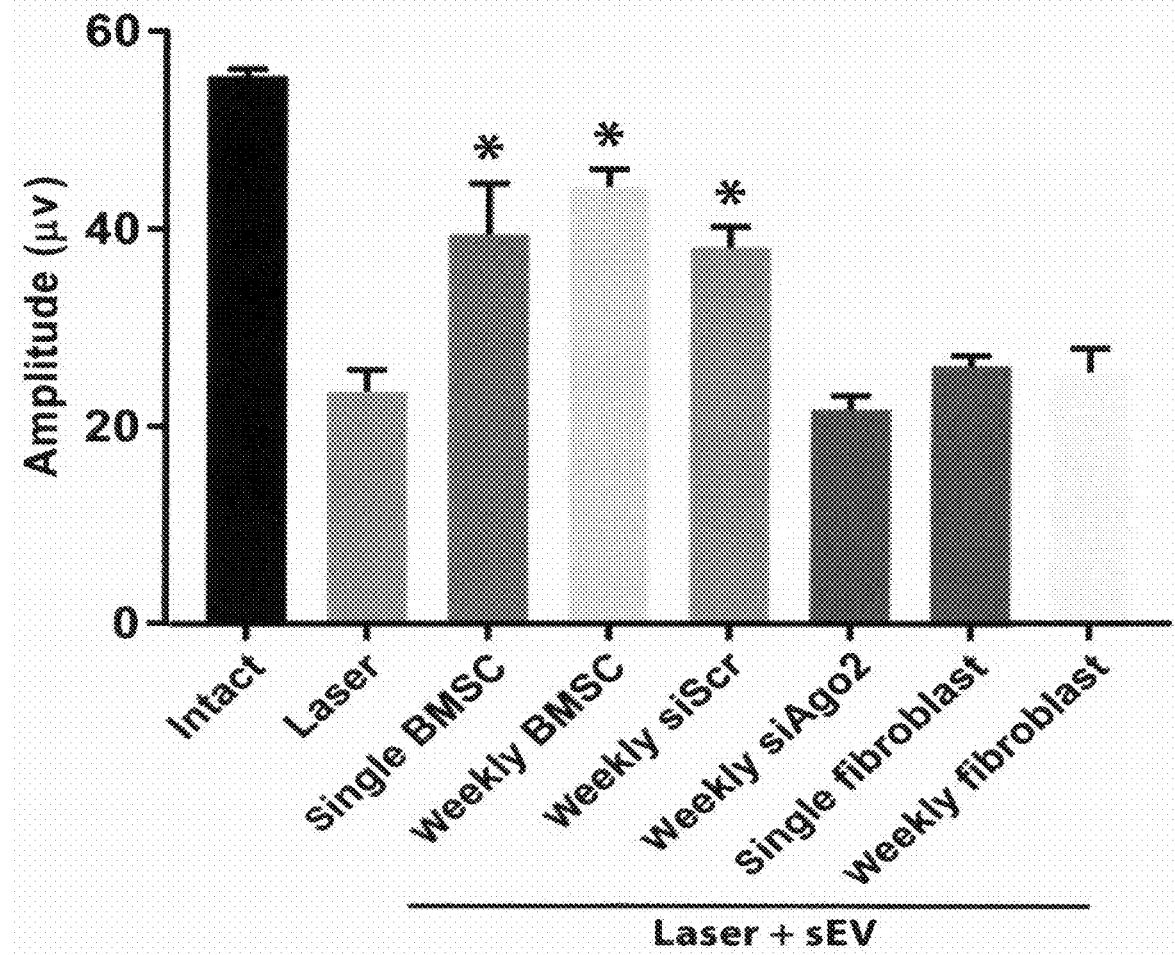
FIGS. 5A-5B. ERG measurements of pSTR. (A) Mean amplitude (µv) of pSTR measured by ERG in animals 21 days after laser photocoagulation. Asterisks indicate significant difference from injured/untreated at p<0.05. (B) Representative traces of pSTR.
Figure 5B:
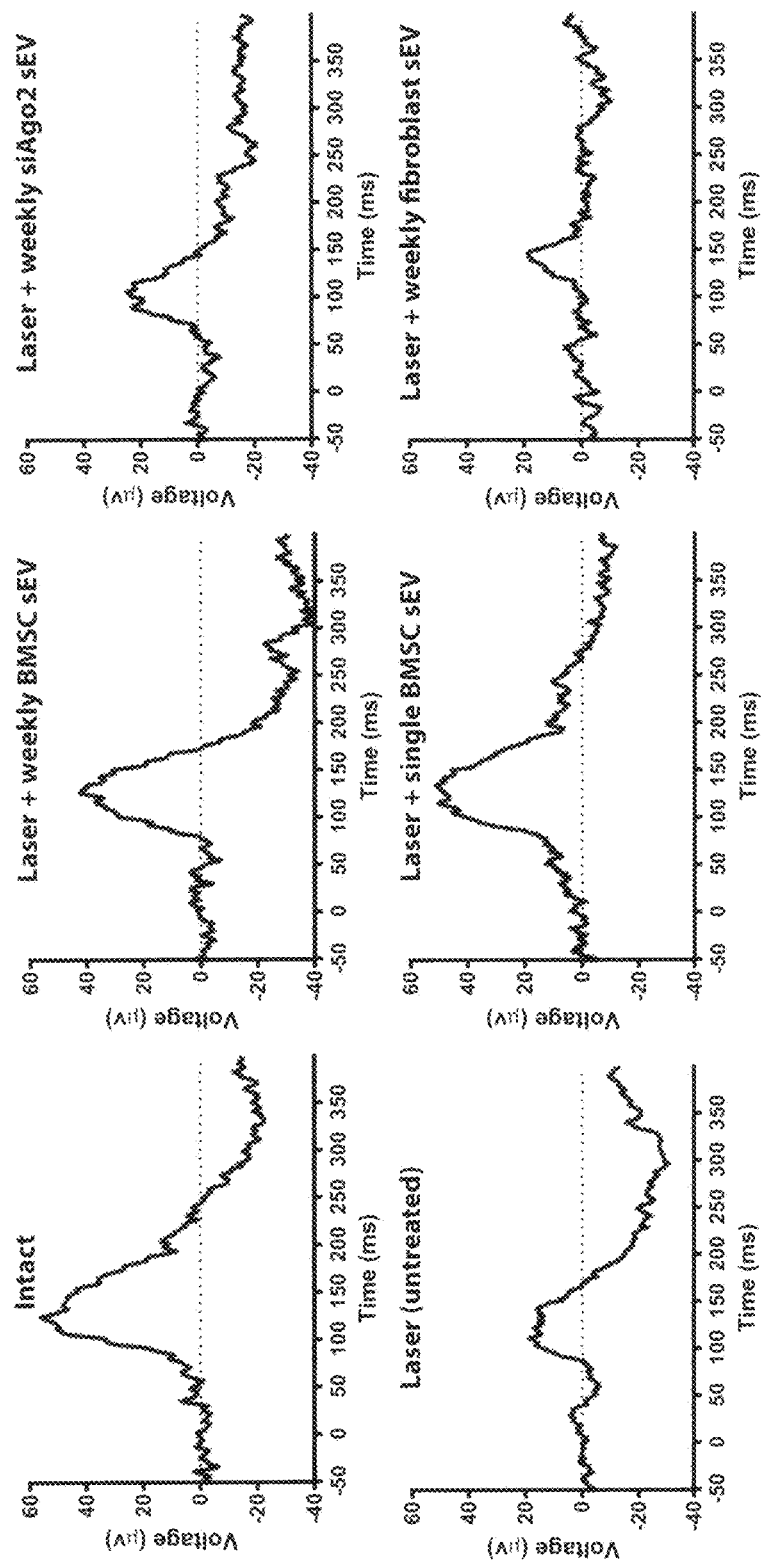

The amplitude of the pSTR at day 21 decreased significantly in the laser photocoagulation glaucoma model (23.6±2.2 μv) compared to intact eyes (55.5±0.7 μv; FIG. 5). Single and weekly ivit injection of BMSC exosomes prevented degenerative loss of the pSTR (39.5±5.1 μv; 44.3±1.7 μv, respectively). This protective effect was not present after ivit injection of exosomes isolated from BMSC transfected with siAgo2 (21.8±1.4 μv) but was still present if exosomes isolated from BMSC transfected with siScr were used (38.2±2.1 μv). Single and weekly ivit injection of fibroblast exosomes did not prevent degenerative loss of the pSTR (26.2±1.1 μm; 25.5±2.5 μm, respectively). There was no significant difference between baseline recordings of all groups as well as compared to intact at day 21 (data not shown).

Example 8

RNAseq Data

Figure 6:
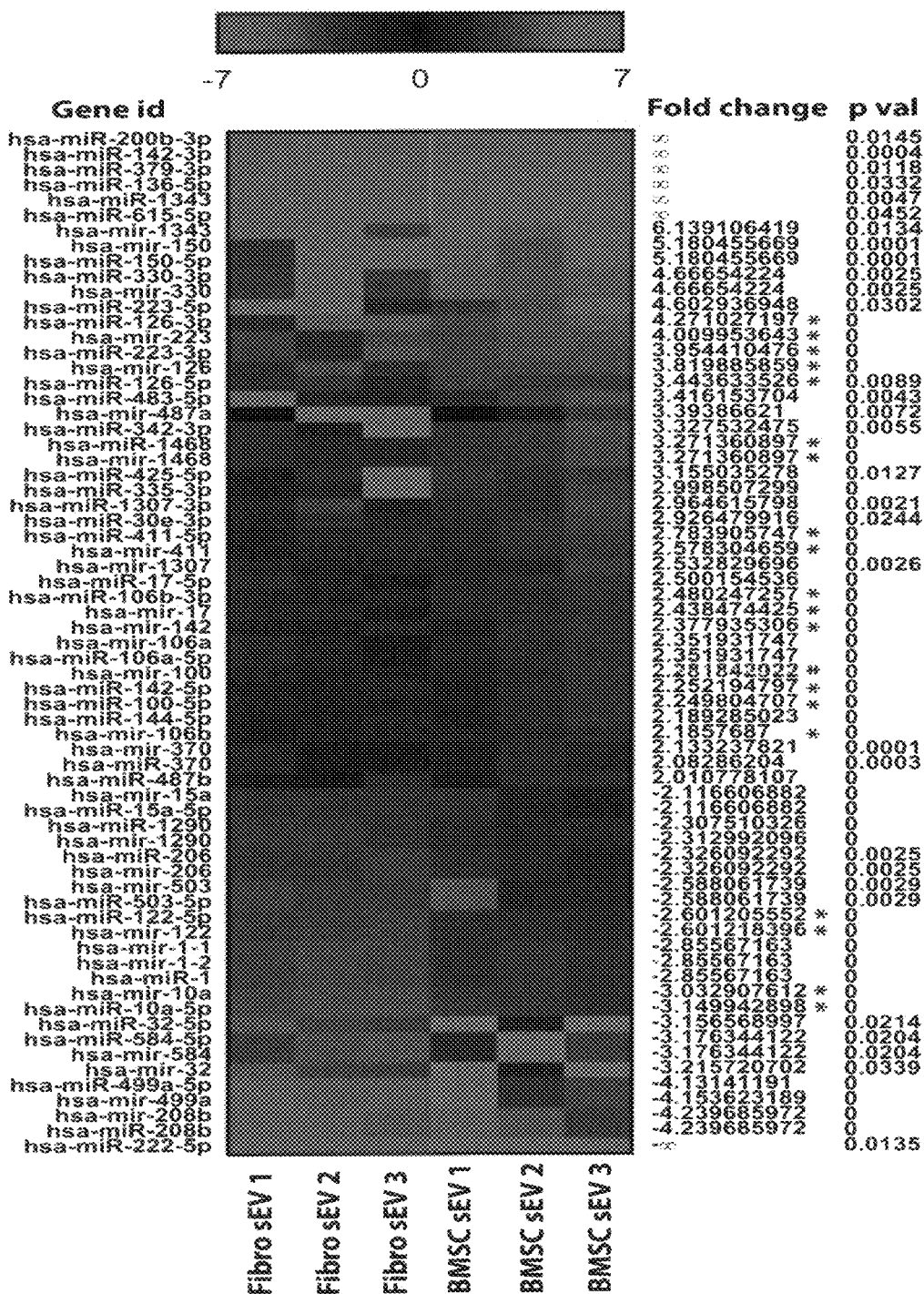
FIG. 6. miRNA abundance heat map profile. A comparison of the miRNA abundance profile in BMSC exosomes and fibroblast exosomes, displayed as a heat map of the log$_2$ fold change. Red indicates high comparative abundance whereas green denotes low comparative abundance. Average log$_2$ fold change, an abundance value >200 reads per million (Asterisk) as well as p value are given. miRNA with >2 or <−2 fold change only are shown FIG. 7. miRNA targeting network. Schematic diagram displaying miRNA (red) upregulated in BMSC exosomes and their experimentally observed mRNA targets (yellow). Targeted genes were identified with Ingenuity Pathway Analysis software and filtered for experimentally observed interactions and, miRNA/mRNA sequences identified in both human and rat.
Figure 7:
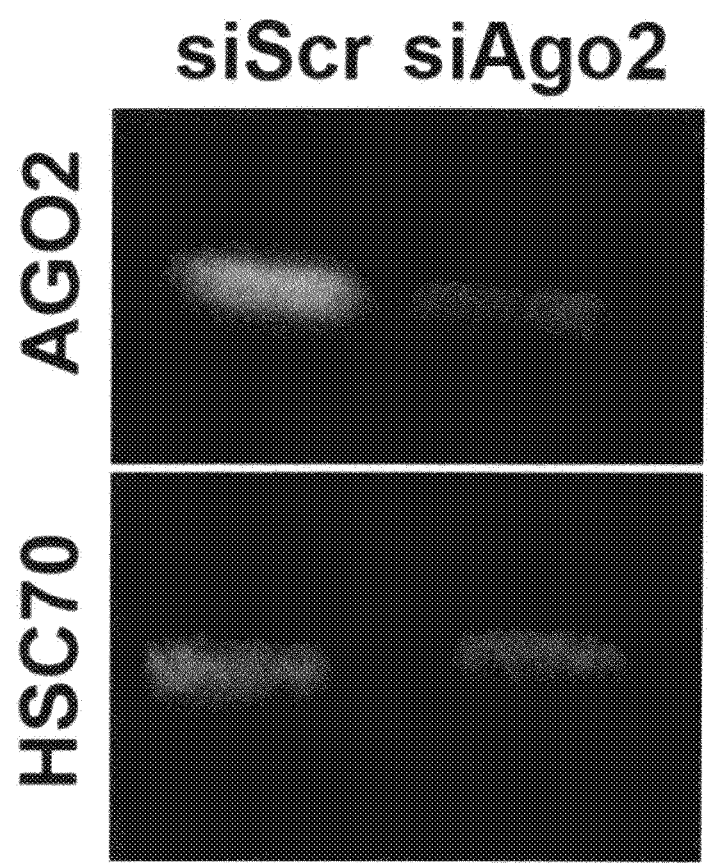

RNAseq detected 43 miRNA that were overabundant in BMSC by >2 (log$_2$ fold change) compared to fibroblasts and 24 miRNA that were overabundant in fibroblasts by >2 compared to BMSC (FIG. 6). Using INGENUITY PATHWAY ANALYSIS™, targets of the abundant miRNA were predicted (FIG. 7) and the most enriched/targeted signaling pathway identified (Table. 2).

TABLE 2

Enriched signaling pathways regulated by miRNA abundant in exosomes. Experimentally observed (A) and predicted (B) mRNA targets of miRNA overabundant in BMSC exosomes compared to fibroblast exosomes, displayed as the most enriched signaling pathways.

| Term | No. of genes A/B | P value |
|---|---|---|
| IL-15 signaling | 11/76 | <0.001 |
| JAK/STAT pathway | 10/83 | <0.001 |
| HGF signaling | 11/115 | <0.001 |
| PTEN signaling | 11/119 | <0.001 |
| IL-8 signaling | 13/197 | <0.001 |
| FGF signaling | 10/90 | <0.001 |
| PDGF signaling | 10/90 | <0.001 |
| EGF signaling | 9/68 | <0.001 |

The results demonstrate that exosomes derived from BMSC promote significant neuroprotection of RGC in two separate and distinct models of glaucoma whilst protecting against RNFL degeneration and pSTR loss. Without being bound by theory, the protective effect can be attributed to the miRNA found within exosomes, a finding corroborated by our previous study in an ONC rat model (Mead et al., *Stem Cells Transl Med* 2017; 6:1273-1285). Two models of glaucoma were utilized to minimize any limitations that are present in the glaucoma model. For examples, the laser model provides a short, recoverable rise in IOP whereas the is microbead model, while being characterized by a persistent rise in IOP, has opacities due to the beads in the anterior chamber, rendering ERG and OCT unreliable. Two models were used to ensure that the results were applicable to the clinical setting.

While MSC are currently undergoing clinical trials to test their efficacy in various ocular diseases (Mead et al., *Stem Cell Res* 2015; 14:243-257), their exosomes have been demonstrated safe in a recent clinical trial (Nassar et al., *Biomat Res* 2016; 20:21). Systemic delivery of UCB-MSC-derived exosomes into patients with chronic kidney disease proved not only safe, but also significantly improved kidney function while reducing inflammation.

Exosomes integrate into cells within the ganglion cell layer, suggesting that the effect was direct, independent of non-RGC retinal cell mediators. The findings demonstrate that in a purified culture, RGC undergo the stereotypical 95% death after 4 days (Xu et al., *J Neurochem* 2015; 133:233-241; Welsbie et al., *Proc Natl Acad Sci USA* 2013; 110:4045-4050) while treatment with exosomes from BMSC, but not fibroblasts, promoted significant RGC neuroprotection. This further confirms that at least some of the neuroprotective effect is mediated through direct exosome-RGC interactions.

The present study corroborates findings that showed BMSC exosome-mediated protection of RGC after ONC in the rat. Few studies exist testing exosomes as a treatment in the eye.

Therapeutic efficacy was demonstrated from weekly ivit injections (Mead et al., *Stem Cells Transl Med* 2017; 6:1273-1285 whereas a separate study used a single intravenous administration[26] at a much higher dose ($15 \times 10^9$ exosomes), demonstrating a therapeutic effect 21 days later in an experimentally autoimmune uveitis model.

Ideally, ocular treatment should be long lasting to minimize repeat injections and while there is a precedent for cell therapy to have long lasting effects, no studies have assessed the longevity of transplanted exosomes. Several different treatment schedules were used to address this question, injecting once, weekly, and monthly. Weekly ivit injections proved effective in all measured endpoints in this model system. Injections separated by 1 month also proved equally effective although a non-significant trend towards a reduced neuroprotective effect compared to weekly injections was observed in the microbead model. Since the microbead model takes place over 56 days, a single injection was also tested. The neuroprotective effects of BMSC exosomes was absent without a second injection after 1 month, suggesting that BMSC exosome activity drops dramatically after approximately 1 month in the vitreous. This timeframe likely represents both the duration exosomes reside in the vitreous and the length of time the miRNA-mediated gene regulation lasts. One of skill in the art can readily determine the dosing schedule appropriate for human subjects.

Ago2 knockdown-mediated depletion of miRNA partially inhibited the positive effects elicited by exosomes evident by the reduced RGC numbers, RNFL thickness and pSTR amplitude. miRNAseq was performed on BMSC to aid in the potential identification of candidates. Candidate miRNA were identified that were more abundant in BMSC exosomes in comparison to fibroblast exosomes.

The miRNA content of MSC exosomes has been identified. 11 miRNA present in UCB-MSC-derived exosomes were identified via microarray (Sun et al., *Sci Rep* 2017; 7:2552) while the top 100 most abundant miRNA were detailed using RNAseq (Qian et al., *Stem Cells Transl Med* 2016), demonstrating much overlap. These miRNA were also detected by the present RNAseq. However only miR-100-5p and miR-106a-5p were significantly more abundant in BMSC exosomes in comparison to fibroblast exosomes. Another study performed RNAseq on human ADSC-derived exosomes to identify the miRNA potentially responsible for the observed anti-cancer properties (Reza et al., *Sci Rep* 2016; 6:38498). Several of the miRNA that were detected were also identified in the present study including miR-1246 and miR-269-5p. However, these miRNA were also found in equal or greater abundance within fibroblast exosomes. miR-486-5p was more abundant (1.8 $\log_2$ fold change higher) in BMSC exosomes compared to fibroblast exosomes, as well as being one of the most abundant miRNA. This result was further confirmed by a separate RNAseq analysis performed on both human BMSC and ADSC (Baglio et al., *Stem cell Res Ther* 2015; 6:12) as well as demonstrating that abundant miRNA differed between each MSC source. MiR-135a and miR-135b also are abundant in MSC-derived exosomes can be used. These two miRNA are regulators of CNS axon growth and regeneration by targeting Kruppel-like factor 4 (van Battum et al. *J. Neurosci.* 38, 2018; 38:613-630).

Exosome mediated delivery of miRNA to the retina can only be effective if the packaged miRNA are not already abundantly present in the injured retina (Wang et al., *Acta Ophthalmol* 2017; 95:e10-e21; Karali et al., *Nucleic Acids Res* 2016; 44:1525-1540). MiR-144-5p, miR-126-5p and miR-100-5p were found to also be overabundant in BMSC exosomes. Since these miRNA are already present in the retina, their contribution following exosome-mediated delivery is likely minimal. In contrast, in the glaucomatous rat retina, several miRNA are downregulated including miR-106b (Jayaram et al., *Invest Ophthalmol Vis Sci* 2015; 56:7971-7982), which was found to be abundant in BMSC exosomes. It is feasible that downregulation of miRNA has some role in the pathology of glaucoma and delivery of these miRNA via BMSC exosomes prevents RGC degeneration.

While miRNA play an integral role in the exosome-mediated neuroprotection of RGC, siAgo2 exosomes trended towards neuroprotection, suggesting either the presence of residual miRNA or non-miRNA components of the exosome cargo contributing additional beneficial effects. As well as mRNA, BMSC exosomes are shown to contain approximately 5000 proteins (Erin et al., *Sci Rep* 2016; 6:36120). Recently, BMSC-derived exosomes were shown to express an isoform of PDGF, referred to as PDGF-D (Huang et al., *Int J Clin Exp Patho* 2017; 10:224-232). Since PDGF was been shown to be secreted from BMSC and promote significant RGC neuroprotection (Johnson et al., *Brain* 2014; 137:503-519), PDGF loaded in exosomes could also have an effect.

Thus, BMSC exosome promote neuroprotection and functional preservation of RGC in two rat glaucomatous models. While ivit injection of exosomes did not directly affect IOP, their neuroprotective efficacy provides an adjunctive therapy to IOP lowering medications and thus, a treatment for glaucoma.

Example 9

Material and Methods for Examples 10-16

All reagents were purchased from Sigma (Allentown, Pa.) unless otherwise specified.

BMSC Cultures:

Human BMSC were purchased from Lonza (Walkersville, Md.) and represented pooled samples from 3 donors. The $CD29^+/CD44^+/CD73^+/CD90^+/CD45^-$ (confirmed by supplier) BMSC were seeded into T25/T75 flasks (Corning, Acton, Mass.) in a total volume of 5 ml/15 ml DMEM containing 1% penicillin/streptomycin and 10% exosome-depleted fetal bovine serum (FBS; Thermo Fisher Scientific, Cincinnati, Ohio) and at a density of $1 \times 10^6$ cells/$2 \times 10^6$ cells, respectively. Cultures were maintained at 37° C. in 5% $CO_2$, the supplemented medium was changed every 3 days and the cells were passaged when 80% confluent using 0.05% trypsin/EDTA to lift them from their surface attachment. For control cells, human fibroblasts were purchased from Lonza and cultured in the exact same conditions. For all experiments, BMSC and fibroblasts were used at passage 2-5.

Transfection of BMSC with siRNA:

BMSC were transfected using LIPOFECTAMINE® 3000 (Thermo Fisher) according to the manufacturer's protocol. Briefly, 70% confluent BMSC grown in Opti-MEM medium were incubated with Lipofectamine 3000 reagent and either siRNA against Argonaute 2 (SiAgo2) or a scrambled control siRNA (SiScr) for 48 hours.

Western Blot:

Successful Ago2 knockdown was confirmed by Western blotting. Briefly, BMSC were washed in phosphate buffered saline (PBS), lysed in lysis buffer (20 mM Tris-HCl, 1 mM EDTA, 0.5 mM EGTA, 150 mM NaCl, 1% NP-40 and protease inhibitor) and sonicated before protein concentration was determined by BCA protein assay (Thermo Fisher). 20 µg total protein samples were separated on 4-12% Bis-Tris protein gels at 150 V for 40 minutes. Proteins were transferred to polyvinylidene fluoride membranes, blocked for 30 minutes in 10% Western blocking buffer in Tris buffered saline (TBS), stained for 1 hour with primary antibody diluted in TBS, washed with TBST for 3×5 mins, stained for 1 hour with secondary antibody before a final 3×5 minutes wash and detection with Femto ECL. Densitometry of Western blot bands was analyzed using ImageJ software (National Institutes of Health, Bethesda, Md.).

Exosome Isolation:

Exosomes were isolated from BMSC and fibroblasts using ultracentrifugation as previously described (Thery et al., Curr Protoc Cell Biol, 2006. Chapter 3: p. Unit 3 22). Briefly, BMSC/fibroblasts were cultured for 48 hours in exosome free serum and conditioned medium was collected and centrifuged at 300×g for 10 minutes, 2000×g for 10 minutes and 10,000×g for 30 minutes, discarding the pellet and collecting the supernatant each time. The supernatant was spun down at 100,000×g twice, each for 70 minutes, the pellet collected and resuspended in 1 ml sterile PBS (sPBS). To remove microvesicles, EV were filtered through a 0.22 µm filter to obtain exosomes. The supernatant was used as a negative control in the following step to confirm absence of exosomes. Exosomes were isolated from BMSC/fibroblasts at passage 2, up to passage 5.

Electron Microscopy:

Exosomes were doubly-fixed in a PBS-buffered glutaraldehyde (2.5% at pH 7.4) and osmium tetroxide (0.5%), and embedded in epoxy resin. Thin sections (90 nm) were collected on 200-mesh copper grids, air-dried, and doubly-stained with uranyl acetate and lead citrate. Sections were viewed with a JEOL JEM-1010 electron microscope, and photographed.

Exosome Quantification:

Exosomes were quantified using EXOELISA™ against CD63 (System Biosciences, Mountain View, Calif.) according to the manufacturer's instructions. Briefly a standard curve was constructed using exosome standards and test samples of purified exosomes from BMSC and fibroblasts, run in duplicate with exosome quantity extrapolated from the standard curve.

Exosome Surface Marker Expression:

The expression of surface epitopes was determined by flow cytometry using the MACSPlex Exosome Kit (human) (Cat No. 130108813 Miltenyi Biotec, Bergish Gladbach, Germany. Briefly, $2 \times 10^{10}$ exosomes were washed and suspended in sterile PBS and assayed using a MACSQUANT Analyzer 10 (Miltenyi Biotec) with MACSQUANTIFY™ Software Version 2.8. Assay was run in triplicate on three independent samples.

Exosome Tracking:

To track exosomes in vivo, EXO-GLOW™ (System Biosciences) was used to label purified exosomes prior to intravitreal injection, according to the manufacturer's instructions. Briefly, $3 \times 10^8$ exosomes were suspended in 500 µl of sPBS and incubated with Exo-Green labelling solution for 10 minutes at 37° C. followed by 30 minutes on ice. Labelled exosomes were isolated by treatment with EXO-QUICK-TC™ (System Biosciences), centrifugation for 30 minutes at 14,000×g, washed 3 times with sPBS before being resuspended in 500 µl of sPBS and kept on ice until intravitreal injection on the same day.

Animals:

Adult female Sprague-Dawley rats weighing 170-200 g (Charles River, Wilmington, Mass.) were maintained in accordance with art accepted guidelines.

Animals were kept at 21° C. and 55% humidity under a 12 hours light and dark cycle, given food/water ad libitum and were under constant supervision from trained staff. Animals were euthanized by rising concentrations of $CO_2$ before extraction of retinae.

Retinal Cell Culture:

Eight well chamber slides (Thermo Fisher Scientific) were pre-coated with 100 µg/ml poly-D-lysine for 60 minutes and then with 20 µg/ml laminin for 30 minutes. After culling and ocular dissection, the retinae of female Sprague-Dawley were minced in 1.25 ml of papain (20 U/ml; Worthington Biochem, Lakewood, N.J.; as per manufacturer's instructions) containing 50 µg/ml of DNase I (62.5 µl; Worthington Biochem) and incubated for 90 minutes at 37° C. The retinal cell suspension was centrifuged at 300×g for 5 minutes and the pellet resuspended in 1.575 ml of Earle's balanced salt solution (Worthington Biochem) containing 1.1 mg/ml of reconstituted albumin ovomucoid inhibitor (150 µl; Worthington Biochem) and 56 µg/ml of DNase I (75 µl). After adding to the top of 2.5 ml of albumin ovomucoid inhibitor (10 mg/ml) to form a discontinuous density gradient, the retinal cell suspension was centrifuged at 70×g for 6 minutes and the cell pellet resuspended in 1 ml of supplemented NEUROBASAL®-A (25 ml NEUROBASAL®-A (Thermo Fisher Scientific), 1× concentration of B27 supplement (Life Technologies), 0.5 mM of L-glutamine (62.5 µl; Thermo Fisher Scientific) and 50 µg/ml of gentamycin (125 µl; Thermo Fisher Scientific)) and seeded at a density of 125,000 cells/300 µl/well in a 8 well chamber slide. Selected cultures were treated with BMSC/fibroblast exosomes (before and after passing through a 0.22 µm filter) or human recombinant ciliary neurotrophic factor (50 ng/ml)/BMSC (50,000 cells) as a positive control. Cultures were incubated for 3 days at 37° C. before immunocytochemical staining of RGC with βIII-tubulin. For this study, large spherical βIII-tubulin+ retinal cells (Sullivan et al., Annual Review of Cell Biology, 1988. 4: p. 687-716), which can be identified by preferential βIII-tubulin intensity around the axonal base are referred to as RGC. Previous immunocytochemical analysis of these cultures demonstrates that 60% of these retinal cells are neurons (neurofilament+/βIII-tubulin+), of which 10% are Thy1+ RGC (Suggate et al., Molecular and Cellular Neuroscience, 2009. 40(4): p. 451-462).

Figure 8:
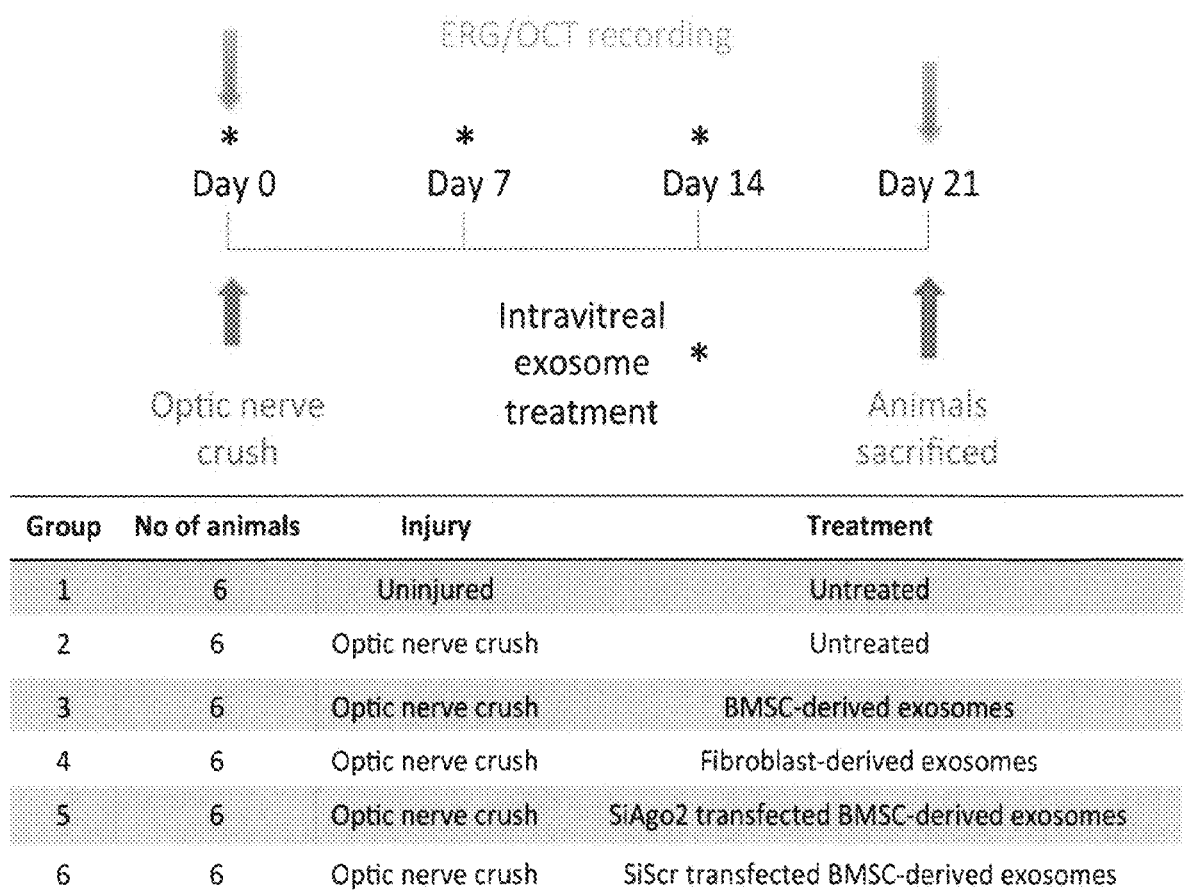
FIG. 8. Experimental design of an in vivo study. Timeline detailing the ERG/OCT recordings, exosome treatments and sacrifice of animals with respect to the day of the optic nerve crush (ONC) surgery. The injury and treatment (asterisks) for each animal group is also given.

In Vivo Experimental Design:

The experimental design is shown in FIG. 8. Briefly, 36 adult rats were divided in the following 6 groups: Group 1, uninjured/untreated; Group 2, ONC/untreated; Group 3, ONC/BMSC-derived exosomes; Group 4, ONC/fibroblast-derived exosomes; Group 5, ONC/SiAgo2 transfected BMSC-derived exosomes; Group 6, ONC/SiScrambled transfected BMSC-derived exosomes. Only 1 eye per animal was used. ONC was performed on day 0 contemporaneously with baseline recordings of electroretinography (ERG)/optical coherence tomography (OCT). Exosome treatments were given on day 0, 7 and 14 and animals were sacrificed on day 21 following ERG/OCT measurements.

Optic Nerve Crush:

Anesthesia was induced with 5% Isoflurane (Baxter Healthcare Corp, Deerfield, Ill.)/1.5 L per minute $O_2$ and maintained at 3.5% throughout the procedure. Following anesthetic induction, an intraperitoneal injection of Buprenorphine (0.3 mg/kg) was administered (pre-operatively) and the animal secured in a heal-holding frame. Intraorbital ONC was performed as previously described (Berry et al., Journal of Neurocytology, 1996. 25(2): p. 147-170). Briefly, the optic nerve was surgically exposed under the superior orbital margin and crushed using fine forceps 1 mm posterior to the lamina cribrosa, taking care to separate the dura mater and under lying retinal artery before crushing.

Intravitreal Delivery of Exosomes:

Deliver of exosomes was done with a 33 g Hamilton syringe (Hamilton Company, Beltsville, Md.), injected into the vitreous just posterior to the limbus. A 5 μl volume of sPBS loaded with $3 \times 10^9$ exosomes was injected slowly and the needle was retracted after 2 minutes to minimize backflow.

Electroretinography (ERG):

ERG records the electrical function of retina in response to a known intensity of light, with different intensities eliciting responses in different retinal cell populations. By eliciting a RGC dependent response, visual function of the glaucomatous rats can be assessed. ERG was recorded using the Espion Ganzfeld full field system (Diagnosys LLC, Lowell, Mass.) before ONC (baseline) and 21 d post-ONC. Rats were dark adapted for 12 hours overnight and prepared for ERG recording under dim red light (>630 nm). Anesthesia was induced with intraperitoneal injection of Ketamine (100 mg/kg; Putney Inc, Portland, Me.)/Xylazine (10 mg/kg; Lloyd Inc, Shenandoah, Iowa) and eyes dilated with tropicamide. Scotopic flash ERG were recorded from −5.5 to +1 log units with respect to standard flash in half log-unit steps.

Erg Analysis:

ERG traces were analyzed using in built Espion software and the amplitude (with respect to baseline) was used as a measure of rat visual function. Traces at a light intensity of $1 \times 10^{-5}$ mcd/s were chosen for analysis as they gave a clean, unambiguous positive scotopic threshold response (pSTR) with a mean latency of 100 ms.

Optical Coherence Tomography Measurements of the Retinal Nerve Fiber Layer:

OCT was performed on rats under anesthesia (Ketamine and Xylazine, as above) pre-ONC (baseline reading) and 21 days post-ONC, before sacrifice and tissue collection. A SPECTRALIS™ HRA3 confocal scanning laser ophthalmoscope (Heidelberg Engineering, Heidelberg, Germany) was used to take images of the retina around the optic nerve head and in-built software segmented the retinal nerve fiber layer (RNFL) and quantified the thickness. Segmentation was manually adjusted when necessary to prevent inclusion of blood vessels that populate the RNFL.

Tissue Preparation:

At 21 day post-ONC, animals were sacrificed by rising concentration of $CO_2$ and perfused intracardially with 4% paraformaldehyde (PFA) in PBS. Eyes and optic nerves were removed and immersion fixed in 4% PFA in PBS for 2 hours at 4° C. before cryoprotection in 10%, 20% and 30% sucrose solution in PBS for 24 hours with storage at 4° C. Eyes and optic nerves were then embedded using optimal cutting temperature embedding medium (VWR International Inc, Bridgeport, N.J.) in peel-away mould containers (VWR International Inc) by rapid freezing under crushed dry ice and were stored at −80° C. After embedding, eyes and optic nerves were sectioned on a CM3050S cryostat microtome (Leica Microsystems Inc, Bannockburn, Ill.) at −22° C. at a thickness of 20 μm and 14 μm, respectively, and mounted on positively charged glass slides (Superfrost Plus, Thermo Fisher Scientific). Longitudinal optic nerve and parasagittal eye sections were left to dry on slides overnight at 37° C. before storage at −20° C. To ensure RGC counts were done in the same plane, eye sections were chosen with the optic nerve head visible.

Immunocytochemistry:

Retinal cells were fixed in 4% PFA in PBS for 10 minutes, washed for 3×10 minutes of PBS, blocked in blocking solution (3% bovine serum albumin (g/ml), 0.1% Triton x-100 in PBS) for 20 minutes and incubated with primary antibody diluted in antibody diluting buffer (ADB; 0.5% bovine serum albumin, 0.3% Tween-20 in PBS) for 1 hour at room temperature. Cells were then washed for 3×10 minutes in PBS, incubated with the secondary antibody diluted in ADB for 1 hour at room temperature, washed for 3×10 minutes in PBS, mounted in VECTORSHIELD® mounting medium containing DAPI (Vector Laboratories) and stored at 4° C.

| Antigen | Dilution | Supplier | Catalogue no. |
| --- | --- | --- | --- |
| RBPMS | 1:500 (IHC) | Thermo Fisher | #ABN-1376 |
| βIII-tubulin | 1:500 (ICC) | Sigma | #T-8660 |
| Ago2 | 1:1000 (WB) | Thermo Fisher | #MA5-14861 |
| HSC70 | 1:5000 (WB) | Santa Cruz | #sc-7298 |
| Mouse IgG HRP | 1:2000 (WB) | GE Healthcare | #NA-931 |
| Guinea Pig IgG 546 | 1:400 (IHC) | Thermo Fisher | #A-11074 |
| Mouse IgG 488 | 1:400 (ICC) | Thermo Fisher | #A-11001 |
| Mouse IgG HRP | 1:2000 (WB) | GE Healthcare | #NA-931 |
| Rabbit IgG HRP | 1:10,000 (WB) | Cell Signalling | #7074 |

Immunohistochemistry:

Mounted tissue sections were equilibrated to room temperature, hydrated in PBS for 2×5 minutes, permeabilised in 0.1% triton x-100 in PBS for 20 minutes at room temperature and washed for 2×5 minutes in PBS before isolation with a hydrophobic PAP pen (Immedge pen, Vector Laboratories). Non-specific protein binding sites in sections were blocked by incubation in blocking buffer (75 μl; 0.5% bovine serum albumin (g/ml), 0.3% Tween-20, 15% normal goat/donkey serum (Vector Laboratories) in PBS) in a humidified chamber for 30 minutes at room temperature and then sections were drained and incubated with primary antibody (see below) diluted in ADB (15% normal goat serum in place of bovine serum albumin) overnight at 4° C. The following day, slides were washed for 3×5 minutes in PBS. Tissue sections were then incubated with secondary antibody diluted in ADB for 1 hour in a hydrated incubation chamber at room temperature. After 1 hour, slides were washed for 3×5 minutes in PBS, mounted in VECTORSHIELD® mounting medium containing DAPI (Vector Laboratories) and stored at 4° C. before microscopic analysis.

| Antigen | Dilution | Supplier | Catalogue no. |
|---|---|---|---|
| RBPMS | 1:500 (IHC) | Thermo Fisher | #ABN-1376 |
| βIII-tubulin | 1:500 (ICC) | Sigma | #T-8660 |
| Ago2 | 1:1000 (WB) | Thermo Fisher | #MA5-14861 |
| HSC70 | 1:5000 (WB) | Santa Cruz | #sc-7298 |
| Mouse IgG HRP | 1:2000 (WB) | GE Healthcare | #NA-931 |
| Guinea Pig IgG 546 | 1:400 (IHC) | Thermo Fisher | #A-11074 |
| Mouse IgG 488 | 1:400 (ICC) | Thermo Fisher | #A-11001 |
| Mouse IgG HRP | 1:2000 (WB) | GE Healthcare | #NA-931 |
| Rabbit IgG HRP | 1:10,000 (WB) | Cell Signalling | #7074 |

Microscopy and Analysis:

All fluorescently stained sections were analyzed by an operator blinded to the treatment groups. For immunocytochemistry, all βIII-tubulin$^+$ retinal cells (identified by their staining morphology and referred to from here on as RGC), with or without neurites, were counted in each well, recording the total number of RGC and the number of RGC with neurites. Fluorescently stained cells were analyzed using a Zeiss LSM 700 confocal laser-scanning microscope (Carl Zeiss Inc, Thornwood, N.Y.). Neurite outgrowth was measured in images taken at 20× magnification. Each well was divided into 9 equal sectors and the length of the longest neurite of each RGC in each sector was measured using Axiovision software (Carl Zeiss Inc). All experiments were repeated on 3 separate occasions with separate animals. Each of the treatment groups in each of the 3 experimental runs comprised 3 replicate wells containing retinal cells harvested from the same animals.

For immunohistochemistry of retina, RBPMS$^+$ and Brn3a$^+$ were counted in 20 µm-thick sections along a 250 µm linear region of the ganglion cell layer (GCL) either side of the optic nerve (as previously described (Mead et al., Plos One, 2014. 9(10): p. e110612.)), imaged using a Zeiss LSM 700 confocal laser-scanning microscope. Six sections per retina and 6 retinae (from 6 different animals) per treatment group were quantified. For immunohistochemistry of the optic nerve, growth associated protein-43$^+$ (GAP-43) axons were counted in 14 µm thick longitudinal sections, imaged using a Zeiss LSM 700 confocal laser-scanning microscope and images composites created using Photoshop CS6 (Adobe Systems, Inc., San Jose, Calif.). The number of axons were quantified at 100 µm distance intervals extending distal to the laminin$^+$ crush site, up to a maximum distance of 1.2 mm. Three sections per optic nerve and 6 optic nerves (from 6 different animals) per treatment group were quantified. The diameter of the nerve was measured at each distance to determine the number of axons/mm width. This value was then used to derive Σad, the total number of axons extending distance d in an optic nerve with radius r using:

$$\sum_{ad} = \pi r^2 \times \frac{\text{average number of axons/mm width}}{\text{section thickness (0.015 mm)}}$$

Statistics:

Animal numbers were determined beforehand using a power calculation (Faul et al., Behav Res Methods, 2007. 39(2): p. 175-91) (GPOWER™) All statistical tests were performed using SPSS 17.0 (IBM SPSS, Inc., Chicago, Ill.) and data presented as mean±standard error of the mean (SEM) with graphs constructed using Graphpad Prism (La Jolla, Calif.). The Shapiro-Wilkes test was used to ensure all data were normally distributed before parametric testing using a one-way analysis of variance (ANOVA) with a Tukey post-hoc test. Statistical differences were considered significant at p values <0.05.

Example 10

BMSC Secrete Exosomes

Figure 9A:
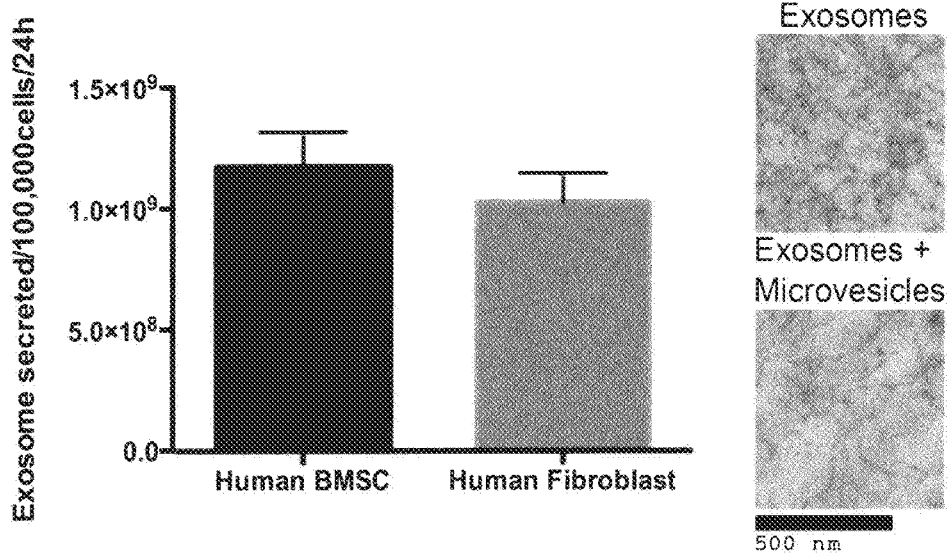
FIGS. 9A-9B. Exosome secretion from fibroblasts and BMSC. (A) The number of exosomes, assayed and quantified by CD63 EXOELISA™, secreted by human fibroblasts and human BMSC, given as exosomes per 100,000 cells, per 24 hours. Numbers were corrected to take into account CD63 expression percentage as determined by flow cytometry. No significant difference was found ($p<0.05$). (B) The percentage of exosomes that express various CD surface expression markers assayed and quantified using a MACSPLE™ Exosome Kit (human) in conjunction with flow cytometry. The surface markers CD2, CD3, CD4, CD14, CD25, CD31, CD40, CD42a, CD45, CD49e, CD56, CD69, CD133/1, CD146 and CD326 were not detected in either sample. Black lines indicate significant difference ($p<0.05$).
Figure 9B:
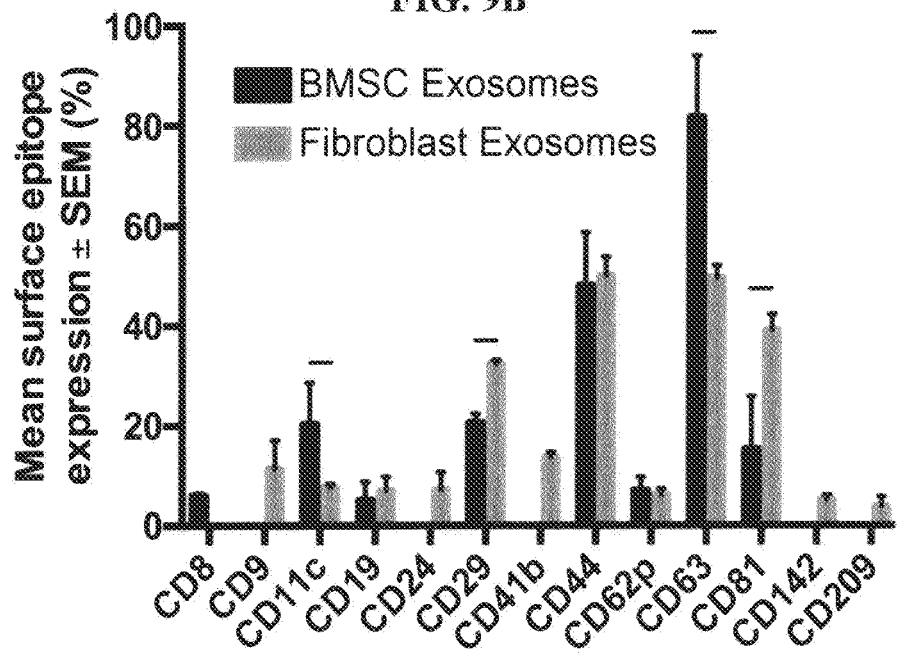

Both human fibroblast and human BMSC secreted exosomes, as detected by electron microscopy and quantified by CD63 EXOELISA™ (FIG. 9A). Exosomes were visualized using electron microscopy and no observable differences were seen between BMSC and fibroblast exosomes but size differences were when comparing exosomes before and after filtration though a 0.22 µm filter to remove microvesicles. As detected by ELISA, secretion rate was not significantly different between BMSC and fibroblasts. Fibroblasts secreted $1.03 \times 10^9 \pm 1.17 \times 10^8$ exosomes whereas BMSC secreted $1.17 \times 10^9 \pm 1.42 \times 10^8$, measured over a 24 hour time point and normalized to 100,000 cells. Using flow cytometry, the surface expression of various CD molecules on exosomes from BMSC and fibroblasts (FIG. 2B) was analyzed. In this study 13 different CD molecules variably expressed on BMSC and/or fibroblast exosomes were detected. In particular, more CD11c$^+$ and CD63$^+$ exosomes were detected on the BMSC exosomes (20.3±8.3%, 81.7±12.3%, respectively) compared to fibroblast exosomes (7.7±0.7, 49.6±2.4, respectively) whereas more CD29$^+$ and CD81$^+$ exosomes were detected on fibroblast exosomes (32.4±0.75%, 39±3.3%, respectively) compared to BMSC exosomes (20.5±1.9%, 15.3±10.6%, respectively). CD1c, CD2, CD3, CD4, CD14, CD20, CD25, CD31, CD40, CD42a, CD45, CD49e, CD56, CD69, CD133/1, CD146 and CD326 were undetectable. Due to the differences in the number of exosomes expressing CD63, exosome counts (FIG. 9A) were normalized using this data.

Example 11

BMSC-Derived Exosomes Promote Neuroprotection and Neuritogenesis of Cultured Primary RGC Treatment of RGC cultures with $3 \times 10^9$ BMSC EV (exosomes+microvesicles) elicited optimum significant survival (FIG. 10A) of RGC (321±22.3 RGC/well) compared to untreated RGC (121.3±6.2)/$3 \times 10^9$ fibroblast EV treated RGC (72.3±6.4) and was similar to treatment with 50,000 BMSC (328±24 RGC/well). At higher doses of BMSC EV ($1.5 \times 10^{10}$, $7.5 \times 10^{10}$), RGC neuroprotection was significantly reduced (202.7±10.7, 58±14.4 RGC/well, respectively) unless microvesicles were first removed from the sample (leaving exosomes), in which case higher doses were still equally neuroprotective (299±24.1, 270.3±47.3 RGC/well, respectively).

Neuritogenesis was measured both as the number of neurite-bearing RGC (FIG. 10B) and the average length of the longest neurites (FIG. 10C). Treatment of RGC cultures with $3 \times 10^9$ BMSC EV elicited optimum neuritogenesis of RGC (154±4 RGC with neurites; 114.2±5 µm) compared to untreated RGC (32.3±3.5 RGC with neurites; 43.7±6.9 µm)/$3 \times 10^9$ fibroblast EV treated RGC (25.7±3.3 RGC with neurites; 45.2±4.1 µm) and was similar to treatment with 50,000 BMSC (166.7±11.3 RGC with neurites; 186.3±21.8 µm). At higher doses of BMSC EV ($1.5 \times 10^{10}$, $7.5 \times 10^{10}$), RGC neuritogenesis was significantly reduced (27.3±4.4, 11.7±3.5 RGC with neurites; 54.8±2.4, 42.7±2 respectively)

unless microvesicles were first removed from the sample (leaving exosomes), in which case higher doses were still equally neurotogenic (128.7±16.0, 109.3±18.8 RGC with neurites; 127.9±5.2, 140.1±15.5 respectively). Increasing or decreasing the number of control fibroblast-derived exosomes/EV did not have any significant effect on neuroprotection and neuritogenesis.

Example 12

BMSC-Derived Exosomes Preserve RNFL Thickness Following ONC

The thickness of the RNFL is a measure of RGC axonal density and did not change over 21 days in intact animals as well as between groups pre-ONC. In untreated animals, RNFL thickness decreased significantly from 48.2±1.3 μm to 18.0±2.1 μm 21 days after ONC (FIGS. 11A-11B). In animals receiving BMSC-derived exosomes, RNFL thickness was reduced from 48.4±2.9 μm to 33.8±4.8 μm 21 days after ONC, which was a significantly smaller reduction in comparison to both untreated animals and animals receiving fibroblast-derived exosomes (21.6±1.5 μm). In animals receiving exosomes derived from SiAgo2 transfected BMSC (knockdown confirmed by Western blot; FIG. 11B), RNFL thickness decreased significantly from 46.0±2.2 μm to 22.0±2.2 μm whereas in animals receiving exosomes derived from SiScr transfected BMSC, post-ONC RNFL was, in comparison, significantly higher (32.4±5.3 μm).

Example 13

BMSC-Derived Exosomes Successfully Integrate and Deliver Cargo to RGC In Vivo

To determine the fate of exosomes after delivery into the vitreous body they were tracked by the internalization of a fluorescent marker (ExoGreen) prior to injection. Fluorescent labelling was seen in the RNFL and GCL in a nonspecific manner. RBPMS$^+$ RGC along with the RNFL and resident cells (morphologically identified as astrocytes) incorporated exosomes and thus were labelled strongly with ExoGreen (FIG. 12B).

Example 14

BMSC-Derived Exosomes Promote Neuroprotection of RGC Following ONC

ONC induced a significant loss of RBPMS$^+$ and Brn3a$^+$ RGC by 21 day (23.6±7.7 and 29.1±7.8/mm of retina, respectively) compared to intact controls (103.1±6.9 and 75.5±3.9/mm of retina, respectively; FIGS. 12A-12B). Intravitreal transplantation of 3×10$^9$ BMSC exosomes provided significant neuroprotection for RBPMS$^+$ and Brn3a$^+$ RGC (73.3±7.8 and 54±8.2/mm of retina, respectively) compared to controls receiving fibroblast exosomes (20±2.2 and 14.3±7.4/mm of retina, respectively). Intravitreal transplantation of exosomes-derived from SiAgo2 transfected BMSC failed to significantly protect RBPMS$^+$ and Brn3a$^+$ RGC (11.63±1.1 and 4.42±0.4/mm of retina, respectively) whereas exosomes derived from SiScr transfected BMSC were significantly RGC neuroprotective.

Example 15

BMSC-Derived Exosomes Preserve RGC Function

Figure 13A:
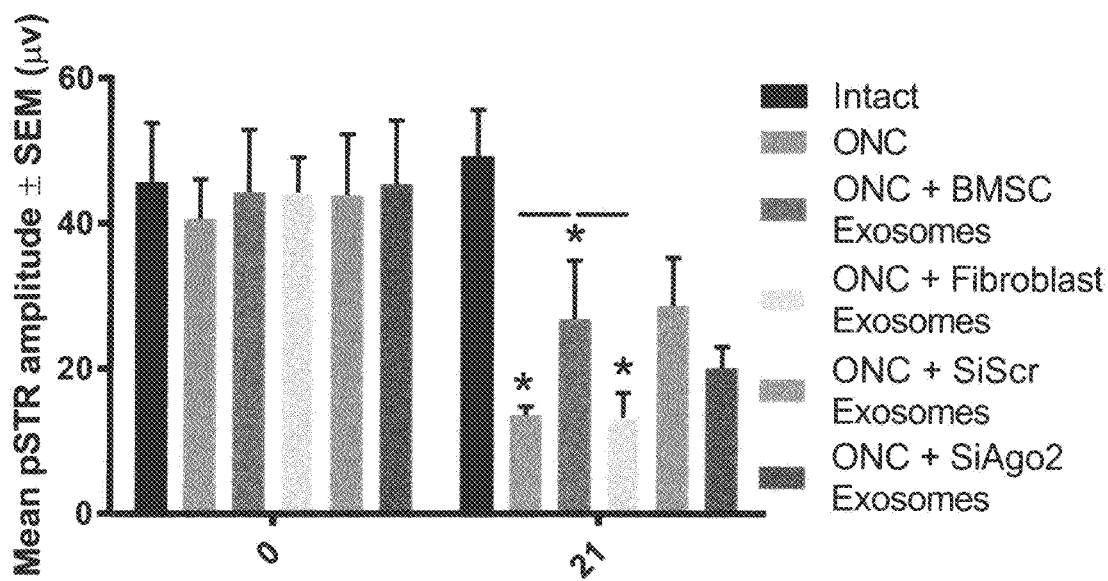
FIGS. 13A-13B. pSTR responses after ONC and exosome treatment. (A) Mean amplitude of pSTR from intact or ONC animals receiving intravitreal exosome treatments after receiving flash intensity of $1\times10^{-5}$ mcd/s. Black lines indicate significant difference between groups whereas asterisks indicate significant difference from the same group pre-ONC ($p<0.05$). (B) Representative traces of observable pSTR from groups 1-6.
Figure 13B:
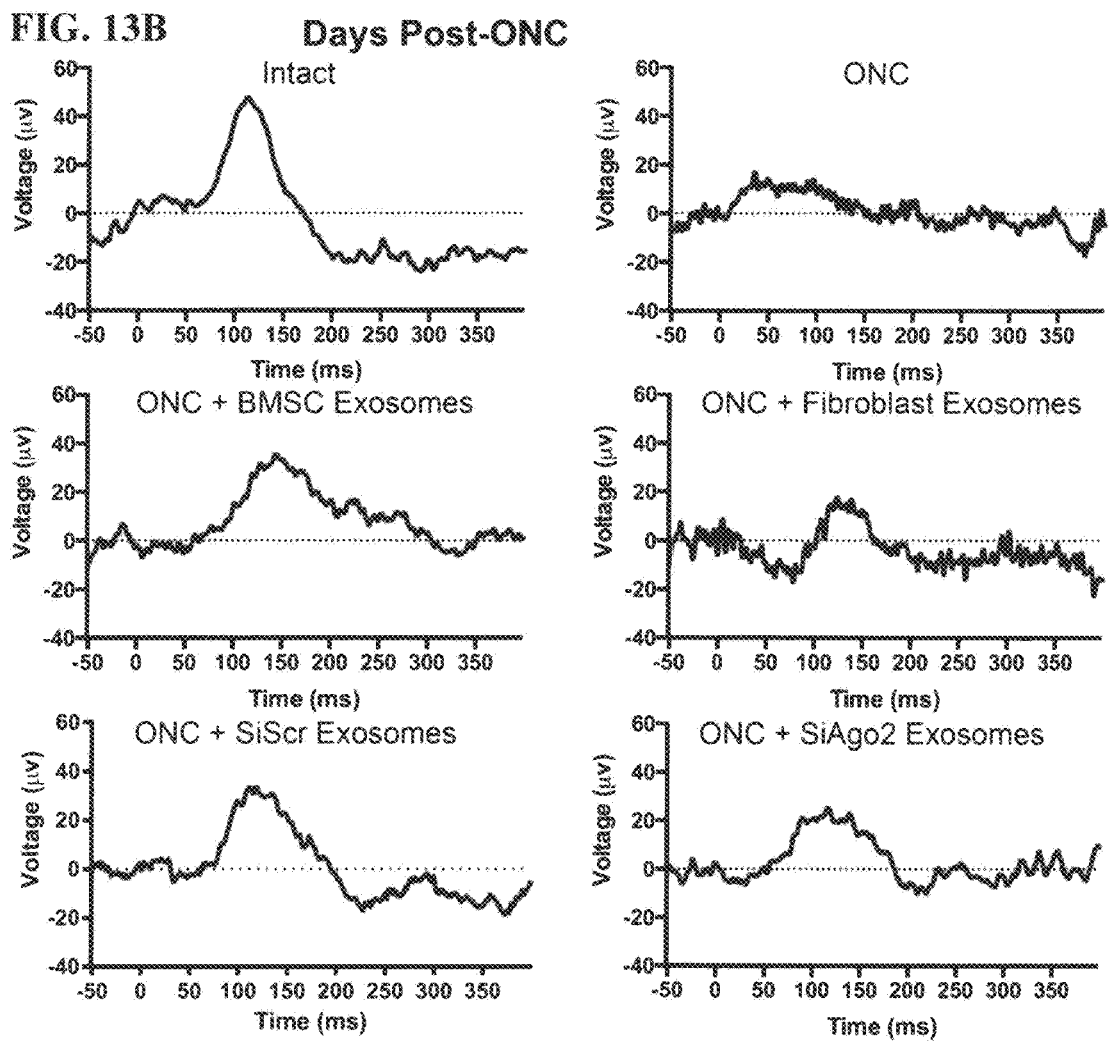

The amplitude of the pSTR is a measure of RGC function and did not change over 21 days in intact animals as well as between groups pre-ONC (FIG. 13). In untreated animals, pSTR amplitude decreased significantly from 48.7±5.5 μv to 13.7±1.1 μv 21 days after ONC. In animals receiving BMSC-derived exosomes, pSTR amplitude was reduced from 44.3±8.6 μv to 28.6±8.1 μv 21 days after ONC, which was a significantly smaller reduction in comparison to both untreated animals and animals receiving fibroblast-derived exosomes (13.2±3.4 μv). In animals receiving exosomes derived from SiAgo2 transfected BMSC, pSTR amplitude decreased significantly from 45.4±8.7 μv to 20.12±2.9 μv whereas in animals receiving exosomes derived from SiScr BMSC, post-ONC pSTR amplitude was, in comparison, significantly higher (28.7±6.6 μv).

Example 16

BMSC-Derived Exosomes Promote Regeneration of RGC Axons Following ONC

Intravitreal transplantation of 3×10$^9$ BMSC exosomes promoted significant regeneration of GAP-43$^+$ axons up to 600 μm from the laminin$^+$ crush site compared to untreated controls/controls receiving fibroblast exosomes (FIG. 14). Intravitreal transplantation of exosomes-derived from SiAgo2 transfected BMSC failed to promote significant regeneration of GAP-43$^+$ axons whereas exosomes derived from SiScr transfected BMSC were significantly RGC axogenic.

Thus, RGC were treated with exosomes, and BMSC-derived exosomes were delivered into the eye in an animal model to confirm their effect in vivo. Utilizing the ONC model of CNS injury that is characterized by RGC death and a failure of axon regeneration, a significant neuroprotective and axogenic effect was afforded by BMSC-derived exosomes, and they had the capacity to preserve retinal function. Thus, exosomes successfully deliver their cargo to the inner retina, including the RGC and elicit therapeutic effects through miRNA dependent mechanisms.

RGC are CNS neurons and thus are neither replaceable nor capable of axon regeneration. While BMSC have proven effective as neuroprotective and axogenic agents, it is more clinically translational to purify and use their cell-free active compounds. As exosomes contain proteins, mRNA and miRNA, they possess the potential to not only deliver proteins and translatable mRNA but also the silencing of genes through RNA interference (Ching et al., Neural Regen Res, 2015. 10(5): p. 743-7). Exosomes can be isolated through simple centrifugation techniques (Thery et al., Curr Protoc Cell Biol, 2006. Chapter 3: p. Unit 3 22) enabling the generation of a cell-free therapy, combining the benefits of BMSC-mediated paracrine repair without the risks (Sun et al., Cytotherapy, 2016. 18(3): p. 413-22.0. They can also be easily stored and do not proliferate, making the application of specific doses easier. Due to their size, they are also capable of migrating into the GCL from the vitreous (unlike transplanted cells) and delivering their content to the RGC. The surrounding phospholipid bilayer of exosomes protects the contents against degradation and makes them immunologically inert, qualities important for a therapeutic delivery system (Sun et al., Advanced Drug Delivery Reviews, 2013. 65(3): p. 342-347).

It was demonstrated that BMSC secrete exosomes and to similar quantities of that of fibroblast controls. There were distinct differences between exosomes from BMSC and fibroblasts, reflected in their surface epitope expression.

Culture of injured RGC is an effective in vitro model of RGC death and abortive axonal regeneration, and has been used extensively (Lorber et al., Journal of Neuroscience Research, 2008. 86(4): p. 894-903; Douglas et al., Brain, 2009. 132: p. 3102-3121) such as demonstrating the neuroprotective and neuritogenic properties of BMSC (Mead et al., Plos One, 2014. 9(10): p. e109305). It was demonstrated that BMSC-derived exosomes are efficacious. Other studies have demonstrated a neuritogenic effect of BMSC exosomes on cortical neurons, although survival was not assessed (Zhang et al., *Exosomes Derived from Mesenchymal Stromal Cells Promote Axonal Growth of Cortical Neurons*. Mol Neurobiol, 2016; Lopez et al., Neuroscience, 2016. 320: p. 129-39). Filtration and removal of microvesicles from the samples negated a dose-dependent negative effect; exosomes purified from EV were effective in the in vivo experiments.

ONC is a reliable model characterized by substantial RGC death and axonal degeneration. A typical 80-90% RGC loss was observed 21 days after ONC (Mead et al., Plos One, 2014. 9(10): p. e110612; Berkelaar et al., J Neurosci, 1994. 14(7): p. 4368-74) in untreated retina whereas treatment with BMSC-derived exosomes reduced RGC loss to 30%. This is significantly higher neuroprotection than that observed with BMSC transplants (Mead et al., Invest Ophthalmol Vis Sci, 2013. 54(12): p. 7544-56; Mesentier-Louro et al., Plos One, 2014. 9(10): p. e110722). Although RBPMS stained more RGC than Brn3a (owing to the presence of Brn3a$^-$ RGC subtypes (Mead et al., Exp Eye Res, 2016. 151: p. 96-106), the relative differences between groups remained the similar.

BMSC do not survive the long term vitreal transplantation, particular as they lack the capacity to integrate into the retina and thus remain in the vitreous. Therefore despite actively secreting NTF (Mead et al., Plos One, 2014. 9(10): p. e109305) as well as exosomes, the titers are likely low and diminish with time. In contrast, exosomes are easily isolated, purified and can be delivered at high doses, and were significantly more effective at preventing RGC death.

By labelling the protein cargo of exosomes before intravitreal injection, the exosomes were tracked to identify which retinal cells they fused with. A strong staining was observed consistently through the RNFL and GCL of the retina. Exogreen labelling co-localized with the RNFL, RBPMS$^+$ RGC and RBPMS$^-$ cells morphologically resembling astrocytes.

The significant neuroprotection afforded by BMSC exosomes was corroborated by the OCT and ERG data, demonstrating a significant protection of RGC axons (measured as RNFL thickness) and preservation of RGC function (measured as pSTR amplitude). A residual function was seen in untreated and fibroblast exosome treated control retina after ONC, likely explained by the presence of select subtypes of RGC that are resistant to ONC (Duan et al., Neuron, 2015. 85(6): p. 1244-56). However, in BMSC exosome treated retina, over 50% of RGC function was maintained, suggesting a strong effect not only to protect RGC from death but also to retain their function.

The neurite outgrowth seen in the present study when retinal cultures were treated with BMSC-derived exosomes was corroborated by their efficacy to promote regeneration of GAP-43$^+$ axons after ONC. The regeneration was significant at short distances from the lesion site (<1 mm).

Exosomes contain both proteins and miRNA. It was determined which was the active compound by using SiAgo2. Ago2 regulates the biological function of miRNA (Ha et al., Nat Rev Mol Cell Biol, 2014. 15(8): p. 509-24), is bound to miRNA (Guduric-Fuchs et al., BMC Genomics, 2012. 13: p. 357) and its knockdown reduces miRNA quantity within exosomes (Zhang et al., Mol Neurobiol, 2016 54: 2659-2673; Guduric-Fuchs et al., BMC Genomics, 2012. 13: p. 357). Ago2 was successfully knocked down and it was demonstrated that BMSC exosomes had a significantly muted effect in promoting RGC neuroprotection, axon regeneration/survival and RGC functional preservation. These data strongly suggest that treating RGC with exosomes is dependent on miRNA. BMSC exosomes contain a variety of miRNA (Baglio et al., Stem Cell Res Ther, 2015. 6: p. 127; Qian et al., Stem Cells Transl Med, 2016. 5: 1190-1203; Eirin et al., Gene, 2014. 551(1): p. 55-64).

One candidate is miR-17-92 cluster which is located within BMSC-derived exosomes (Zhang et all, Mol Neurobiol, 2016. 54: 2659-2673) and has been found to target and down regulate phosphatase and tensin homolog (PTEN) expression, an important suppressor of RGC axonal growth and survival (Park et al., Science, 2008. 322(5903): p. 963-966; Berry et al., Neurobiol Dis, 2016. 85: p. 99-110). Similarly, miR-21, which is expressed in umbilical cord MSC-derived exosomes (Qian et al., Stem Cells Transl Med, 2016) has been shown to regulate PTEN expression (Meng et al., Gastroenterology, 2007. 133(2): p. 647-58). Another candidate miRNA is miR-146a which is expressed in BMSC exosomes (Baglio et al., Stem Cell Res Ther, 2015. 6: p. 127) and targets the epidermal growth factor receptor (EGFR) mRNA (Katakowski et al., Cancer Lett, 2013. 335(1): p. 201-4). Activation of EGFR inhibits axon regeneration whereas receptor blockade promotes RGC axon regeneration (Douglas et al., Brain, 2009. 132: p. 3102-3121; Koprivica et al., Science, 2005. 310(5745): p. 106-10). Activation of the Akt pathway has also been reported by BMSC-derived exosomes (Gu et al., Mol Med Rep, 2016), which is a pathway integral to the survival and regeneration of injured RGC (Berry et al., Restorative Neurology and Neuroscience, 2008. 26(2-3): p. 147-174).

Thus, it was documented that BMSC-derived exosome offer significant therapeutic benefit to the protection of RGC, an effect mediated by their miRNA rather than protein content. Exosomes offer a cell-free alternative to BMSC therapy, and can be easily isolated, purified and stored. Exosomes lack the risk of complications associated with transplanting live cells into the vitreous (immune rejection, unwanted proliferation/differentiation).

Example 17

Mesenchymal Stem Cell-Derived Small Extracellular Vesicles Promote Neuroprotection in a Genetic DBA/2J Mouse Model of Glaucoma It was demonstrated that BMSC exosomes (as included in small extracellular vesicles, sEV) are efficacious in a long-term glaucoma model, using a monthly treatment regime.
Methods
Animals:
Sixty adult female 3-month-old DBA/2J mice (Jackson Laboratories, Bar Harbor, Me., USA) were used for this study as they develop ocular hypertension sooner and to a greater degree than males (Libby et al., *Visual neuroscience*. 2005; 22:637-648). Animals were kept at 21° C./55% humidity under a 12 hours light/dark cycle, given food/water ad libitum and were under constant supervision from trained staff. Animals were euthanized by rising concentrations of $CO_2$ before dissection of retinae and optic nerves.
Materials:
All reagents were purchased from Sigma (Allentown, Pa., USA) unless otherwise specified.

BMSC Cultures:

Human CD29+/CD44+/CD73+/CD90+/CD45− BMSC (confirmed by supplier; Lonza, Walkersville, Md., USA) from three pooled donors were cultured in DMEM/1% penicillin/streptomycin/10% exosome-depleted fetal bovine serum (Thermo Fisher Scientific, Cincinnati, Ohio, USA). Cell cultures were maintained at 37° C. in 5% $CO_2$ with medium changed every 3 days and cells passaged with 0.05% trypsin/EDTA when 80% confluent. Human dermal fibroblasts (Lonza), which were used as control cells were grown in the above conditions and used as a control. For all experiments, BMSC and dermal fibroblasts were used at passage 2-5.

Exosome/sEV Isolation and Quantification:

Exosomes were isolated from BMSC and fibroblasts using a polyethylene glycol (PEG) solution (ExoQuick-TC; System Biosciences, Mountain View, Calif., USA) per the manufacturer's instructions. Briefly, conditioned medium was centrifuged at 3000 g for 15 minutes to remove cells and debris, incubated with EXOQUICK® reagent overnight at 4° C. (1:10 ratio with medium), centrifuged at 1500 g for 15 minutes before resuspension of the exosome pellet in sterile phosphate-buffered saline (PBS). The exosome preparation is passed through a 0.22 µm filter to remove any large extracellular vesicles (microvesicles and apoptotic bodies). PEG precipitation techniques yield some non-exosomal vesicles in the preparation. Thus, the exosomes used in this study are referred to as small exosomal vesicles, sEV. The sEV were characterized by their positive staining for the exosome/microvesicle markers Syntenin-1 and CD63 and negative staining for high/low density lipoprotein markers ApoA1 and ApoB using Western blot (Mead et al., *Investigative Ophthalmology & Visual Science*. 2018; 59:702-714) To ensure a consistent delivery amount, sEV were quantified using a NANOSIGHT® LM10 instrument (Malvern, Worcester, Mass., USA).[10] Briefly, for each sample, three videos were captured and analyzed at a detection threshold of 2, 12.9- to 13.1-pix maximum jump size, automatic blur size, slider gain at 80 and with a total of 567 frames per video.

In Vivo Experimental Design:

Sixty DBA/2J mice were separated into three groups: Group 1 consisted of 20 untreated mice; Group 2 consisted of 20 mice injected monthly with BMSC sEV; Group 3 consisted of 20 mice injected monthly with fibroblast sEV. The experiment began with 3-month-old mice and they were euthanized at 12 months. Six mice died towards the end of the experiment, likely due to their old age in combination with anesthesia. DBA/2J mice are known to suffer from colony specific problems including heart calcifications and thoracic cavity malformations which are expected to lead to sudden death in a number of animals before the study concludes (Turner et al., *Clinical & Experimental Ophthalmology*. 2017; 45:911-922).

The group with the smallest final count was 17 mice and the other 2 groups thus provided 17 mice randomly from their cohort to maintain consistency. Since each eye develops ocular hypertension independent of the contralateral eye (Turner et al., *Clinical & Experimental Ophthalmology*. 2017; 45:911-922) they are thus treated as independent samples (Libby et al., *Visual neuroscience*. 2005; 22:637-648), resulting in n=34 per group. RGC/axonal survival was assessed histologically whereas function was measured via electroretinography (ERG). Optical coherence tomography was not performed as images were of extremely poor quality making analysis unfeasible in aged DBA/2J mice due to the iris atrophy and irregularly shaped pupil that was not amenable to tropicamide-mediated dilation. Oculomotor response testing was not conducted as DBA/2J mice show no response to these tests (Barabas et al., *Invest Ophthalmol Vis Sci*. 2011; 52:6766-6773).

Intraocular pressure recording (IOP):

IOP was recorded for all mice using a Tonolab rebound tonometer (Colonial Medical Supply, Franconia, N.H., USA). IOP was recorded under isoflurane-induced anesthesia between 8-11 am, sampled 18 times and averaged for each individual recording. Recordings were performed monthly, from age 3 to 12 months and were taken just prior to the monthly intravitreal (ivit) injection. DBA/2J mice are known to develop corneal calcifications making tonometry recording of IOP unreliable (Turner et al., *Clinical & Experimental Ophthalmology*. 2017; 45:911-922). Care was taken to avoid recording IOP in obvious calcified regions while still ensuring the probes point of contact is perpendicular to the cornea.

Intravitreal Delivery of sEV:

Under isoflurane-induced anesthesia, sEV were injected into the vitreous, just posterior to the limbus using glass micropipettes. A 2 µl volume of sPBS loaded with $1\times10^9$ sEV was injected slowly and the needle was retracted only after a 1-minute delay to minimize backflow. The concentration was chosen based on our previous studies (Mead et al., *Investigative Ophthalmology & Visual Science*. 2018; 59:702-714; Mead et al., *Stem cells translational medicine*. 2017; 6:1273-1285, incorporated herein by reference) that demonstrated efficacy with the volume and concentration adapted for the mouse vitreous volume. Injections were performed once a month, from 3 to 12 months.

Electroretinography Measurements of the Positive Scotopic Threshold Response:

ERG was recorded using the ESPION® Ganzfeld full field system (Diagnosys LLC, Lowell, Mass., USA) on 3-month-old mice, before any detectable ocular hypertension or functional decline (Libby et al., *Visual neuroscience*. 2005; 22:637-648; Turner et al., *Clinical & Experimental Ophthalmology*. 2017; 45:911-922; Saleh et al., *Investigative ophthalmology & visual science*. 2007; 48:4564-4572) and on mice aged 6, 9 and 12 months, when RGC function is expected to deteriorate. Mice were dark adapted for 12 hours and prepared for ERG recording under dim red light (>630 nm). Anesthesia was induced with intraperitoneal injection of Ketamine/Xylazine and eyes dilated with tropicamide. Scotopic flash ERG was recorded from −5.5 log (cd s) $m^{-2}$ to 1.0 log (cd s) $m^{-2}$ in 0.5 log unit increments. ERG traces were analyzed using in built EPISON® software and the amplitude (with respect to baseline) was used as a measure of mouse visual function. Traces at a light intensity of −5.0 log (cd s) $m^{-2}$ were chosen for analysis as they produced a clean, unambiguous pSTR at approximately 100 ms after stimulus, of which the peak amplitude was recorded. While it is possible corneal calcifications may have affected the RGC traces, it is expected this effect will be universal for all groups and equally. Thus, it was possible to measure pSTR in mice aged 12 months. All readings and analysis were performed by an individual masked to the treatment groups.

Tissue Processing:

Mice were euthanized at 12 months by rising concentration of $CO_2$ and immediately perfused intracardially with 4% paraformaldehyde (PFA) in PBS. Eyes were enucleated and retinae dissected and immersion post-fixed in 4% PFA for 1 hour at 4° C. Optic nerves were dissected, cryopreserved in 10, 20 and 30% sucrose solution in PBS for 24 hours at 4° C. Optic nerves were embedded in optimal cutting temperature embedding medium (VWR International Inc, Bridgeport, N.J., USA) in peel-away mold containers (VWR International Inc) and stored at −80° C. Optic nerves were coronally sectioned on a CM1860 Cryostat microtome (Leica Microsystems Inc, Bannockburn, Ill.) at −20° C. at a thickness of 5 µm, mounted on positively charged glass slides (SUPERFROST PLUS®, Fisher Scientific, Pittsburgh, Pa., USA) and stored at −80° C. until required.

RGC Counts in Retinal Wholemounts:

Retinal wholemounts were permeabilized by immersion in 0.5% TRITON® X-100 in PBS for 15 minutes at −70° C., washed in fresh TRITON® X-100 for a further 15 minutes before incubation with primary antibody diluted in wholemount antibody diluting buffer (wADB: 2% bovine serum albumin, 2% Triton X-100 in PBS) overnight at 4° C. The following day, wholemounts were washed for 3×10 minutes in PBS and incubated with secondary antibodies in wADB for 2 hours at room temperature. After 2 hours, retinae were washed for 3×10 minutes in PBS and mounted vitreous side up on SUPERFROST PLUS® glass slides, facilitated by 4 equidistant cuts into the peripheral retina. Slides were allowed to air dry before mounting in VECTORSHIELD® medium (Vector Laboratories, Peterborough, UK) and applying cover slips. The antibodies used are detailed below.

| Antigen | Dilution | Supplier | Catalogue no. |
|---|---|---|---|
| RBPMS | 1:500 (IHC) | Thermo Fisher | #ABN-1376 |
| Syntentin-1 | 1:1000 (WB) | Abcam | #Ab133267 |
| CD63 | 1:1000 (WB) | System Bio | #Exoab-CD63-A1 |
| ApoA1 | 1:1000 (WB) | Abcam | #ab7613 |
| ApoB | 1:1000 (WB) | Abcam | #ab20737 |
| HSC70 | 1:5000 (WB) | Santa Cruz | #sc-7298 |
| Mouse IgG HRP | 1:2000 (WB) | GE Healthcare | #NA-931 |
| Guinea Pig IgG 546 | 1:400 (IHC) | Thermo Fisher | #A-11074 |
| Mouse IgG HRP | 1:2000 (WB) | GE Healthcare | #NA-931 |
| Rabbit IgG HRP | 1:10,000 (WB) | Cell Signalling | #7074 |

Retinal wholemounts were imaged using a Z1 Imager epifluorescent microscope equipped with an AXIOCAM® HRc camera (Carl Zeiss Inc, Thornwood, N.Y., USA) and RNA binding protein with multiple splicing (RBPMS)$^+$ cells were counted in three 0.33 mm$^2$ regions per retinal quadrant at 0.5, 1 and 1.5 mm from the optic nerve head. Counts were conducted manually by an individual masked to the treatment group. The mean number of RGC/image was derived from the 12 images which made up 8.3% of the total retina (16 mm$^2$) (Salinas-Navarro et al., *Vision Res.* 2009; 49:637-647) and was used to calculate RGC/mm$^2$ with each group consisting of 34 retinae from 17 mice.

Glaucomatous Damage Scaling in Optic Nerve Section:

Glaucomatous damage in the optic nerve was assessed as previously described (Libby et al., *Visual neuroscience.* 2005; 22:637-648; Libby et al., *PLOS Genetics.* 2005; 1:e4; Smith et al., Boca Raton: CRC Press; 2002). Briefly, optic nerves were stained in 1% paraphenylenediamine (PPD) in 1:1 propanol/methanol for 30 minutes at room temperature, washed in ethanol and allowed to air-dry before being mounted in PERMOUNT® (Thermo Fisher Scientific). PPD darkly stains the axoplasm of damaged axons and optic nerves were graded as mild, moderate or severe damage by two investigators masked both from the treatment group as well as each other's grades. Approximately 20 sections were analyzed per optic nerve. The grading scale followed previous guidelines (Libby et al., *Visual neuroscience.* 2005; 22:637-648; Libby et al., *PLOS Genetics.* 2005:1:e4). Briefly, mild represents optic nerves with less than 5% of damaged axons and no gliosis; moderate represents optic nerves with 5-30% axonal loss and early gliosis; severe represents optic nerves with over 50% axonal loss and prominent gliosis. Since there is overlap, a third masked investigator was used if the initial two investigators disagreed on the grading.

Statistics:

All statistical tests were performed using SPSS 17.0 (IBM SPSS, Inc., Chicago, Ill., USA) and data presented as mean±standard error of the mean with graphs constructed using GRAPHPAD PRISM® 7.01 (GRAPHPAD PRISM®, La Jolla, Calif., USA). The Shapiro-Wilkes test was used to ensure all data were normally distributed before parametric testing using a one-way analysis of variance (ANOVA) with a Tukey post-hoc test. Graded optic nerves were compared using a Fisher's Exact test (2×3). Statistical differences were considered significant at p values <0.05.

Results

Figure 15:
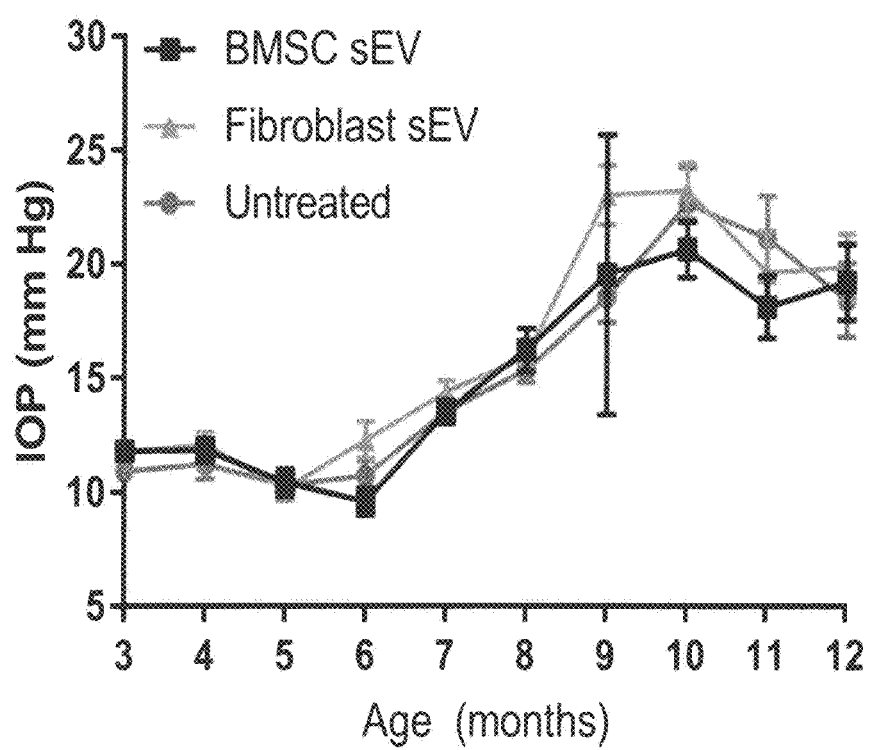
FIG. 15. Intraocular pressure (IOP) measurements in DBA/2J mice. Mean (±SEM) IOP (mm Hg) of untreated animals and animals receiving ivit injection of BMSC- or fibroblast-derived sEV. No significant difference ($p>0.05$) between untreated and experimental groups was found.

DBA/2J Mice Spontaneously Develop Ocular Hypertension:

DBA/2J mice maintained normal IOP (10-12 mm Hg) between 3-6 months (FIG. 15). At 7 months, IOP increased spontaneously to 13.6±0.5 mm Hg, 13.5±0.5 mm Hg and 14.4±0.5 mm Hg in untreated, BMSC sEV treated and fibroblast sEV treated DBA/2J mice, respectively. By 12 months, IOP increased to 18.4±1.6 mm Hg, 19.3±1.7 mm Hg and 19.9±1.5 mm Hg in untreated, BMSC sEV treated and fibroblast sEV treated DBA/2J mice, respectively. IOP did not significantly differ between the 3 groups at any age, suggesting that BMSC/fibroblast sEV do not affect IOP in DBA/2J mice.

Figure 16A:
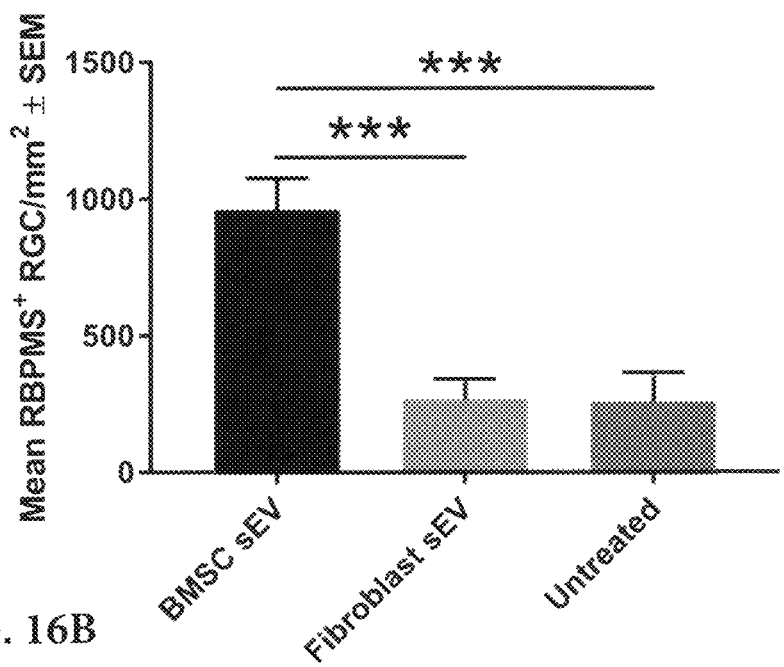
FIGS. 16A-16B. Surviving RBPMS⁺ RGC counts in DBA/2J mice. (A) Quantification of the mean (±SEM) number of surviving RBPMS⁺ RGC in 12-month-old DBA/2J mice with or without ivit injection of BMSC- or fibroblast-derived sEV. Asterisks indicate significant difference between groups ($p<0.001$). (B) Representative images of RBPMS⁺ RGC from immunohistochemically stained retinal wholemounts (scale bar: 100 μm).
Figure 16B:
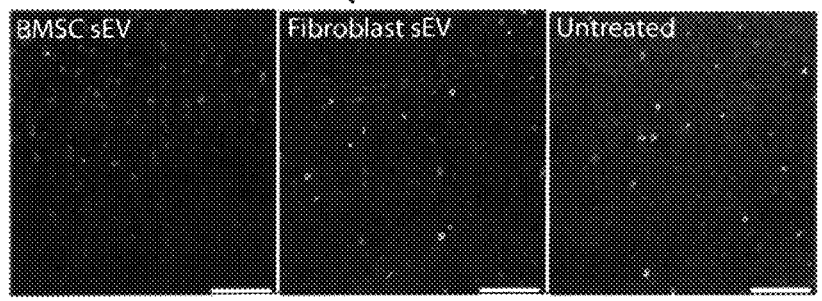

BMSC sEV are Neuroprotective in DBA/2J Mice:

Quantification of the number of RBPMS$^+$ RGC at 12 months in retinal wholemounts of BMSC sEV treated DBA/2J mice (962±116 RGC/mm$^2$) was significantly higher (p<0.001) than those of fibroblast sEV treated mice (268±72 RGC/mm$^2$) or untreated mice (259±106 RGC/mm$^2$; FIG. 16). Therefore, BMSC sEV protect 3.7-fold greater numbers of RBPMS$^+$ RGC compared to untreated mice. BMSC sEV are RGC neuroprotective in DBA/2J mice.

BMSC sEV Prevent RGC Functional Decline at 6 Months, but not 9 or 12 Months:

The amplitude of the pSTR was 47.3±2.1 µV in DBA/2J mice age 3 months (FIG. 17). By 6 months, pSTR amplitude in BMSC sEV treated DBA/2J mice had decreased (33.2±3.0 µV) but remained significantly higher than that in fibroblast sEV treated mice (22.9±1.8 µV) or untreated mice (26.3±2.4 µV). By 9 and 12 months, pSTR amplitudes in BMSC sEV treated (24.9±2.4 µV and 19.7±2.6 µV, respectively), fibroblast sEV treated (20.5±2.7 µV and 15.6±3.1 µV, respectively) and untreated (18.5±2.2 µV and 16.1±3.2 µV, respectively) DBA/2J mice had decreased further but there was no longer a significant difference between groups. These results demonstrate that BMSC sEV prevent the early decline in RGC function but cannot prevent later decline in RGC function in DBA/2J mice.

Figure 18A:
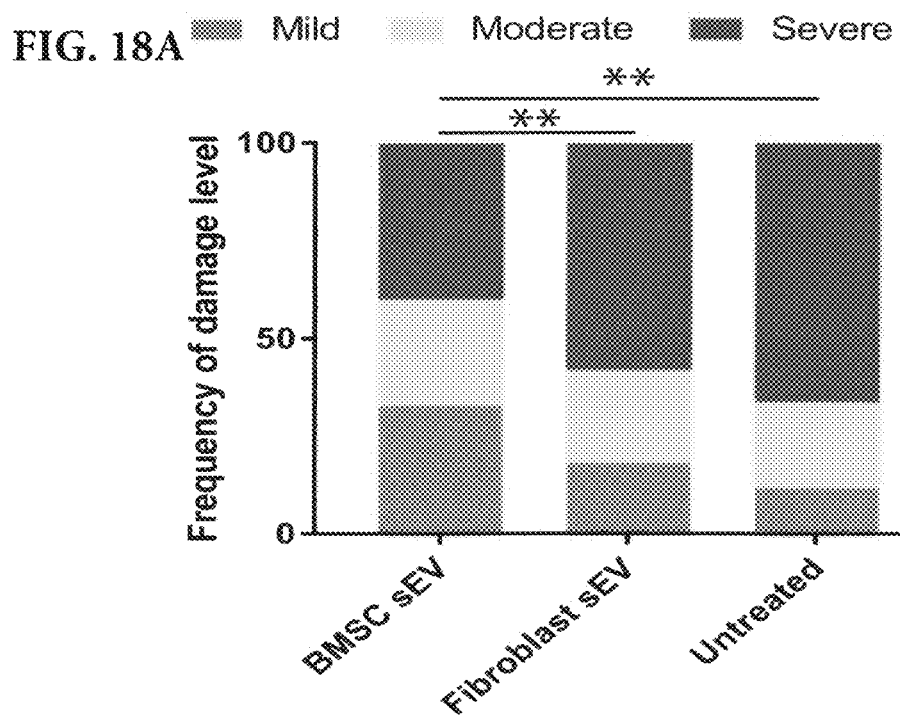
FIGS. 18A-18C. Frequency distribution of glaucomatous optic nerve damage in DBA/2J mice. (A) Frequency of damage, defined as Mild, Moderate, or Severe and represented as a percentage of the total number of analyzed optic nerve sections from 12-month-old DBA/2J mice with or without ivit injection of BMSC- or fibroblast-derived sEV. Asterisks indicate significant difference between groups ($p<0.01$). (B) Example of a nerve stained with paraphenylenediamine and a 50 μm×50 μm box delineating the magnification area for three representative images (C) of Mild, Moderate, and Severe classified optic nerve sections (scale bar: 15 μm).
Figure 18B:
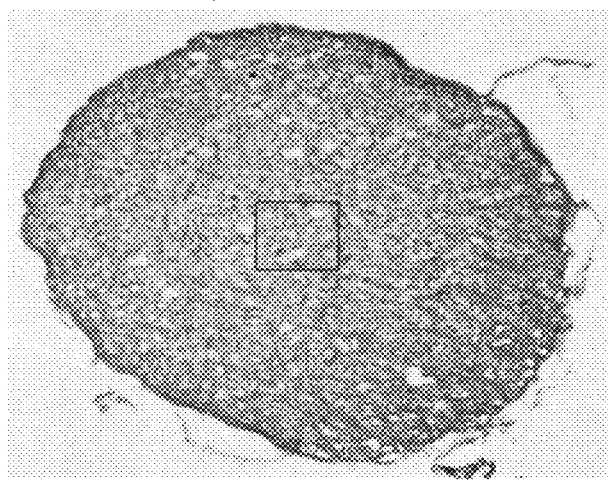
Figure 18C:

Axonal Degeneration Data:

The distribution of optic nerve damage, graded as mild, moderate, and severe, was significantly (p<0.01) skewed more to the severe grading in untreated 12-month-old DBA/2J mice (12%, 22%, 66%, respectively) and mice treated with fibroblast-derived sEV (18%, 24%. 58%, respectively) compared to BMSC-derived sEV treated mice (33%, 37%, 40%, respectively; FIG. 18). These results suggest that BMSC sEV prevents axonal damage in DBA/2J mice.

Discussion

These results demonstrate that BMSC sEV did not affect the development of spontaneous ocular hypertension in the DBA/2J genetic mouse model of glaucoma but protect RBPMS+ RGC from death. The number of degenerating axons in the optic nerve was also significantly diminished after BMSC sEV treatment. However, RGC function deteriorated in all three groups with BMSC sEV only providing a modest significant effect at 6 months. This shows that repeat treatments may be helpful.

DBA/2J mice are a mouse model of glaucoma, specifically pigmentary glaucoma. Mutations in tyrosinase-related protein 1 (Tyrp1) and glycosylated protein nmb (Gpnmb) lead to iris stromal atrophy and iris pigment dispersion, respectively (Anderson et al., *Nature Genetics*. 2001; 30:81). A buildup of pigment and cell debris in the trabecular meshwork overtime attenuates drainage of aqueous humor, leading to a chronic rise in IOP. Because DBA/2J mice are a mouse strain that spontaneously develop ocular hypertension, they avoid complications arising in other glaucoma models that require physical interventions to elevate IOP. A meta-analysis of 1400 DBA/2J mice demonstrated that the initial significant IOP elevation begins at 6 months and peaks at 10-12 months (Libby et al., *Visual neuroscience*. 2005; 22:637-648). Analysis of 772 nerves demonstrates 10-20% of nerves show a degenerative phenotype at 6 months whereas at 12 months, 60-80% of optic nerves were degenerated. At 16-19 months, 80% of optic nerves were degenerated.

As pressure is uniform throughout the eye, it might be expected that RGC die uniformly, but this is not what is observed (Jakobs et al., *The Journal of Cell Biology*. 2005; 171:313-325). RGC display fan-shaped death, narrow at the optic head with the zone devoid of RGC widening as it radiated out to the periphery (Jakobs et al., supra; Panagis et al., *Investigative Ophthalmology & Visual Science*. 2010; 51:2024-2034). This is observed in the human condition, likely due to the compression of axonal bundles as they move through the lamina cribrosa. While lacking a lamina cribrosa, mice do have a glial component which could elicit similar effects (Howell et al., *The Journal of Cell Biology*. 2007; 179:1523-1537; Albrecht, *The Open Ophthalmology Journal*. 2008; 2:94-101). As in the human condition, DBA/2J mice display an age-related rise in IOP, a delay between the ocular hypertension and the degeneration of RGC and their axons, and finally, a sectorial, non-uniform pattern of death.

Exosomes offer significant advantages over cell therapy. As they are non-dividing, they can be accurately dosed. They also may avoid complications associated with transplanting dividing cells into the eye including the retinal detachment and ocular hypertension (Kuriyan et al, *New England Journal of Medicine*. 2017; 376:1047-1053). Following isolation, exosomes can be stored for over 6 months at −80 C° or about two weeks at 4 C° without loss of miRNA quantity or function (Ge et al., *Molecules*. 2014; 19:1568-1575).

By 12 months, the number of RGC was less than 300 RBPMS+ RGC per mm$^2$ in both untreated mice and mice receiving fibroblast-derived sEV. This is similar to other studies demonstrating less than 500 FG+ RGC per mm$^2$ in 10-month-old DBA/2J mice. About 1000 RBPMS+ RGC per mm$^2$ survived in the retina of mice receiving BMSC-derived sEV (FIG. 16). Similar survival has been demonstrated ivit transplantation of GDNF-loaded microspheres, which promoted survival of 1000-1500 RGC at similar time points (Ward et al., *Journal of pharmaceutical sciences*. 2007; 96:558-568).

In this study, human sEV were injected into mice vitreous humor monthly from 3-12 months of age. No evidence of ocular inflammation was observed. Several studies have demonstrated that transplantation of human MSC does not elicit any inflammatory complications (Mead et al., *Cytotherapy*. 2016; 18:487-496; Tan et al., *Clin Intern Aging*. 2015; 10:487-490). The data strongly suggested that BMSC-derived sEV did not elicit any kind of inflammatory rejection in the eye.

Using a well-established grading scales to assess optic nerve damage in DBA/2J mice[24] we demonstrated that mice receiving BMSC-derived sEV performed better on the grading scale, with less nerves being classified as severe and more classified as mild or moderate. Thus, while BMSC-derived sEV are neuroprotective for RGC, they also provide a protective effect on their axons, possibly because the delivery of multiple miRNA via sEV has the potential to interact with multiple neuroprotective pathways that spare the soma and the axon. The results demonstrated efficacy of BMSC sEV, which comprise exosomes, over a one-year period in an animal model of glaucoma. This demonstrates effectiveness over a time period analogous to the human condition.

Example 18

Viral Delivery of Multiple miRNA Promotes Retinal Ganglion Cell Survival and Functional Preservation after Optic Nerve Crush Injury In the present study we expressed combinations of six candidate miRNAs (miR-26a, miR-17, miR-30c-2, miR92a, miR-292, and miR-182) using adeno-associated virus (AAV)-2 in the RGC of rats that have undergone ONC injury and assessed survival, regeneration and functional preservation. These candidates were chosen based on their abundance in the neuroprotective BMSC-derived sEV in comparison to the ineffective fibroblast-derived sEV.

Materials and Methods

All reagents were purchased from Sigma (Allentown, Pa.) unless otherwise specified.

Animals:

Adult female Sprague-Dawley rats weighing 200-220 g (Charles River, Wilmington, Mass.) were maintained in accordance with guidelines. Animals were kept at 21° C. and 55% humidity under a 12 hours light and dark cycle, given food/water ad libitum and were under constant supervision from trained staff. Animals were euthanized by rising concentrations of $CO_2$ before extraction of retinae.

Figures 26A, 26B:
FIGS. 26A-26B are Table A (FIG. 26A) and a schematic diagram (FIG. 26B) of the vector construct used for introducing miRNA. SEQ ID NO: 65 (miR-26a-1), SEQ ID NO: 26 (miR-17), SEQ ID NO: 66 (miR-30c-2), SEQ ID NO: 67 (miR92a-1), SEQ ID NO: 68 (mIR-292) and SEQ ID NO: 69 (mIR-182) are shown in FIG. 26A.

Plasmid and AAV Production:

Backbone for all miRNA constructs is the pscAAV-CMV-ΔelD, modified plasmid used in a previous publication (Kole et al., *Molecular Therapy* 26(1), 219-237. doi: 10.1016/j.ymthe.2017.09.007, 2018) but lacking the D-element in 3′ITR sequence. Cassette of EmGFPmiR_NegControl (Thermo Fisher Scientific, Cincinnati, Ohio; #K4936-00) was subcloned into pscAAV-CMV-ΔelD using GATEWAY® recombination reactions. miRNA loci tested (see FIG. 26A, which is Table A) were obtained from miRBase (mirbase.org).

Individual loci containing a single miRNA stem-loop were generated as PCR primers containing a complementary single-stranded DNA sequence and extended via high-fidelity PCR as one cycle of 15 seconds at 95° C. followed by annealing for 15 sec at 62° C. and extension at 72° C. for 15 sec. Double stranded sequences were subcloned using restriction enzymes SalI and EcoRV into pscAAV-CMV-EmGFPmiR_NegControl-ΔelD vector by replacing the miR_NegControl sequence. Each miRNA sequence was validated by sequencing analysis. Self-complementary AAV production were generated as described (Kole et al., 2018). Briefly, HEK 293T cells were triple transfected with pHelper, pAAV2cap, and pscAAV2-CMV-(GFPmiRNA) plasmids using polyethylenimine. For increasing the screening scale, each viral batch contained the combinations of three different pscAAV2-CMV-(GFPmiRNA) constructs as referred in Table B.

TABLE B

Virus constructs (pscAAV2-CMV-(GFPmiRNA)) used in the present study.
Virus E refers to a combination of both virus A and virus D.

| miRNA | Virus (GFP) | Virus A | Virus B | Virus C | Virus D | Virus E |
|---|---|---|---|---|---|---|
| EmGFPmiR-NegControl | + | | | | | |
| miR-26a | | + | | | | + |
| miR-17 | | + | + | | | + |
| miR-30c-2 | | + | + | + | | + |
| miR-92a | | | + | + | + | + |
| miR-292 | | | | + | + | + |
| miR-182 | | | | | + | + |

The iso-molar combination of plasmids is expected to generate same number of viral particles of each GFPmiRNA. Cells were harvested 48 h after transfection. Viral particles were purified by centrifugation through iodixanol gradient (15, 25, 40, and 60%). The 40% fraction containing the AAV viral particles was collected and passed through the column for desalting. Viral particles were suspended and stored in phosphate-buffered saline (PBS), 0.001% pluronic (Thermo Fisher Scientific; #24040) which prevents attachment of virus to pipette or tube. Titers (viral genomes per ml-vg/ml) were determined by real time PCR using the primers targeting the CMV promoter: 5'-ATGCGGTTTTGGCAGTACAT-3' (SEQ ID NO: 70) and 5'-GTCAATGGGGTGGAGACTTG-3' (SEQ ID NO: 71).

Adult Rat Retinal Cell Culture:

Eight-well chamber slides (Thermo Fisher Scientific) were pre-coated with 100 µg/ml poly-D-lysine/20 µg/ml laminin for 60/30 minutes respectively. After culling and ocular dissection, retinal cells were dissociated into single cells using a Papain Dissociation system according to the manufacturer's instructions (Worthington Biochem, Lakewood, N.J.) and as described previously (Logan et al., 2006). Retinal cells were seeded at 125,000 cells/well in 8-well chamber slides and grown in 300 µl of supplemented Neurobasal-A (25 ml Neurobasal-A (Thermo Fisher Scientific), 1× concentration of B27 supplement (Thermo Fisher Scientific), 0.5 mM of L-glutamine (62.5 µl; Thermo Fisher Scientific) and 50 µg/ml of gentamycin (125 µl; Thermo Fisher Scientific)). Cultures were treated with $1\times10^{11}$ vg/ml in sterile PBS, 0.001% pluronic in a final volume of 5 µl (Table B). All in vitro experiments were run in triplicate from pooled retinae from 2 animals and repeated on three independent occasions (total of 6 separate animals).

Cultures were incubated for 3 days at 37° C. before immunocytochemical staining of RGC with βIII-tubulin to stain cell soma and neurites (Logan et al., Brain 129, 490-502. doi: Doi 10.1093/Brain/Awh706, 2006). For this study, large spherical βIII-tubulin+ retinal cells, which can be identified by preferential βIII-tubulin intensity around the axonal base are referred to as RGC. Previous immunocytochemical analysis of these cultures demonstrates that 60% of these retinal cells are neurons (neurofilament+/βIII-tubulin+), of which 10% are Thy1+ RGC (Suggate et al., Molecular and Cellular Neuroscience 40(4), 451-462. doi: DOI 10.1016/j.mcn.2009.01.004, 2009).

In Vivo Experimental Design:

Twenty female Sprague-Dawley rats (40 eyes) weighing at 200-220 g (~8 weeks) were split into 8 groups (5 eyes per group) based on our previous a priori power calculations (Mead et al., Investigative Ophthalmology & Visual Science 59(2), 702-714. doi: 10.1167/iovs.17-22855, 2014). One group was left intact while the other 7 groups received an optic nerve crush (ONC) on day 0. Intravitreal injection of AAV was given 7 days prior to ONC/day 0 and the experiment finished on day 21. Electroretinography (ERG) and optical coherence tomography (OCT) recording were also done 7 days prior to ONC/day 0 as well as on day 20.

Optic Nerve Crush:

Anesthesia was induced with 5%/95% Isoflurane/$O_2$ (Baxter Healthcare Corp, Deerfield, Ill.)/1.5 L per minute and maintained at 3.5% throughout the procedure whilst analgesia was provided via an intraperitoneal injection of Buprenorphine (0.3 mg/kg). Intraorbital ONC was performed as previously described (Berry et al., Neurobiol Dis 85, 99-110. doi: 10.1016/j.nbd.2015.10.002, 1996). Briefly, the optic nerve was surgically exposed under the superior orbital margin and crushed using fine forceps 1 mm posterior to the lamina cribrosa, taking care to separate the dura mater and under lying retinal artery before crushing.

Intravitreal Injection:

All viruses (Table 2) were delivered at a concentration of $1\times10^{11}$ vg/ml and in a final volume of 5 µl in sterile PBS, 0.001% pluronic, 7 days prior to ONC. Intravitreal injections, posterior to the limbus, were performed under isoflurane-induced anaesthesia (described above) using a pulled glass micropipette, produced from a glass capillary rod (Harvard Apparatus, Kent, UK) using a Flaming-Brown micropipette puller (Sutter Instruments, Novato, Calif., USA) with care taken not to damage the lens.

Electroretinography (ERG):

ERG was recorded using the Espion Ganzfeld full field system (Diagnosys LLC, Lowell, Mass.) 7 days prior to ONC (baseline) and 20 days post-ONC. Rats were dark adapted for 12 hours overnight and prepared for ERG recording under dim red light (>630 nm). Anesthesia was induced with intraperitoneal injection of Ketamine (100 mg/kg; Putney Inc, Portland, Me.)/Xylazine (10 mg/kg; Lloyd Inc, Shenandoah, Iowa) and eyes dilated with tropicamide. Scotopic flash ERG was recorded from −5.5 log (cd s) $m^{-2}$ to 1.0 log (cd s) $m^{-2}$ in 0.5 log unit increments and traces were analyzed using in built Espion software. Traces at a light intensity of −5.0 log (cd s) $m^{-2}$ were chosen for analysis as they produced a clean, unambiguous positive scotopic threshold (pSTR) at approximately 100 ms after stimulus, of which the peak amplitude was recorded. All readings and analysis were performed by an individual masked to the treatment groups.

Optical Coherence Tomography Measurements of the Retinal Nerve Fiber Layer:

OCT was performed on rats under anesthesia (Ketamine and Xylazine, as above) 7 days prior to ONC (baseline) and 20 days post-ONC. A Spectralis HRA3 confocal scanning laser ophthalmoscope (Heidelberg Engineering, Heidelberg, Germany) was used to image the retinal nerve fiber layer (RNFL) surrounding the optic nerve head and in-built software segmented the RNFL and quantified the thickness. Segmentation was manually adjusted when necessary (by an individual masked to the treatment group) to prevent inclusion of blood vessels that populate the RNFL.

Tissue Preparation:

At 21 days post-ONC, animals were sacrificed with $CO_2$ overdose and perfused intracardially with 4% paraformaldehyde (PFA) in PBS. Eyes and optic nerves were dissected and immersion fixed in 4% PFA in PBS for a further 2 hours at 4° C. before cryoprotection in 10%, 20% and 30% sucrose solution in PBS for 24 hours and stored at 4° C. Eyes and optic nerves were embedded using optimal cutting temperature embedding medium (VWR International Inc, Bridgeport, N.J.) in peel-away mold containers (VWR International Inc) by rapid freezing with ethanol/dry ice before storage at −80° C. Eyes and optic nerves were sectioned on a CM3050S cryostat microtome (Leica Microsystems Inc, Bannockburn, Ill.) at −22° C. at a thickness of 20 µm and 14 µm, respectively, and mounted on positively charged glass slides (Superfrost Plus, Thermo Fisher Scientific). Parasagittal eye and optic nerve sections were left to dry onto slides overnight at 37° C. before storage at −20° C. To ensure RGC counts were taken in the same plane, eye sections were chosen with the optic nerve head visible.

Immunocytochemistry:

Retinal cultures were fixed in 4% PFA in PBS for 10 minutes, washed for 3×10 minutes of PBS, blocked in blocking solution (3% bovine serum albumin (g/ml), 0.1% Triton X-100 in PBS) for 20 minutes and incubated with primary antibody (βIII-tubulin, 1:500, Sigma, #T-8660)) diluted in antibody diluting buffer (ADB; 0.5% bovine serum albumin, 0.3% Tween-20 in PBS) for 1 hour at room temperature. Cultures were washed for 3×10 minutes in PBS, incubated with the secondary antibody (Mouse IgG 488, 1:400, ThermoFisher, #A-11001) diluted in ADB for 1 hour at room temperature, washed for 3×10 minutes in PBS, mounted in Vectorshield mounting medium containing DAPI (Vector Laboratories) and stored at 4° C.

Immunohistochemistry:

Mounted tissue sections were equilibrated to room temperature, washed in PBS for 2×5 minutes, permeabilised in 0.1% Triton x-100 in PBS for 20 minutes and washed for 2×5 minutes in PBS. Sections were blocked in blocking buffer (75 µl; 0.5% bovine serum albumin (g/ml), 0.3% Tween-20, 15% normal goat/donkey serum (Vector Laboratories) in PBS) in a humidified chamber for 30 minutes and incubated with primary antibody (RNA-binding protein with multiple splicing (RBPMS), 1:500, ThermoFisher, #ABN-1376; growth associated protein-43 (GAP-43), 1:400, ThermoFisher, #33-5000) diluted in ADB (15% normal goat serum in place of bovine serum albumin) overnight at 4° C. The following day, slides were washed for 3×5 minutes in PBS and incubated with secondary antibody (Mouse IgG 488, 1:400, ThermoFisher, #A11001; Guinea Pig IgG 546, 1:400, ThermoFisher, #A-11074) diluted in ADB for 1 hour at room temperature. Slides were washed for 3×5 minutes in PBS, mounted in Vectorshield mounting medium containing DAPI (Vector Laboratories) and stored at 4° C. before microscopic analysis. Negative controls including omission of primary antibody were included in each run and were used to set the background threshold levels prior to image capture.

Microscopy and Analysis:

All fluorescently stained sections were analyzed by an operator blinded to the treatment groups. For immunocytochemistry, wells were divided into 40 equal boxes and 12 were selected at random. βIII-tubulin$^+$ retinal cells (identified by their staining morphology and referred to from here on as RGC), with or without neurites, were counted in each selected box. Fluorescently stained cells were analysed using a Zeiss Z1 epifluorescence microscope (Carl Zeiss Inc, Thornwood, N.Y.). Neurite outgrowth was measured by dividing the well into 9 equal sectors and the length of the longest neurite of each RGC in each sector was measured using Axiovision software (Carl Zeiss Inc). All in vitro experiments were run in triplicate from pooled retinae from 2 animals and repeated on three independent occasions (total of 6 separate animals).

For immunohistochemistry of retina, RBPMS$^+$ RGC were counted in 20 µm-thick sections (imaged using a Zeiss LSM 700 confocal laser-scanning microscope) along a 250 µm linear region of the ganglion cell layer (GCL) either side of the optic nerve as previously described (Mead et al., *Ophthalmology & Visual Science* 59(2), 702-714. doi: 10.1167/iovs.17-22855, 2014). Six sections per retina and 5 retinae (from 5 different animals) per treatment group were quantified. For immunohistochemistry of the optic nerve, GAP-43$^+$ axons were counted in 14 µm thick longitudinal sections, imaged using a Zeiss LSM 700 confocal laser-scanning microscope and image composites created using Photoshop CS6 (Adobe Systems, Inc., San Jose, Calif.). The number of axons were quantified at 100, 200 and 500 µm distance intervals extending distal to the laminin$^+$ crush site. Three sections per optic nerve and 5 optic nerves (from 5 different animals) per treatment group were quantified. The diameter of the nerve was measured at each distance to determine the number of axons/mm width. This value was then used to derive Σad, the total number of axons extending distance d in an optic nerve with radius r using:

$$\sum_{ad} = \pi r^2 \times \frac{\text{average number of axons/mm width}}{\text{section thickness (0.015 mm)}}$$

Statistics:

Animal numbers were determined beforehand using a power calculation (Faul et al., *Behav Res Methods* 39(2), 175-191, 2007; Mead et al., *Ophthalmology & Visual Science* 59(2), 702-714. doi: 10.1167/iovs.17-22855, 2014). All statistical tests were performed using SPSS 17.0 (IBM SPSS, Inc., Chicago, Ill.) and data presented as mean±standard error of the mean (SEM) with graphs constructed using Graphpad Prism (La Jolla, Calif.). Normal distribution was verified by Shapiro-Wilkes test prior to parametric testing using a one-way analysis of variance (ANOVA) with a Tukey post-hoc test. Statistical differences Results Viral Delivery of miRNA Promotes a Trend Towards RGC Neuroprotection/Neuritogenesis in Mixed Primary Retinal Cultures:

Six miRNAs were selected for testing their therapeutic efficacy. Their selection was based on their abundance in neuroprotective BMSC-derived sEV versus lower abundance in fibroblast-derived sEV. Several of the selected miRNAs (miR-26a, miR-17-5p, miR-92a) were implicated in the down-regulation of PTEN expression (Li and Yang, *Oncotarget* 3(12), 1653-1668. doi: 10.18632/oncotarget.81, 2012; Zhang et al., *Journal of Cellular Physiology* 0(0). doi: doi:10.1002/jcp.27549, 2014; Ding et al., *Pathology—Research and Practice* 213(5), 467-475. doi: https://doi.org/10.1016/j.prp.2017.01.026 2017). PTEN knockdown was shown to promote RGC neuroprotection and axon regeneration after ONC (Park et al., *Science* 322(5903), 963-966. doi: 10.1126/science.116156600, 2008). To increase the efficiency of initial testing, combinations of three miRNAs produced by 5 different recombinant AAV were used.

Mixed primary retinal cultures infected with different recombinant AAV were used to test neuroprotective effects of miRNA in vitro. Control experiments showed that AAV2 virus expressing GFP transfected 50.1±4.1% cells in retinal cultures (FIG. 24A).

Viral delivery of miRNA to these cultures elicited some RGC neuroprotection with virus C and D promoting the greatest neuroprotection (220.3±17.4, 220.6±25.1 RGC/well, respectively) followed by virus A, B and E (176.6±20.1, 196.1±13.2, 212.4±12.3 RGC/well) in comparison to PBS (statistically significant) and virus (GFP) (not statistically significant) treated controls (156.3±10.5, 170.0±21.1 RGC/well; FIG. 25A).

Figure 25B:
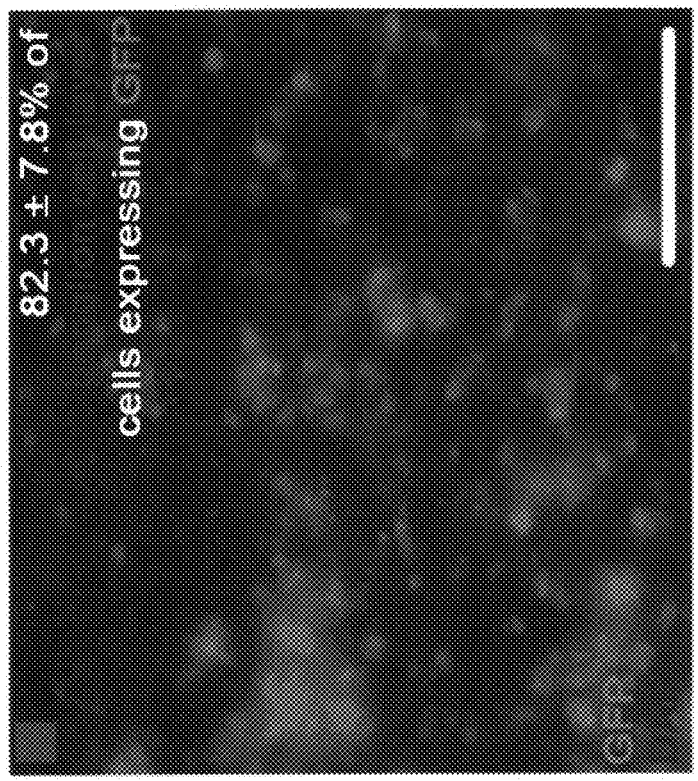
FIGS. 25A-25B. Retinal GFP expression. Representative image and transfection efficiency of retinal culture (A) and retinal wholemount (B) treated with AAV2 virus expressing GFP (green) and counter stained with DAPI (blue) are shown. Cultures were 3 days post-treatment and wholemounts were from an animal one week after intravitreal injection, representative of 5 animals per group (scale bar 100 µm).
Figure 25A:
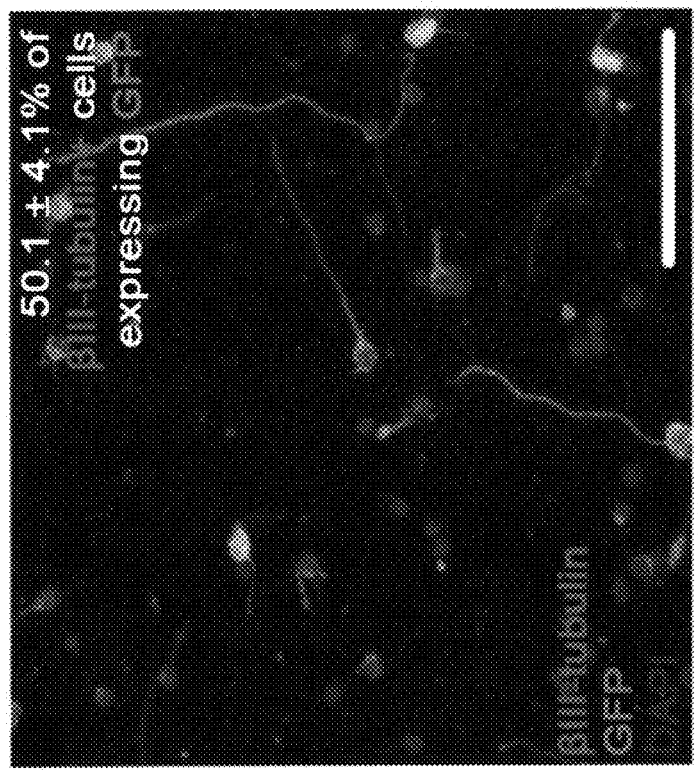

Neuritogenesis was measured as the average length of the longest neurite (FIG. 25B). While viral delivery of miRNA (virus A, B, C, D and E) trended towards a neuritogenic effect (216.1±60.3, 217.1±34.4, 201.0±30.9, 226.6±40.0, 282.0±50.0 respectively) in comparison to PBS treated controls (126.4±10.3 μm), they did not in comparison to virus (GFP) treated controls (192.1±35.9 μm). No statistically significant differences were seen.

Viral Delivery of miRNA Preserves RNFL Thickness after ONC:

To test neuroprotective effects of miRNA in vivo, an ONC injury model was used. Control experiments demonstrated that AAV2 expressing GFP transfected 82.3±7.8% RGC after intravitreal injection in our conditions (FIG. 24B).

The thickness of the RNFL was used as a measure of RGC axonal density (FIG. 19). In untreated animals without ONC, RNFL thickness (46.4±1.3 μm) was no different from baseline (47.1±0.5 μm; baseline was day 0 measurement from all animal groups). In animals receiving virus A and C, RNFL thickness (25.8±1.9, 27.0±3.1 respectively) was not significantly different from PBS and virus (GFP) treated control animals (24.0±0.6, 24.8±2.1 respectively). In contrast, in virus B, D and E treated animals, RNFL thickness (34.3±2.1, 37.0±1.5, 36.0±1.0 respectively) was significantly higher than PBS and virus (GFP) treated control animals.

Viral Delivery of miRNA Promotes Neuroprotection of RGC Following ONC:

ONC (PBS and virus (GFP) treated control) induced a significant loss of RBPMS$^+$ RGC by day 21 (4.7±3.7 and 2.5±0.5/mm of retina, respectively) compared to untreated controls without ONC (93.0±7.8/mm of retina; FIG. 20). While intravitreal delivery of virus A yielded no neuroprotective effect (6.0±0.6/mm of retina), virus B, C, D and E provided significant neuroprotection of RBPMS$^+$ RGC (24.9±14.2, 18.3±3.4, 11.3±2.7, 14.4±1.5/mm of retina, respectively) compared to PBS and virus (GFP) treated controls.

Figure 21A:
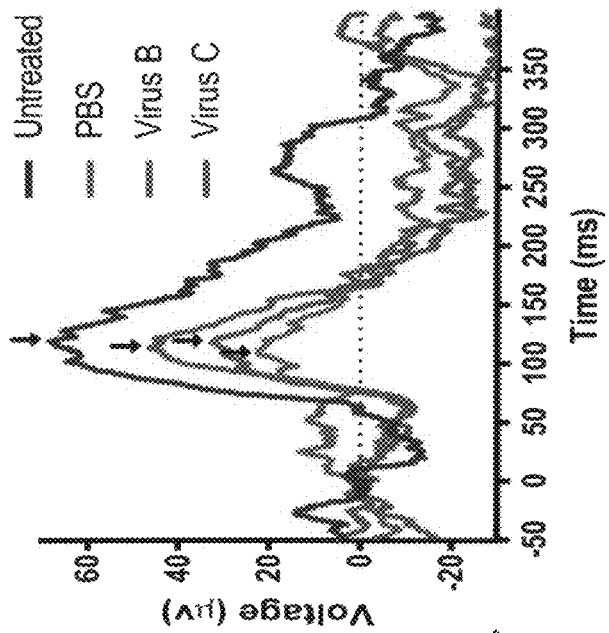
FIGS. 21A-21B. pSTR amplitude after ONC. Mean pSTR amplitude measured with ERG 21 days after ONC (A). Asterisks indicate significant differences (p<0.05) from PBS and virus (GFP) control treated animals. Representative traces from the 5 animals per group are shown (B). Black arrows indicate peak amplitude that was recorded as the pSTR.
Figure 21B:
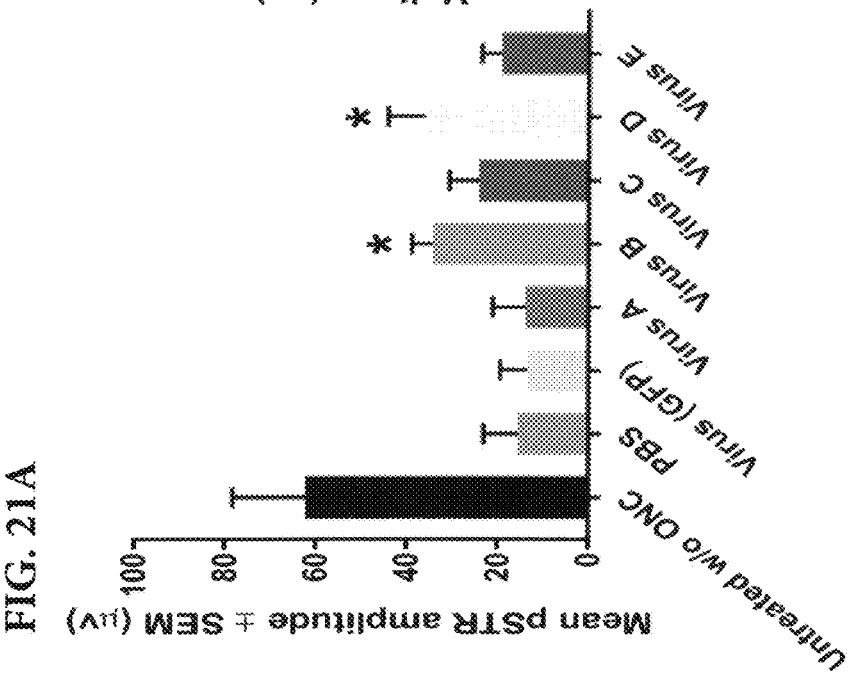

Viral Delivery of miRNA Preserves RGC Function:

The amplitude of the pSTR was used as a measure of RGC function (FIG. 21). In PBS and virus (GFP) treated control animals, pSTR amplitude decreased significantly (15.7±7.4, 13.5±5.9 μv, respectively) compared to untreated animals without ONC (62.4±16.0 μv). While intravitreal delivery of virus A, C and E yielded no significant preservation of pSTR amplitude (13.9±7.3, 24.4±6.2, 19.3±4.3 μv, respectively), virus B and D significantly preserved pSTR amplitude (34.5±4.4, 36.0±8.0 μv, respectively) compared to PBS and virus (GFP) treated controls.

Figure 22A:
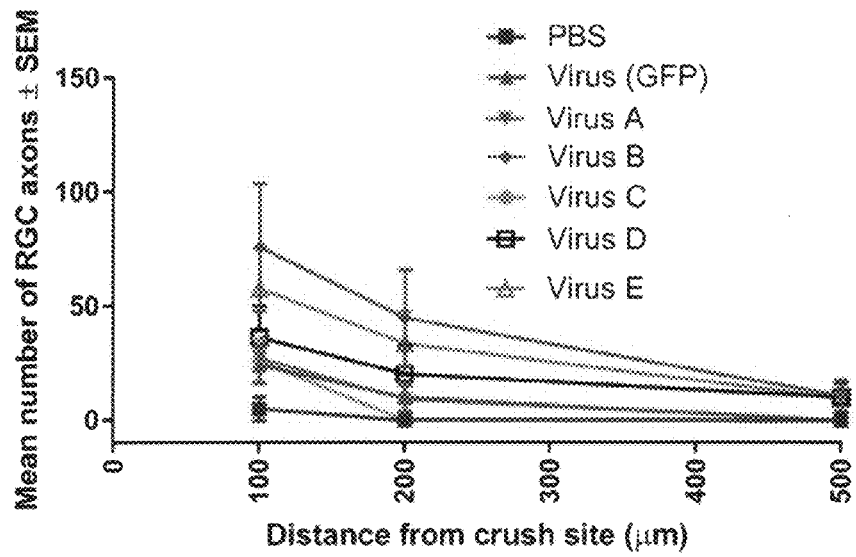
FIGS. 22A-22B. Regeneration of axons in the optic nerve. Mean number of GAP-43$^+$ axons at 100-500 µm from the laminin$^+$ crush site (A). Representative image (from 5 animals) of an optic nerve from animals treated with virus B or virus (GFP) control, immunohistochemically stained for laminin (red) and GAP-43 (yellow) are shown (B; scale bar 100 µm).
Figure 22B:
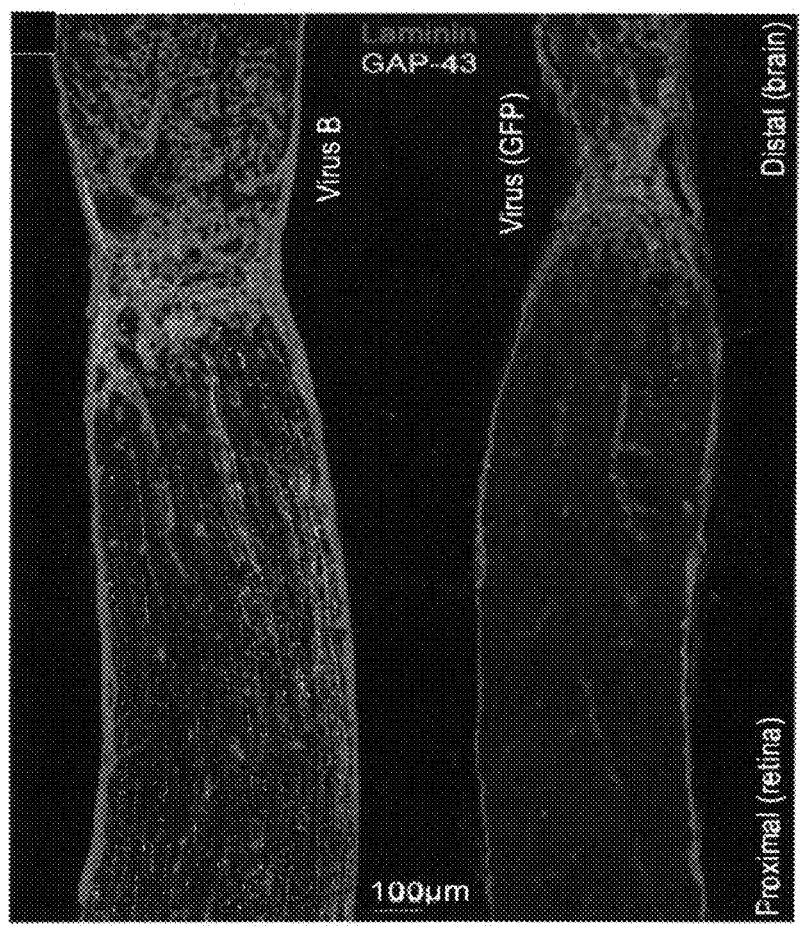

Viral Delivery of miRNA Promotes Limited Sprouting but not Regeneration of RGC Axons Following ONC:

No significant long-distance axon regeneration was observed in the experimental groups tested (FIG. 22). The most pronounced regeneration/sprouting was seen after intravitreal delivery of virus B with many GAP-43$^+$ axons observed in the optic nerve proximal to the lesion. Distal to the laminin$^+$ crush site, the number of axons was only significantly higher (p<0.05) at 100 μm from the crush site (76.1±27.9 axons) compared to virus (GFP) treated controls (24.4±8.1 axons).

Figure 23:
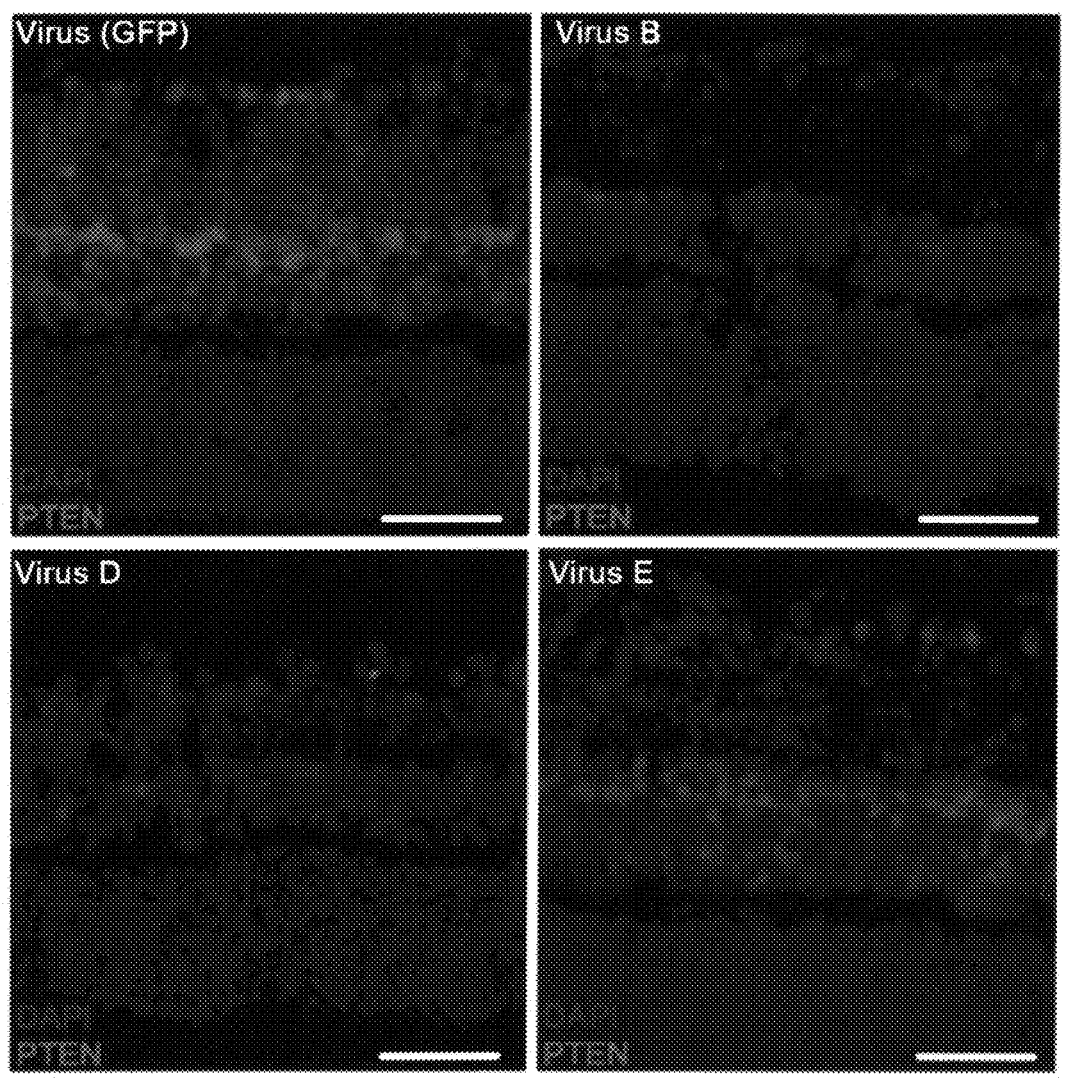
FIG. 23. Retinal PTEN expression after ONC. Representative images of parasagittal retinal sections stained for PTEN (red) and DAPI (blue), from 5 animals treated with virus (GFP) control, virus B, virus D and virus E are shown (scale bar 100 µm).

Viral Delivery of Selective miRNA Promoted Downregulation of PTEN:

Many of the delivered miRNA target PTEN mRNA and immunohistochemical staining of retinal sections reflected this, demonstrating that virus B and D promoted significant downregulation of PTEN in comparison to virus (GFP) delivery (FIG. 23).

Thus, the neuroprotective and axogenic properties of six candidate miRNAs that were identified as more abundant in BMSC-sEV than in fibroblast sEV were tested (Mead et al., *Cytotherapy* 18(4), 487-496. doi: 10.1016/j.jcyt.2015.12.002, 2016; Mead and Tomarev, *Stem cells translational medicine* 6(4), 1273-1285. doi: 10.1002/sctm.16-0428, 2017).

Various combinations of these miRNAs were preferentially expressed in the RGC of adult rats using an AAV2 viral vector. AAV serotypes have varying preference for cell types with AAV2 being the optimal serotype for delivery into RGC. AAV2 transfects approximately 85% of RGC after delivery into the vitreous body (Harvey et al., *Molecular and Cellular Neuroscience* 21(1), 141-157. doi: https://doi.org/10.1006/mcne.2002.1168, 2002; Martin et al., *Investigative Ophthalmology & Visual Science* 44(10), 4357-4365. doi: 10.1167/iovs.02-1332, 2003). Comparable efficacy was also observed in these experiments with all viruses confirmed to transfect >80% of RGC in vivo in the present study (FIG. 24). While transfection is still possible in RGC injured by ONC (Nickells et al., *Investigative Ophthalmology & Visual Science* 58(14), 6091-6104. doi: 10.1167/iovs.17-22634, 2017), transfection was performed 1 week prior to the ONC, as it has been shown that AAV2-GFP takes 1 week before optimal expression is seen in RGC (Smith and Chauhan, *Scientific Reports* 8(1), 1490. doi: 10.1038/s41598-018-19969-9, 2018). Intravitreal delivery of AAV2 shows no detrimental effects on RGC, as measured by ERG (pSTR and nSTR) as well as OCT (RNFL) (Smith and Chauhan, supra, 2018).

Many of the candidate miRNAs used in the present experiments targeted PTEN including miR-26a, demonstrated in gastric cancer cells (Ding et al., *Pathology—Research and Practice* 213(5), 467-475. doi: https://doi.org/10.1016/j.prp.2017.01.026, 2017), miR-17-5p, demonstrated in glioblastoma cells (Li and Yang, *Oncotarget* 3(12), 1653-1668. doi: 10.18632/oncotarget.810, 2012) and prostate cancer cells (Dhar et al., *Oncotarget* 6(29), 27214-27226. doi: 10.18632/oncotarget.4877, 2015), and miR-92a, demonstrated in a variety of paradigms (Zhang et al., 2014; Ke et al., *Annals of Surgical Oncology* 22(8), 2649-2655. doi: 10.1245/s10434-014-4305-2, 2015; Serr et al., *Proceedings of the National Academy of Sciences* 113 (43), E6659-E6668. doi: 10.1073/pnas.1606646113, 2016; Lu et al., *International Journal of Oncology* 51(1), 235-244. doi: 10.3892/ijo.2017.3999, 2017; Xiao et al., *Oncology Reports* 37(4), 2513-2521. doi: 10.3892/or.2017.5484, 2017). Delivery of virus B (miR-17-5p, miR-30c-2 and miR-92a) and virus D (miR-92a, miR-292 and miR-182)

promoted significant neuroprotection, preservation of RNFL thickness as measured by OCT, and preservation of RGC function, as measured by ERG. These effects coincided with a robust knockdown of PTEN within the retina, in contrast to virus (GFP) controls where PTEN was expressed in the GCL and inner nuclear layer. In virus B treated animals, the most substantial neuroprotection of RGC was seen along with minor pre-lesion sprouting of their axons. This distinction can thus explained by the presence of miR-17-5p and miR-30c-2 in virus B but not virus D, which may target SOCS6 (Wu et al., *FEBS Letters* 588(12), 2055-2062. doi: doi:10.1016/j.febslet.2014.04.036, 2014) and BCL9 (Jia et al., *Molecular Cancer Research* 9(12), 1732, 2011), amongst many other predicted targets. Interestingly these miR were expressed in virus A yet showed no therapeutic effect, demonstrating that their combination with miR-92a is required to elicit the positive effects seen.

While the in vitro experiment demonstrated a trend towards neuroprotection/neuritogenesis, no significant effects were seen. This could be explained by the shorter duration afforded for successful transfection in vitro and the subsequently reduced transfection efficiency (50.1±4.1%) we observed (FIG. 24).

Thus, it was demonstrated that virally delivered miRNA can significantly protect RGC and their axons from degeneration and dysfunction. The mechanism of action is likely multifaceted, and multiple miRNA likely are required. Without being bound by theory, PTEN, a confirmed target of many of the delivered miRNA, was successfully down-regulated and coincided with the therapeutic effects observed.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for treating glaucoma in a subject, comprising:
    selecting a subject with glaucoma, and
    locally administering to an eye of the subject a therapeutically effective amount of exosomes from mesenchymal stem cells, thereby treating the glaucoma in the subject.

2. The method of claim 1, wherein the exosomes are from human mesenchymal stem cells, and wherein the subject is human.

3. The method of claim 1, wherein the mesenchymal stem cells were treated with a priming agent.

4. The method of claim 3, wherein the priming agent is tumor necrosis factor (TNF)-$\alpha$.

5. The method of claim 1, wherein the exosomes are from bone marrow derived mesenchymal stem cells, umbilical cord blood derived mesenchymal stem cells, adipose tissue derived mesenchymal stem cells, or dental pulp stem cells.

6. The method of claim 1, wherein the exosomes are $CD11c^+$ and $CD63^+$.

7. The method of claim 1, wherein the exosomes are administered intravitreally to the eye of the subject.

8. The method of claim 1, wherein the mesenchymal stem cell exosomes are administered repeatedly to the eye of the subject.

9. The method of claim 8, wherein the mesenchymal stem cell exosomes are administered weekly, bi-monthly or monthly to the subject.

10. The method of claim 1, wherein the administration of the exosomes increases retina ganglion cell survival in the eye of the subject.

11. The method of claim 1, further comprising administering to the subject a therapeutically effective amount of an agent that lowers intraocular pressure,
    wherein the agent that lowers intraocular pressure is a) a prostaglandin analog, b) a beta-adrenergic blocker, c) an alpha-adrenergic agonist, or d) a cholinergic agonist.

12. The method of claim 11, wherein the agent that lowers intraocular pressure is a) latanoprost, b) timolol, c) brimonidine, or d) pilocarpine.

13. The method of claim 1, wherein the exosomes are from a) bone marrow derived mesenchymal stem cells; and b) $CD11c^+$ and $CD63^+$.

* * * * *